(12) United States Patent
Lin et al.

(10) Patent No.: US 9,353,061 B2
(45) Date of Patent: May 31, 2016

(54) 3,5,N-TRIHYDROXY-ALKANAMIDE AND DERIVATIVES: METHOD FOR MAKING SAME AND USE THEREOF

(71) Applicants: Academia Sinica, Taipei (TW); National Taiwan University, Taipei (TW)

(72) Inventors: Jung-Hsin Lin, Taipei (TW); Jim-Min Fang, Taipei (TW); Ting-Rong Chern, Taipei (TW); Jhih-Bin Chen, Changhua County (TW); Ching-Chow Chen, Taipei (TW); Tzu-Tang Wei, Taipei (TW)

(73) Assignees: ACADEMIA SINICA, Taipei (TW); NATIONAL TAIWAN UNIVERSITY, Taipei (TW)

( * ) Notice: Subject to any disclaimer, the term of this patent is extended or adjusted under 35 U.S.C. 154(b) by 0 days.

(21) Appl. No.: 14/416,051

(22) PCT Filed: Jul. 19, 2013

(86) PCT No.: PCT/US2013/051247
§ 371 (c)(1),
(2) Date: Jan. 20, 2015

(87) PCT Pub. No.: WO2014/015235
PCT Pub. Date: Jan. 23, 2014

(65) Prior Publication Data
US 2015/0148360 A1    May 28, 2015

Related U.S. Application Data

(60) Provisional application No. 61/674,290, filed on Jul. 20, 2012.

(51) Int. Cl.
| | |
|---|---|
| *A61K 31/221* | (2006.01) |
| *C07D 215/14* | (2006.01) |
| *C07C 259/08* | (2006.01) |
| *A61K 31/401* | (2006.01) |
| *A61K 31/4045* | (2006.01) |
| *A61K 31/44* | (2006.01) |
| *A61K 31/47* | (2006.01) |
| *A61K 31/505* | (2006.01) |
| *A61K 45/06* | (2006.01) |
| *C07C 259/06* | (2006.01) |
| *C07D 207/34* | (2006.01) |
| *C07D 209/24* | (2006.01) |
| *C07D 213/56* | (2006.01) |
| *C07D 239/42* | (2006.01) |

(52) U.S. Cl.
CPC ............ *C07D 215/14* (2013.01); *A61K 31/221* (2013.01); *A61K 31/401* (2013.01); *A61K 31/4045* (2013.01); *A61K 31/44* (2013.01); *A61K 31/47* (2013.01); *A61K 31/505* (2013.01); *A61K 45/06* (2013.01); *C07C 259/06* (2013.01); *C07C 259/08* (2013.01); *C07D 207/34* (2013.01); *C07D 209/24* (2013.01); *C07D 213/56* (2013.01); *C07D 239/42* (2013.01); *C07B 2200/07* (2013.01); *C07C 2102/28* (2013.01)

(58) Field of Classification Search
CPC .. C07D 215/14; C07D 207/34; C07D 209/24; C07D 213/56; C07D 239/42; A61K 31/221; A61K 31/401; A61K 31/4045; A61K 31/44; A61K 31/47; A61K 31/505; A61K 45/06
See application file for complete search history.

(56) References Cited

U.S. PATENT DOCUMENTS

| 5,700,811 A | 12/1997 | Breslow et al. |
| 5,804,601 A | 9/1998 | Kato et al. |
| 6,989,401 B2 | 1/2006 | Maeda et al. |

FOREIGN PATENT DOCUMENTS

IN    1492CHE2007 A   *   1/2009

OTHER PUBLICATIONS

J. Luo et al., 36 Cell, 823-837 (2009).*
T. Soussi 60 Cancer Research, 1777-1788 (2000).*
P. Lissoni et al, 7 Cancer Research, 397-401 (2009).*
(Continued)

*Primary Examiner* — Alexander R Pagano
(74) *Attorney, Agent, or Firm* — Muncy, Geissler, Olds & Lowe, P.C.

(57) ABSTRACT

The present invention provides novel compounds of Formula (I), and pharmaceutically compositions thereof. Compounds of Formula (I) are inhibitors of histone deacetylases (HDACs) and 3-hydroxy-3-methylglutaryl coenzyme A (HMG-CoA) reductase (HMGR). Also provided are methods of using the compounds and pharmaceutical compositions for inhibiting the activity of HDACs and HMGR, treating diseases associated with HDACs or HMGR (e.g., cancer, hypercholesterolemia, an acute or chronic inflammatory disease, autoimmune disease, allergic disease, pathogen infection, neurodegenerative disease, and a disease associated with oxidative stress), or inhibiting drug resistance of cancer cells.

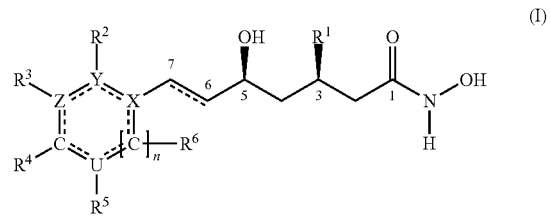

28 Claims, 16 Drawing Sheets

(56) References Cited

OTHER PUBLICATIONS

National Cancer Institute (http://www.cancer.gov/) (Downloaded May 29, 2014).*
F. Bunz, Principles of Cancer Genetics 1-47, 1 (2008).*
P.K. Kuppen et al., 115 Histochemistry and Cell Biology, 67-72 (2001).*
D. Scheinberg et al., Management of Acute Leukemias, in 2 Cancer Principles & Practice of Oncology 2088, 2092 (V.T. DeVita, Jr. et al. eds., 7th ed., 2005).*
D. Druker et al., Chronic Myelogenous Leukema, in 2 Cancer Principles & Practice of Oncology 2121 (V.T. DeVita, Jr. et al. eds., 7th ed., 2005).*
S. O'Brien et al., Chronic Lymphoid Leukemias, in 2 Cancer Principles & Practice of Oncology 2133 (V.T. DeVita, Jr. et al. eds., 7th ed., 2005).*
S. Faderi et al., Myelodysplastic Syndromes, in 2 Cancer Principles & Practice of Oncology 2133 (V.T. DeVita, Jr. et al. eds., 7th ed., 2005).*
H.A. Fine, Neoplasms of the Central Nervous System in, 2 Cancer Principles & Practice of Oncology 1834-1887 (V.T. DeVita, Jr. et al. eds., 5th ed., 2005).*
D. D'Ambrosio et al., 273 Journal of Immunological Methods 3-13 (2003).*
P.J. Koelink et al., 133 Pharmacology & Therapeutics, 1-18 (2012).*
S.K. Bhatia et al., Autoimmunity and autoimmune disease in 6 Principles of Medical Biology 239-263, 244 (1996).*
S.M. Hayter et al., Autoimmunity Reviews, 754-765 (2012).*
G.W. Volcheck, Clinical Allergy: Diagnosis and Management (2009).*
E. R. Sutherland et al., 350 The New England Journal of Medicine, 2689-2697 (2004).*
S. Judge et al., 111 Pharmacology & Therapeutics, 224-259 (2006).*
V. Brinkmann et al., 9 Nature Reviews | Drug Discovery, 883-897 (2010).*
M. Pohanka, 58 Folia Microbiologica, 503-513 (2013).*
J.A. Marwick et al., 11 Expert Opinion on Therapeutic Targets, 745-755 (2007).*
P. Portanova et al., 33 International Journal of Oncology, 325-331 (2008).*
Z-P Jiang et al., 74 Medical Hypotheses, 92-94 (2010).*
J.S. Carew et al., 110 Blood, 313-322 (2007.*
Y.K. Kim et al., 368 Biochemical and Biophysical Research Communications, 959-964 (2008).*
S. Hauswald et al., 15 Clinical Cancer Research, 3705-3715 (2009).*
B. Muller et al., Antiviral Strategies in, Antiviral Strategies 1-24, 4 (H.-G. Krausslich et al., eds., 2009).*
J.D. Henderer et al., Ocular Pharmacology, in Goodman & Gilman's the Pharmacological Basis of Therapeutics 1679-1737 (L. Burnton et al. eds., 11th ed., 2006).*
P.K. Buxton, ABC of Dermatology [e-book] (4th ed., BMJ Books, 2003).*
L.P. P Fox et al., Dermatological Pharmacology, in Goodman & Gilman's the Pharmacological Basis of Therapeutics 1679-1705 (L. Burnton et al. eds., 11th ed., 2006).*
Y.S. Yoon et al., 9 The International Journal of Tuberculosis and Lung Disease, 1215-1219 (2005).*
H. Girouard et al., 100 Journal of Applied Physiology, 328-335, 332 (2006).*
R. S. Shah et al., 52 Biomedicine & Pharmacotherapy, 199-207 (2008).*
J.T. O'Brien et al., 2 The Lancet Neurology, 89-98, 96 (2003).*
J.E. Bolden et al., 5 Nature Reviews Drug Discovery, 769-784, 769 (2006).*
M. Dokmanovic et al., 5 Molecular Cancer Research, 981-989 (2007).*
W. Weichert, 280 Cancer Letters, 168-176 (2009).*
S.V. Chittur et al., 9 BMC Genomics, 1-14 (2008).*
A. Kazantsev et al., 7 Nature Review—Drug Discovery, 854-868 (2008).*

T. Abel et al., 8 Current Opinion in Pharmacology 57-64 (2008).*
T.A. Denison et al., Heterogeneity of Cancers and Its Implication for Targeted Drug Delivery in, Cancer Targeted Drug Delivery an Elusive Dream, 337-362 (Y.H. Bae et al., eds., 2013)b.*
Bolden, J. E.; Peart, M. J.; Johnstone, R. W., Nature Reviews Drug Discovery 2006, 5, 769-784, "Anticancer activities of histone deacetylase inhibitors."
Chan, K. K. W.; Oza, A. M.; Siu, L. L. Clin., Cancer Res. 2003, 9, 10-19, "The Statins as Anticancer Agents."
Frantz, S., Nature Reviews Drug Discovery, Nov. 2006, vol. 5, 881-882, "The trouble with making combination drugs."
Gan, Y.; Wang, J.; Coselli, J.; Wang, X. L. Biochem. Biophys. Res. Commun. Jan. 11, 2008, 365(2), 386-392, "Synergistic Induction of Apoptosis by HMG-CoA Reductase Inhibitor and Histone Deacetylases Inhibitor in HeLa Cells."
Gauthaman, K.; Fong, C. Y.; Bongso, A. J., Cellular Biochem. 2009, 106, 975-983, "Statins, Stem Cells, and Cancer."
Girgert, R.; Vogt, Y.; Becke, D.; Bruchelt, G.; Schweizer, P., Cancer Letters 1999, 137, 167-172, "Growth inhibition of neuroblastoma cells by lovastatin and L-ascorbic acid is based on different mechanisms."
Hawk, E.; Viner, J. L., New Engl. J. Med. May 26, 2005, 352, 2238-2239, "Statins and cancer—beyond the 'one drug, one disease' model."
Istvan, E. S.; Deisenhofer, J., Science May 11, 2001, 292, 1160-1164, "Structural Mechanism for Statin Inhibition of HMG-CoA Reductase."
Jenuwein, T.; Allis, C. D., Science Aug. 10, 2001, 293, 1074-1080, "Translating the Histone Code."
Jones, K. D.; Couldwell, W. T.; Hinton, D. R.; Su, Y.; He, S.; Anker, L.; Law, R. E., Biochem. Biophys. Res. Commun. Dec. 30, 1994, 205, 1681-1687, "Lovastatin induces growth inhibition and apoptosis in human malignant giloma cells."
Kapur, N. K., Expert Rev. Cardiovascular Ther., 2007, 5, 161-175, "Rosuvastatin: a highly potent statin for the prevention and management of coronary artery disease."
Keith, C. T.; Borisy, A. A.; Stockwell, B. R., Nature Reviews Drug Discovery Jan. 2005, 4, 71-78, "Multicomponent therapeutics for networked systems."
Khanzada, U. K.; Pardo, O. E.; Meier, C.; Downward, J. Seckl, M. J.; Arcaro, A., Oncogene 2006, 25, 877-887, "Potent inhibition of small-cell lung cancer cell growth by simvastatin reveals selective functions of Ras isoforms in growth factor signalling."
Klawitter, J.; Shokati, T.; Moll, V.; Christians, U., Breast Cancer Res. 2010, 12, R16, "Effects of lovastatin on breast cancer cells: a proteometabonomic study."
Kizer, J. R.; Medias, C.; Wilner, B.; Vaughan, C. J.; Mushlin, A. I.; Trushin, P.; Gotto, A. M., Jr.; Pasternak, R. C., Am. J. Cardiology May 1, 2010, 105(9), 1289-1296, "Relation of Different Measures of Low-Density Lipoprotein Cholesterol to Risk of Coronary Artery Disease and Death in a Meta Regression Analysis of Large-Scale Trials of Statin Therapy."
Kwak, E. L.; Clark, J. W.; Chabner, B., Clin, Cancer Res. 2007, 13(18), Sep. 15, 2007, 5232-5237, "Targeted Agents: The Rules of Combination."
Lane, A. A.; Chabner, B. A., J. Clin. Oncology Nov. 10, 2009, vol. 27, No. 32, 5459-5468, "Histone Deacetylase Inhibitors in Cancer Therapy."
Lin, Y. C.; Lin, J. H.; Chou, C. W.; Chang, Y. F.; Yeh, S. H.; Chen, C. C., Cancer Res. Apr. 1, 2008, 68(7), 2375-2383, "Statins Increase p21 through Inhibition of Histone Deacetylase Activity and Release of Promoter-Associated HDAC1/2."
Lipinski, C. A.; Lombardo, F.; Dominy, B. W.; Feeney, P. J., Adv. Drug Deliv. Rev. 46 (2001), pp. 3-26, "Experimental and computational approaches to estimate solubility and permeability in drug discovery and development settings."
Minden, M. D.; Dimitroulakos, J.; Nohynek, D.; Penn, L. Z., Leukemia and Lumphoma, 2001, vol. 40(5-6), pp. 659-662 "Lovastatin Induced Control of Blast Cell Growth in an Elderly Patient with Acute Myeloblastic leukemia."
Morphy, R.; Rankovic, Z., J. Med. Chem. Oct. 20, 2005, vol. 48, No. 21, 6523-6543, "Designed Multiple Ligands. An Emerging Drug Discovery Paradigm."

(56) References Cited

OTHER PUBLICATIONS

O'Boyle, N. M.; Meegan, M. J., Current Med. Chem. 2011, 18, 4722-4737, "Designed Multiple Ligands for Cancer Therapy."

Petrelli, A.; Giordano, S., Current Med. Chem. 2008, 15, 422-432, "From Single- to Multi-Target Drugs in Cancer Therapy: When Aspecificity Becomes an Advantage."

Pirali, T.; Pagliai, F.; Mercurio, C.; Boggio, R.; Canonico, P. L.; Sorba, G.; Tron, G. C.; Genazzani, A. A., J. Comb. Chem. 2008, 10, 624-627, "Triazole-Modified Histone Deacetylase Inhibitors as a Rapid Route to Drug Discovery."

Poynter, J. N.; Gruber, S. B.; Higgins, P. D.; Almog, R.; Bonner, J. D.; Rennert, H. S.; Low, M.; Greenson, J. K.; Rennert, G., New Engl. J. Med, May 26, 2005, 352, 2184-2192, "Statins and the Risk of Colorectal Cancer."

Sawyers, C. L., Nature Oct. 25, 2007, 449, 993-996, "Cancer: mixing cocktails."

Simone, C,; Peserico, A., J. Biomed. and Biotechnol. vol. 2011, Article ID 371832, 10 pages, "Physical and Functional HAT/HDAC Interplay Regulates Protein Acetylation Balance."

Shimoyama, S., Cancer Chemother. Pharmacol. 2011, 67, 729-739, "Statins are logical candidates for overcoming limitations of targeting therapies on malignancy: their potential application to gastrointestinal cancers."

Slawinska, A.; Kandefer-Szerszen, M. Postepy Hig. Med. Dosw. 2008, 62, 393-404, "The anticancer properties of statins."

Sumi, S.; Beauchamp, R. D.; Townsend, C. M., Jr.; Pour, P. M.; Ishizuka, J.; Thompson, J. C., Pancreas 1994, vol. 9, No. 5, 657-661, "Lovastatin Inhibits Pancreatic Cancer Growth Regardless of RAS Mutation."

Ward, M. M., F1000 Medicine Reports Apr. 29, 2009, 1, 35, "The JUPITER study: statins for the primary prevention of cardiovascular events in patients with inflammatory rheumatic diseases?"

Willard, A. K.; Smith, R. L., J. Labelled Compounds and Radiopharmaceuticals, 1982, vol. 19, No. 3, 337-344, "Incorporation of 2(S)-Methylbutanoic Acid-1-14C into the Structure of Mevinolin."

Witt, O.; Deubzer, H. E.; Milde, T.; Oehme, I., Cancer Lett. 277 (2009), 8-21, "HDAC-family: What are the cancer relevant targets?"

Zimmermann, G. R.; Lehár, J.; Keith, C. T., Drug Discovery Today Jan. 2007, vol. 12, Nos. 1/2, 34-42, "Multi-target therapeutics: when the whole is greater than the sum of the parts."

Chen J.B., Chern T.R., Wei T.T., Chen C.C., Lin J.H., Fang J.M., J Med Chem. May 9, 2013; 56(9):3645-55, "Design and Synthesis of Dual-Action Inhibitors Targeting Histone Deacetylases and 3-Hydroxy-3-Methylglutaryl Coenzyme A Reductase for Cancer Treatment."

Lin Y.C., Lin J.H., Chou C.W., Chang Y.F., Yeh S.H., Chen C.C., Cancer Res., Apr. 1, 2008; 68(7):2375-83, "Statins Increase p21 Through Inhibition of Histone Deacetylase Activity and Release of Promoter-Associated HDAC1/2."

\* cited by examiner

3,5,N-TRIHYDROXY-ALKANAMIDE AND DERIVATIVES: METHOD FOR MAKING SAME AND USE THEREOF

BACKGROUND OF THE INVENTION

Acetylation of lysine residues on histones H3 and H4 results in the loose and active chromatin, which allows various transcription factors to access the promoters of target genes. On the contrary, deacetylation of lysine residues results in a highly compact and transcriptionally inactive chromatin. (Jenuwein, T. & Allis, C. D. *Science* 2001, 293, 1074.) The levels of histone acetylation and deacetylation are regulated by histone acetyltransferases (HATs) and histone deacetylases (HDACs). (Peserico, A. & Simone, C. *J. Biomed. Biotechnol.* 2011, 371832.) HDAC overexpression is found in a variety of human cancers, including myeloid neoplasia and solid tumors. (Witt, O. et al. *Cancer Lett.* 2009, 277, 8.) The association of HDACs with oncogenic DNA-binding fusion proteins or other repressive transcription factors leads to constitutive suppression of specific tumor suppressor genes. (Bolden, J. E. et al. *Nature Rev. Drug Discovery* 2006, 5, 769.) Therefore, HDACs represent a potential target for cancer treatment.

Statins can reduce serum cholesterol levels through competitively inhibiting 3-hydroxy-3-methylglutaryl coenzyme A (HMG-CoA) reductase (HMGR), the rate-limiting enzyme in cholesterol biosynthesis. This effect contributes to their decrease in the incidence of cardiovascular and cerebrovascular disorders, and their remarkable prevention of cardiovascular disease (CVD). (Ward, M. M. F1000 Medicine Reports 2009, 1, 35. Kapur, N. K. Expert Rev. Cardiovasc. Ther. 2007, 5, 161.) Statins possess an established record of human safety and efficacy in CVD prevention and also show promise for cancer prevention in observational, preclinical, and certain aspects of randomized controlled studies. (Hawk, E. & Viner, J. L. *New Engl. J. Med.* 2005, 352, 2238.) Statins also exhibit antitumor activity as shown in both in vitro proliferation and in vivo xenograft model. (Lin, Y. C. et al. *Cancer Res.* 2008, 68, 2375.)

Combinations of HDAC inhibitors with cytotoxic agents, or targeted anti-cancer drugs have been reported to improve the outcome of cancer treatment in several pre-clinical research and clinical trials. (Lane, A. A. & Chabner, B. A. *J. Clin. Oncology* 2009, 27, 5459.)

Histone deacetylases (HDACs) represent a potential target for cancer treatment, whereas statins can inhibit 3-hydroxy-3-methylglutaryl coenzyme A reductase (HMGR) to reduce serum cholesterol levels.

SUMMARY OF THE INVENTION

The present disclosure is based on the unexpected discoveries that certain hexanohydroxamic acid derivative compounds (e.g., Lova-HA, Simva-HA, Atorva-HA, Rosuva-HA, corresponding to Compounds 1, 2, 5, and 7, respectively) are more effective in inhibiting the growth of cancer cells, via, e.g., inhibiting the activity of HDAC and/or HMGR, and less toxic as compared to lovastatin, trichostatin A, and suberoylanalide hydroxamic acid. Further, the hexanohydroxamic acid derivative compounds are found not to induce drug resistance particularly under hypoxia conditions. As such, those hexanohydroxamic acid derivative compounds as described herein can be used in treating cancer, as well as other diseases associated with HDAC and/or HMGR.

In one aspect, the present disclosure provides compounds of Formula (I):

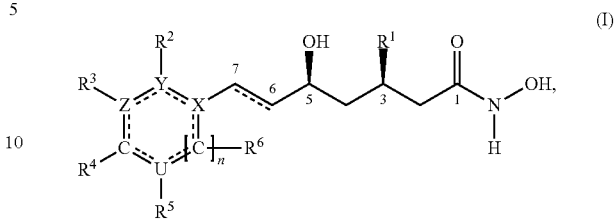

and pharmaceutically acceptable salts thereof
wherein:

n is 0 or 1;

X, Y, Z, and U are independently selected from the group consisting of carbon and nitrogen;

==== represents a single or double bond;

$R^1$, $R^2$, $R^3$, $R^4$, $R^5$, and $R^6$ are independently selected from the group consisting of null, H, $C_{1-6}$ alkyl, alkenyl, alkynyl, fluoroalkyl, chloroalkyl, bromoalkyl, iodoalkyl, perfluoroalkyl, aryl, heteroaryl, cycloalkyl, cycloalkenyl, aralkyl, aralkenyl, aralkynyl, heteroaralkyl, heteroaralkenyl, heteroaralkynyl, heterocyclyl, acyl, aminocarbonyl, amino, hydroxyl, alkoxy, acyloxy, silyloxy, amido, carbamoyl, and sulfonamido; and $R^3$ is optionally connected with $R^2$ or $R^4$ to form carbocycle or heterocycle.

In certain embodiments, X can be carbon; and Y, Z, and U are carbon or nitrogen; with the proviso that the bond between C6 and C7 can be a double bond when Y is carbon and both Z and U are nitrogen.

In certain embodiments, the compound of Formula (I) can be 5,N-dihydroxyalkanamide derivative of Formula (III):

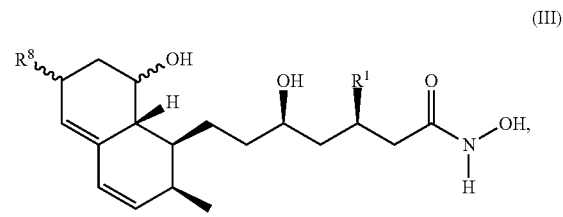

or a pharmaceutically acceptable salt thereof
wherein:

$R^1$ is selected from the group consisting of $C_{1-6}$ alkyl, alkenyl, alkynyl, fluoroalkyl, chloroalkyl, bromoalkyl, iodoalkyl, perfluoroalkyl, aryl, heteroaryl, cycloalkyl, cycloalkenyl, aralkyl, aralkenyl, aralkynyl, heteroaralkyl, heteroaralkenyl, heteroaralkynyl, heterocyclyl, acyl, aminocarbonyl, amino, hydroxyl, alkoxy, acyloxy, silyloxy, amido, carbamoyl, and sulfonamido;

$R^7$ is selected from the group consisting of H, acyl, $C_{1-6}$alkyl, alkenyl, alkynyl, and aralkyl; and $R^8$ is selected from the group consisting of H, methyl, and hydroxyl.

In certain embodiments, the compound of Formula (III) can be

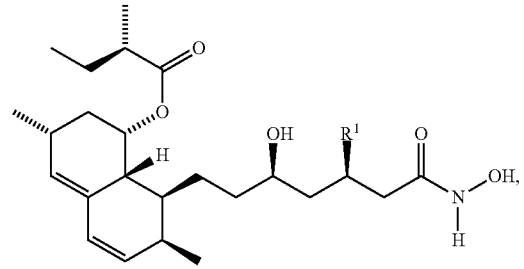

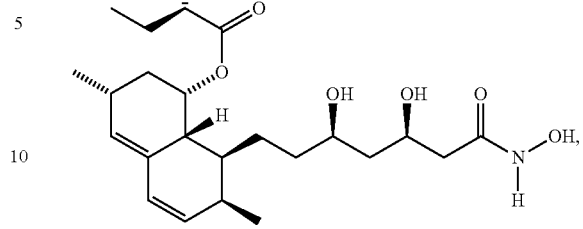
Lova-HA,

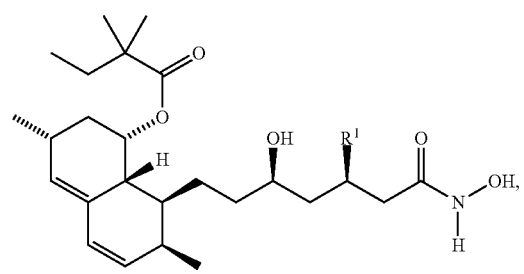

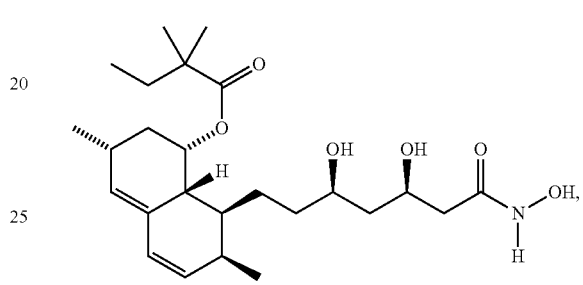
Simva-HA,

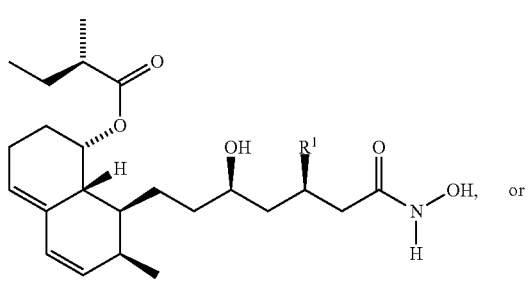 or

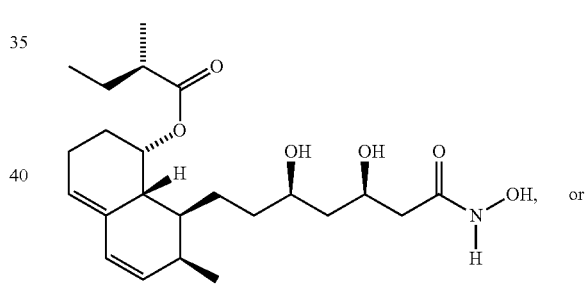 or
Meva-HA,

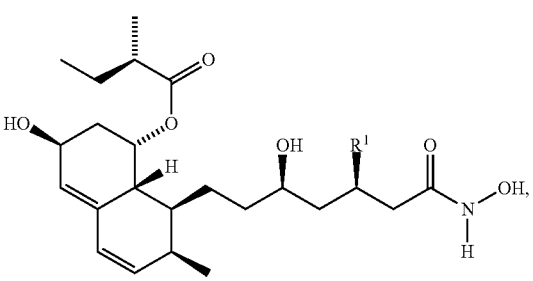

or a pharmaceutically acceptable salt thereof wherein $R^1$ is selected from the group consisting of $C_{1-6}$ alkyl, alkenyl, alkynyl, fluoroalkyl, chloroalkyl, bromoalkyl, iodoalkyl, perfluoroalkyl, aryl, heteroaryl, cycloalkyl, cycloalkenyl, aralkyl, aralkenyl, aralkynyl, heteroaralkyl, heteroaralkenyl, heteroaralkynyl, heterocyclyl, acyl, aminocarbonyl, amino, hydroxyl, alkoxy, acyloxy, silyloxy, amido, carbamoyl, and sulfonamido.

In certain embodiments, the compound of Formula (III) can be a 3,5,N-trihydroxy-alkanamide derivative of:

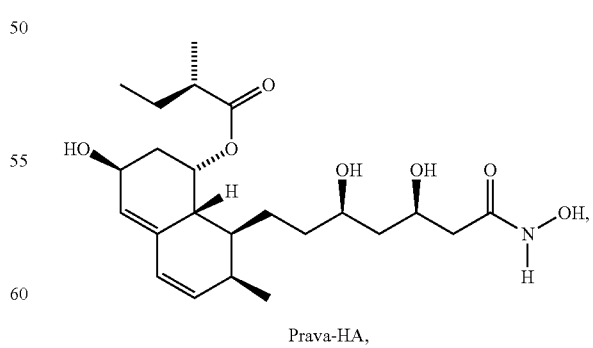
Prava-HA, or a pharmaceutically acceptable salt thereof.

In certain embodiments, the compound of Formula (III) can be a 3-O-(p-methoxybenzyl) derivative of the formula:

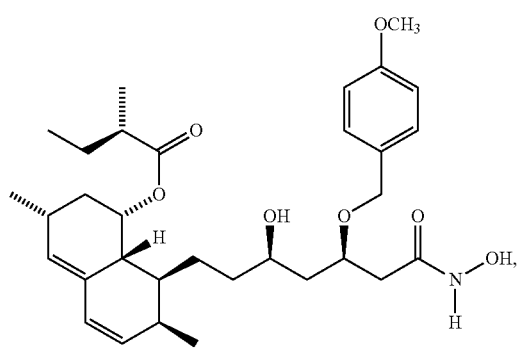

3-PMB-Lova-HA,

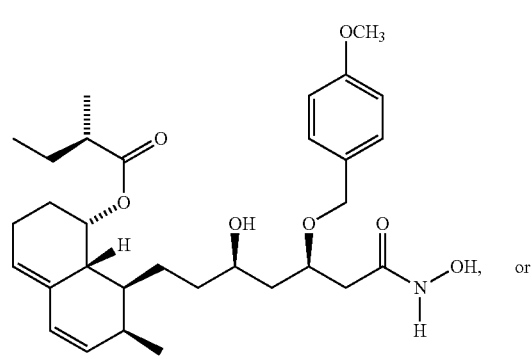

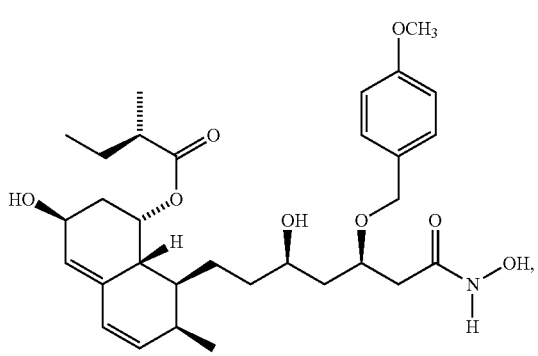

or a pharmaceutically acceptable salt thereof.

In certain embodiments, the compound of Formula (I) can be of any one of formulas (V), (VII), and (VIII):

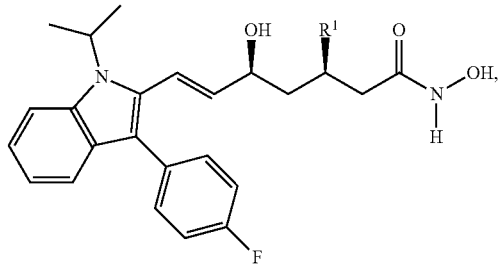

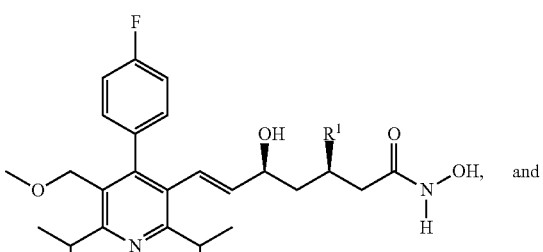

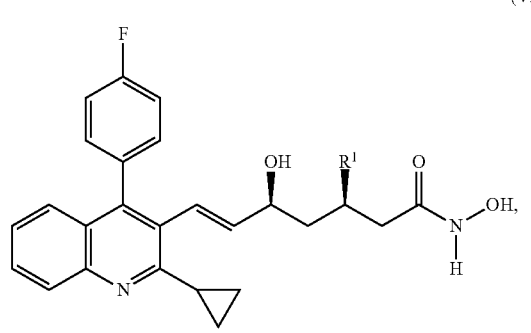

or a pharmaceutically acceptable salt thereof; wherein $R^1$ is selected from the group consisting of $C_{1-6}$ alkyl, alkenyl, alkynyl, fluoroalkyl, chloroalkyl, bromoalkyl, iodoalkyl, perfluoroalkyl, aryl, heteroaryl, cycloalkyl, cycloalkenyl, aralkyl, aralkenyl, aralkynyl, heteroaralkyl, heteroaralkenyl, heteroaralkynyl, heterocyclyl, acyl, aminocarbonyl, amino, hydroxyl, alkoxy, acyloxy, silyloxy, amido, carbamoyl, and sulfonamido.

In certain embodiments, the compound of Formula (I) can be a 3,5,N-trihydroxy-6-alkenamide derivative of the formula:

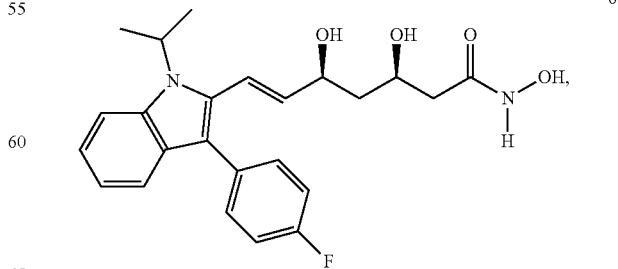

Fluva-HA,

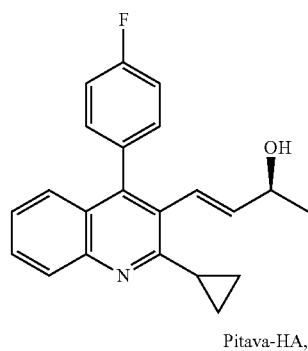

Pitava-HA,

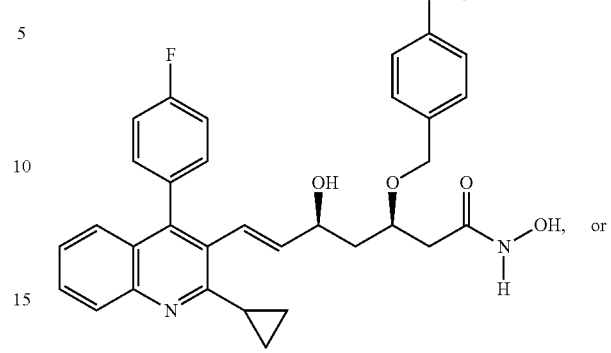

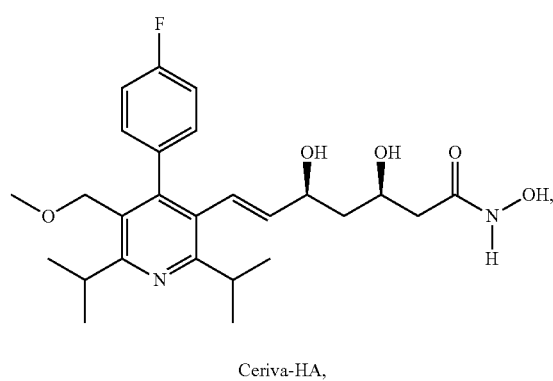

Ceriva-HA, or a pharmaceutically acceptable salt thereof.

In certain embodiments, the compound of Formula (I) can be a p-methoxybenzyl derivative of the formula:

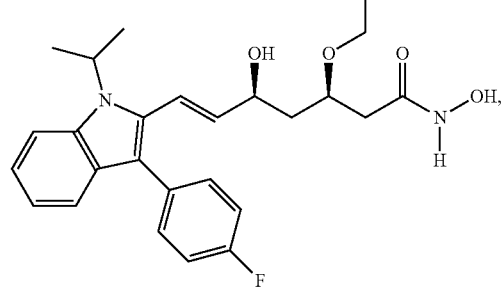

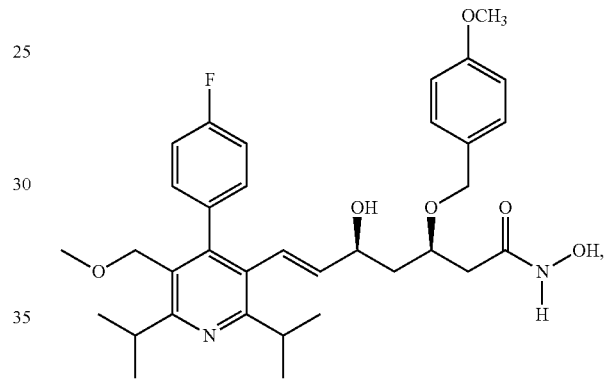

or a pharmaceutically acceptable salt thereof.

In certain embodiments, the compound of Formula (I) can be of Formula (IV):

(IV)

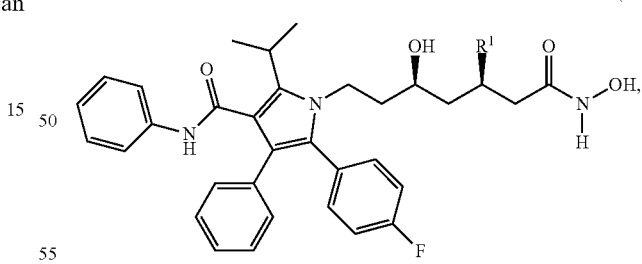

or a pharmaceutically acceptable salt thereof; wherein $R^1$ is selected from the group consisting of $C_{1-6}$ alkyl, alkenyl, alkynyl, fluoroalkyl, chloroalkyl, bromoalkyl, iodoalkyl, perfluoroalkyl, aryl, heteroaryl, cycloalkyl, cycloalkenyl, aralkyl, aralkenyl, aralkynyl, heteroaralkyl, heteroaralkenyl, heteroaralkynyl, heterocyclyl, acyl, aminocarbonyl, amino, alkoxy, acyloxy, silyloxy, amido, carbamoyl, and sulfonamido.

In certain embodiments, the compound of Formula (IV) can be a 3-O-(p-methoxybenzyl) derivative of the formula:

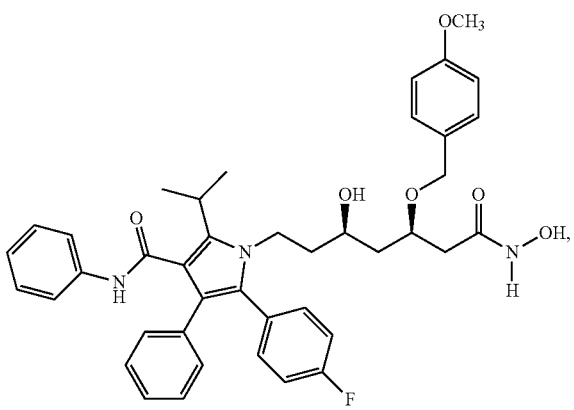

3-PMB-Atorva-HA, or a pharmaceutically acceptable salt thereof.

In certain embodiments, the compound of Formula (I) can be of Formula (VI):

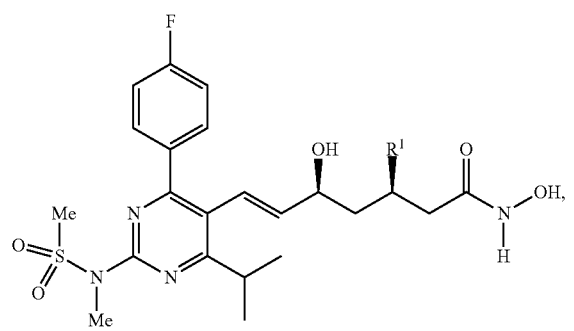

(VI)

or a pharmaceutically acceptable salt thereof wherein $R^1$ is selected from the group consisting of $C_{1-6}$ alkyl, alkenyl, alkynyl, fluoroalkyl, chloroalkyl, bromoalkyl, iodoalkyl, perfluoroalkyl, aryl, heteroaryl, cycloalkyl, cycloalkenyl, aralkyl, aralkenyl, aralkynyl, heteroaralkyl, heteroaralkenyl, heteroaralkynyl, heterocyclyl, acyl, aminocarbonyl, amino, hydroxyl, alkoxy, acyloxy, silyloxy, amido, carbamoyl, and sulfonamido.

In certain embodiments, the compound of Formula (VI) can be a 3,5,N-trihydroxy-6-alkenamide derivative of the formula:

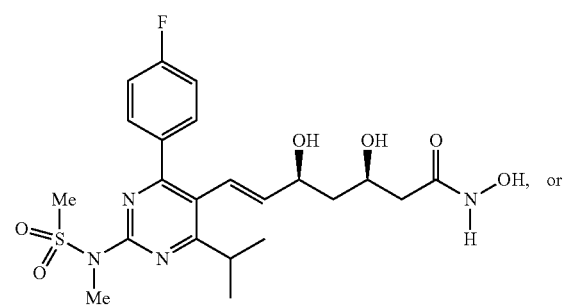

Rosuva-HA, or a pharmaceutically acceptable salt thereof.

In certain embodiments, n is 0 or 1.

Alternatively or in addition, U can be carbon or nitrogen; Y can be carbon or nitrogen, and/or both X and Z can be carbon.

In certain embodiments, $R^1$ can be hydroxyl or alkoxy. In other embodiments, $R^1$ can be of the formula:

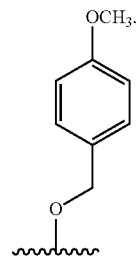

In certain embodiments, $R^2$ can be $C_{1-6}$ alkyl (e.g., isopropyl) or aryl (e.g., para-fluorophenyl). In other embodiments, $R^2$ can be connected with $R^3$ to form carbocycle or cyclohexenyl.

In certain embodiments, $R^3$ can be null, $C_{1-6}$ alkyl (e.g., methoxymethyl), or aminocarbonyl (e.g., —C(=O)NHPh). In other embodiments, $R^3$ can be connected with $R^2$ or $R^4$ to form carbocycle or heterocycle, e.g., $R^3$ is connected with $R^4$ to form carbocycle or phenyl.

In certain embodiments, $R^4$ can be $C_{1-6}$ alkyl (e.g., isopropyl), aryl (e.g., phenyl), or sulfonamido (e.g.,

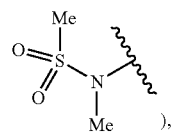), or $R^4$ can be connected with $R^3$ to form carbocycle.

In certain embodiments, $R^5$ can be null, H, or aryl (e.g., para-fluorophenyl).

In certain embodiments, $R^6$ can be $C_{1-6}$ alkyl (e.g., methyl or isopropyl) or cycloalkyl (e.g., cyclopropyl).

In certain embodiments, $R^7$ can be acyl (eg:

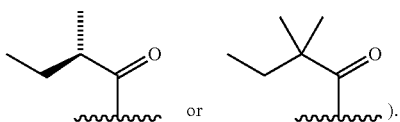

).

In certain embodiments, $R^8$ can be H, methyl, or hydroxyl.

Another aspect of the present invention relates to methods for manufacturing a compound of Formula (I), or a pharmaceutically acceptable salt thereof, the method comprising contacting a compound of Formula (II), or a salt thereof, with hydroxylamine, or a salt thereof:

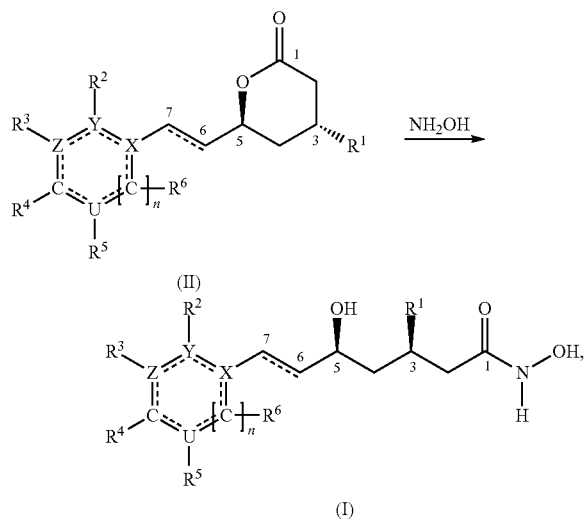

wherein:
n is 0 or 1;
U, X, Y, and Z are independently selected from the group consisting of carbon and nitrogen;
═══ represents a single or double bond;
$R^1$, $R^2$, $R^3$, $R^4$, $R^5$ and $R^6$ are independently selected from the group consisting of $C_{1-6}$ alkyl, alkenyl, alkynyl, fluoroalkyl, chloroalkyl, bromoalkyl, iodoalkyl, perfluoroalkyl, aryl, heteroaryl, cycloalkyl, cycloalkenyl, aralkyl, aralkenyl, aralkynyl, heteroaralkyl, heteroaralkenyl, heteroaralkynyl, heterocyclyl, acyl, aminocarbonyl, amino, hydroxyl, alkoxy, acyloxy, silyloxy, amido, carbamoyl, and sulfonamido; and
$R^3$ is optionally connected with $R^2$ or $R^4$ to form carbocycle or heterocycle.

In certain embodiments, X can be carbon; and Y, Z, and U can independently be carbon or nitrogen; with the proviso that the bond between C6 and C7 can be a double bond when Y is carbon and both Z and U are nitrogen. In certain embodiments, the hydroxylamine can be in solution or can be generated in situ by contacting a salt of hydroxylamine with a base. In certain embodiments, the salt can be a hydrochloride, nitrate, phosphate, or sulfate salt. In certain embodiments, the base can be hydroxide, carbonate, bicarbonate, methoxide, ethoxide, isopropoxide, or tert-butoxide with the counter cation being lithium, sodium, potassium, cesium, calcium, or barium. In certain embodiments, a Lewis acid can be used as a reaction promotor, wherein the Lewis acid can be lithium, magnesium, calcium, zinc, aluminum, boron, indium, scandium, ytterbium, cerium, silicon, tin, titanium, zirconium, vanadium, iron, or cobalt salts with the counter anion being fluoride, chloride, bromide, iodide, hydroxide, methoxide, ethoxide, isoproproxide, tert-butoxide, acetate, oxalate, acetylacetonate, nitrate, phosphate, sulfate, bisulfate, or sulfonate. In certain embodiments, the step of contacting can be conducted in a hydrocarbon, ethereal, chlorinated, or alcoholic solvent, or a mixture thereof. In certain embodiments, the hydrocarbon solvent can be an acyclic, cyclic, or aromatic solvent (e.g., n-hexane, cyclohexane, benzene, toluene, or xylene). In certain embodiments, the ethereal solvent can be an acyclic or cyclic solvent (e.g., diethyl ether, methyl tert-butyl ether, dimethoxyethane, tetrahydrofuran, or 1,4-dioxane).

In another aspect, the present disclosure provides pharmaceutical compositions comprising one or more of the compounds described herein, or a pharmaceutically acceptable salt thereof, and a pharmaceutically acceptable excipient.

In yet another aspect, the present disclosure provides methods for treating cancer, the methods comprising administering to a subject in need thereof a therapeutically effective amount of any of the pharmaceutical compositions described herein.

In certain embodiments, the cancer can be leukemia, Hodgkin's disease, lymphoma, Ewing's sarcoma, multiple myeloma, Wilms' tumor, bone tumor, neuroblastoma, retinoblastoma, testicular cancer, thyroid cancer, prostate cancer, larynx cancer, cervical cancer, nasopharynx cancer, breast cancer, colon cancer, pancreatic cancer, head and neck cancer, esophageal cancer, rectal cancer, small-cell lung cancer, non-small-cell lung cancer, brain cancer, melanoma and other skin cancers, or CNS neoplasm.

In still another aspect, the present disclosure provides methods for treating hypercholesterolemia, the methods comprising administering to a subject in need thereof an therapeutically effective amount of any of the pharmaceutical compositions described herein.

In addition, the present disclosure provides methods for treating an acute or chronic inflammatory disease, autoimmune disease, allergic disease, pathogen infection, neurodegenerative disease, or a disease associated with oxidative stress. Such a method comprises administering to a subject in need thereof an therapeutically effective amount of any of the pharmaceutical compositions described herein of the invention.

In certain embodiments, the subject being treated in any of the treatment methods described herein can be a human, such as a human patient having, suspected of having, or at risk for the target disease as described herein.

In another aspect, the present disclosure provides methods for inhibiting the drug resistance of a cancer cell, the methods comprising contacting said cell with an effective amount of any of the pharmaceutical compositions described herein. In certain embodiments, the contacting step is performed by administering an effective amount of the pharmaceutical composition to a subject in need of the treatment.

In yet another aspect, the present invention provides pharmaceutical compositions for use in treating cancer, hypercholesterolemia, an acute or chronic inflammatory disease, autoimmune disease, allergic disease, pathogen infection, neurodegenerative disease, or a disease associated with oxidative stress, or reducing drug resistance (e.g., resistance to Oxaliplatin) of cancer cells (e.g., colorectal cancer cells), wherein the pharmaceutical composition comprises one or more of the compounds described herein, or a pharmaceutically acceptable salt thereof, and a pharmaceutically acceptable excipient.

Also within the scope of the present disclosure is the use of any of the compounds described herein for the manufacture of a medicament for the treatment of any of the target diseases described herein.

The details of one or more embodiments of the invention are set forth in the description below. Other features or advantages of the present invention will be apparent from the following drawings and detailed description of several embodiments, and also from the appended claims.

DEFINITIONS

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw Hill, N.Y., 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

When a range of values is listed, it is intended to encompass each value and sub range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "aliphatic" includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and cyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, cyclopropyl, —$CH_2$-cyclopropyl, vinyl, allyl, n-butyl, sec-butyl, isobutyl, tert-butyl, cyclobutyl, —$CH_2$-cyclobutyl, n-pentyl, sec-pentyl, isopentyl, tert-pentyl, cyclopentyl, —$CH_2$-cyclopentyl, n-hexyl, sec-hexyl, cyclohexyl, —$CH_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_2$ 6 alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl," "carbocycle," or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged, or spiro ring system such as a bicyclic system ("bicyclic carbocyclyl"). Carbocyclylcan be saturated, and saturated carbocyclyl is referred to as "cycloalkyl." In some embodiments, carbocyclyl is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_3$ 8 cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl. Carbocyclyl can be partially unsaturated. Carbocyclyl including one or more C=C double bond in the carbocyclic ring is referred to as "cycloalkenyl." Carbocyclyl including one or more C≡C triple bond in the carbocyclic ring is referred to as "cycloalkynyl." Carbocyclyl includes aryl. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is substituted $C_{3-10}$ carbocyclyl.

"Heterocyclyl," "heterocycle," or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system, such as a bicyclic system ("bicyclic heterocyclyl"), and can be saturated or can be partially unsaturated. Heterocyclyl bicyclic ring systems can include one or more heteroatoms in one or both rings. Heterocyclyl includes heteroaryl. Heterocyclyl also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl, as defined herein, and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Aralkenyl" is a subset of alkenyl and aryl, as defined herein, and refers to an optionally substituted alkenyl group substituted by an optionally substituted aryl group. An example of aralkenyl is styrenyl (i.e., —CH═CHPh).

"Aralkynyl" is a subset of alkynyl and aryl, as defined herein, and refers to an optionally substituted alkynyl group substituted by an optionally substituted aryl group.

"Heteroaryl" refers to a radical of a 5-10 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl, as defined herein, and refers to an optionally substituted alkyl group substituted by an optionally substituted heteroaryl group.

"Heteroaralkenyl" is a subset of alkenyl and heteroaryl, as defined herein, and refers to an optionally substituted alkenyl group substituted by an optionally substituted heteroaryl group.

"Heteroaralkynyl" is a subset of alkynyl and heteroaryl, as defined herein, and refers to an optionally substituted alkynyl group substituted by an optionally substituted heteroaryl group.

"Halo" or "halogen" refers to fluorine (fluoro, —F), chlorine (chloro, —Cl), bromine (bromo, —Br), or iodine (iodo, —I).

The term "haloalkyl" denotes an alkyl group, as defined above, having one, two, three, four, five, six, or more halogen atoms attached thereto. Haloalkyl includes fluoroalkyl, chloroalkyl, bromoalkyl, and iodoalkyl. "Fluoroalkyl" refers to an alkyl group having one, two, three, four, five, six, or more fluorine atoms attached thereto. "Perfluoroalkyl" refers to a fluoroalkyl group that only includes carbon and fluorine atoms. "Chloroalkyl" refers to an alkyl group having one, two, three, four, five, six, or more chlorine atoms attached thereto. "Bromoalkyl" refers to an alkyl group having one, two, three, four, five, six, or more bromine atoms attached thereto. "Iodoalkyl" refers to an alkyl group having one, two, three, four, five, six, or more iodine atoms attached thereto. A haloalkyl group may include more than one type of halogen atoms. For example, fluoroalkyl includes an alkyl group having one or more fluorine atoms and one or more chlorine atoms. A haloalkyl group may be substituted with one or more substituents that are not halogen atoms.

"Acyl" refers to a moiety selected from the group consisting of —C(=O)$R^{aa}$, —CHO, —$CO_2R^{aa}$, —C(=O)N($R^{bb}$)$_2$, —C(=$NR^{bb}$)$R^{aa}$, —C(=$NR^{bb}$)O$R^{aa}$, —C(=$NR^{bb}$)N($R^{bb}$)$_2$, —C(=O)$NR^{bb}SO_2R^{aa}$, —C(=S)N($R^{bb}$)$_2$, —C(=O)S$R^{aa}$, or —C(=S)S$R^{aa}$, wherein $R^{aa}$ and $R^{bb}$ are as defined herein.

The term "aminocarbonyl" refers to a moiety of the formula: —C(=O)N($R^{hh}$)$_2$, wherein each instance of $R^{hh}$ is independently a nitrogen atom substituent described herein, or two instances of $R^{hh}$ are connected to form substituted or unsubstituted heterocyclyl. In certain embodiments, the aminocarbonyl is unsubstituted aminocarbonyl (i.e., —C(=O)NH$_2$). In certain embodiments, the aminocarbonyl is a substituted aminocarbonyl group, wherein at least one instance of $R^{hh}$ is not hydrogen.

The term "amino" refers to a moiety of the formula: —N($R^{ii}$)$_2$, wherein each instance of $R^{ii}$ is independently a nitrogen atom substituent described herein, or two instances of $R^{ii}$ are connected to form substituted or unsubstituted heterocyclyl. In certain embodiments, the amino is unsubstituted amino (i.e., —NH$_2$). In certain embodiments, the amino is a substituted amino group, wherein at least one instance of $R^{ii}$ is not hydrogen.

The term "hydroxyl" or "hydroxy" refers to a moiety of the formula: —O$R^{jj}$, wherein $R^{jj}$ is an oxygen atom substituent described herein. In certain embodiments, the hydroxyl is unsubstituted hydroxyl (i.e., —OH). In certain embodiments, the hydroxyl is a substituted hydroxyl group, wherein $R^{jj}$ is not hydrogen.

The term "alkoxy" refers to a moiety of the formula: —O$R^{kk}$, wherein $R^{kk}$ is an optionally substituted alkyl group described herein.

The term "acyloxy" refers to a moiety of the formula: —OC(=O)$R^{mm}$, wherein $R^{mm}$ is a carbon atom substituent described herein. In certain embodiments, the acyloxy is unsubstituted acyloxy (i.e., —OC(=O)H). In certain embodiments, the acyloxy is a substituted acyloxy group, wherein $R^{mm}$ is not hydrogen.

The term "silyloxy" refers to a moiety of the formula: —OSi($R^{nn}$)$_3$, wherein each instance of $R^{nn}$ is independently a silicon atom substituent described herein.

The term "amido" refers to a moiety of the formula: —N($R^{pp}$)C(=O)$R^{qq}$, wherein $R^{pp}$ is a nitrogen atom substituent described herein, and Ran is a carbon atom substituent described herein.

The term "carbamoyl" refers to a moiety of the formula: —OC(=O)N($R^{rr}$)$_2$, wherein each instance of $R^{rr}$ is independently a nitrogen atom substituent described herein. In certain embodiments, the carbamoyl is unsubstituted carbamoyl (i.e., —OC(=O)NH$_2$). In certain embodiments, the carbamoyl is substituted carbamoyl, wherein at least one instance of $R^{rr}$ is not hydrogen.

The term "sulfonamido" refers to a moiety of the formula: —N($R^{ss}$)S(=O)$_2R^{tt}$, wherein $R^{ss}$ is a nitrogen atom substituent described herein, and $R^{tt}$ is a sulfur atom substituent described herein.

"Unsaturated" or "partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

Alkyl, alkenyl, alkynyl, carbocyclyl, heterocyclyl, aryl, and heteroaryl groups, as defined herein, which are divalent bridging groups are further referred to using the suffix -ene, e.g., alkylene, alkenylene, alkynylene, carbocyclylene, heterocyclylene, arylene, and heteroarylene.

An atom, moiety, or group described herein may be unsubstituted or substituted, as valency permits, unless otherwise provided expressly. The term "optionally substituted" refers to substituted or unsubstituted.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. In certain embodiments, the substituent is a carbon atom substituent. In certain embodiments, the substituent is a nitrogen atom substituent. In certain embodiments, the substituent is an oxygen atom substituent. In certain embodiments, the substituent is a sulfur atom substituent. In certain embodiments, the substituent is a silicon atom substituent.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR—, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O) (NR$^{bb}$)$_2$, NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{ii}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups; or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$) OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NRCO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, C(=NR$^{ff}$)N(R$^{ff}$)$_2$, —OC(=NR$^{ff}$) N(R$^{ff}$)$_2$, —NR$^{ff}$C(=NR$^{ff}$)N(R$^{ff}$)$_2$, —NR$^{ff}$SO$_2$R$^{ee}$, —SO$_2$N (R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O) (R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl) X$^-$, —NH$_3$$^+$X$^-$, —N(OC$_{1-6}$ alkyl)(C$_{1-6}$ alkyl), —N(OH)(C$_{1-6}$ alkyl), —NH (OH), —SH, —SC$_{1-6}$ alkyl, —SS(C$_{1-6}$ alkyl), —C(=O) (C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N (C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC (=NH)(C$_{1-6}$ alkyl), —OC(=NH)OC$_{1-6}$ alkyl, —C(=NH)N (C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC (=NH)NH$_2$, —NHSO$_2$(C$_{1-6}$ alkyl), —SO$_2$N(C$_{1-6}$ alkyl)$_2$, —SO₂NH(C₁₋₆ alkyl), —SO₂NH₂, —SO₂C₁₋₆ alkyl, —SO₂OC₁₋₆ alkyl, —OSO₂C₁₋₆ alkyl, —SOC₁₋₆ alkyl, —Si(C₁₋₆ alkyl)₃, —OSi(C₁₋₆ alkyl)₃-C(=S)N(C₁₋₆ alkyl)₂, C(=S)NH(C₁₋₆ alkyl), C(=S)NH₂, —C(=O)S(C₁₋₆ alkyl), —C(=S)SC₁₋₆ alkyl, —SC(=S)SC₁₋₆ alkyl, —P(=O)₂(C₁₋₆ alkyl), —P(=O)(C₁₋₆ alkyl)₂, —OP(=O)(C₁₋₆ alkyl)₂, —OP(=O)(OC₁₋₆ alkyl)₂, C₁₋₆ alkyl, C₁₋₆ perhaloalkyl, C₂₋₆ alkenyl, C₂₋₆ alkynyl, C₃₋₁₀ carbocyclyl, C₆₋₁₀ aryl, 3-10 membered heterocyclyl, 5-10 membered heteroaryl; or two geminal RES substituents can be joined to form =O or =S; wherein X⁻ is a counterion.

A "counterion" or "anionic counterion" is a negatively charged group associated with a cationic quaternary amino group in order to maintain electronic neutrality. Exemplary counterions include halide ions (e.g., F⁻, Cl⁻, Br⁻, I⁻), NO₃⁻, ClO₄⁻, OH⁻, H₂PO₄⁻, HSO₄⁻, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)₂, —CN, —C(=O)R$^{aa}$, —C(=O)N(R$^{cc}$)₂, —CO₂R$^{aa}$, —SO₂R$^{aa}$, —C(=NR$^{bb}$)R$^{aa}$, —C(=NR$^{cc}$)OR$^{aa}$, —C(=NR$^{cc}$)N(R$^{cc}$)₂, —SO₂N(R$^{cc}$)₂, —SO₂R$^{cc}$, —SO₂OR$^{cc}$, —SOR$^{aa}$, —C(=S)N(R$^{cc}$)₂, —C(=O)SR$^{cc}$, —C(=S)SR$^{cc}$, —P(=O)₂R$^{aa}$, —P(=O)(R$^{aa}$)₂, —P(=O)₂N(R$^{cc}$)₂, —P(=O)(NR$^{cc}$)₂, C₁₋₁₀ alkyl, C₁₋₁₀ perhaloalkyl, C₂₋₁₀ alkenyl, C₂₋₁₀ alkynyl, C₃₋₁₀ carbocyclyl, 3-14 membered heterocyclyl, C₆₋₁₄ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$, and R$^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{c}$)₂, —C(=O)R$^{aa}$, —C(=O)N(R$^{cc}$)₂, —CO₂R$^{aa}$, —SO₂R$^{aa}$, —C(=NR$^{cc}$)R$^{aa}$, —C(=NR)OR$^{aa}$, —C(=NR$^{cc}$)N(R$^{cc}$)₂, —SO₂N(R$^{cc}$)₂, —SO₂R$^{cc}$, —SO₂OR$^{cc}$, —SOR$^{aa}$, —C(=S)N(R$^{cc}$)₂, —C(=O)SR$^{cc}$, —C(=S)SR$^{cc}$, C₁₋₁₀ alkyl (e.g., aralkyl, heteroaralkyl), C₂₋₁₀ alkenyl, C₂₋₁₀ alkynyl, C₃₋₁₀ carbocyclyl, 3-14 membered heterocyclyl, C₆₋₁₄ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl) propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)₂R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4- methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilyl ethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

Exemplary oxygen atom substituents include, but are not limited to, —$R^{aa}$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. In certain embodiments, the oxygen atom substituent present on an oxygen atom is an oxygen protecting group (also referred to as a hydroxyl protecting group). Oxygen protecting groups are well known in the art and include those described in detail in *Protecting Groups in Organic Synthesis*, T. W. Greene and P. G. M. Wuts, $3^{rd}$ edition, John Wiley & Sons, 1999, incorporated herein by reference. Exemplary oxygen protecting groups include, but are not limited to, methyl, t-butyloxycarbonyl (BOC or Boc), methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran 2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio)ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

Exemplary sulfur atom substituents include, but are not limited to, —$R^{aa}$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. In certain embodiments, the sulfur atom substituent present on a sulfur atom is a sulfur protecting group (also referred to as a thiol protecting group). Sulfur protecting groups are well known in the art and include those described in detail in *Protecting Groups in Organic Synthesis*, T. W. Greene and P. G. M. Wuts, 3rd edition, John Wiley & Sons, 1999, incorporated herein by reference.

Exemplary silicon atom substituents include, but are not limited to, —$R^{aa}$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR$ $C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. In certain embodiments, the silicon atom substituent present on a silicon atom is a silicon protecting group (also referred to as a silyl protecting group). Silicon protecting groups are well known in the art and include those described in detail in *Protecting Groups in Organic Synthesis*, T. W. Greene and P. G. M. Wuts, 3rd edition, John Wiley & Sons, 1999, incorporated herein by reference.

The present disclosure is not intended to be limited in any manner by the above exemplary listing of substituents.

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-6}\text{ alkyl})_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound which is associated with water. Typically, the number of the water molecules contained in a hydrate of a compound is in a definite ratio to the number of the compound molecules in the hydrate. Therefore, a hydrate of a compound may be represented, for example, by the general formula $R \cdot x\ H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates ($R \cdot 0.5\ H_2O$)), and polyhydrates (x is a number greater than 1, e.g., dihydrates ($R \cdot 2\ H_2O$) and hexahydrates ($R \cdot 6\ H_2O$)).

The term "tautomers" or "tautomeric" refers to two or more interconvertable compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers".

When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refer to compounds, including derivatives of the compounds described herein, which have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds of this invention have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds of this invention are particular prodrugs. In some cases it is desirable to prepare double ester type prodrugs such as (acyloxy)alkyl esters or ((alkoxycarbonyl)oxy) alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

Unless otherwise defined, all technical and scientific terms have the same meaning as commonly understood by one of ordinary skill in the art to which this invention pertains. In the case of conflict, the present document, including definitions will control.

BRIEF DESCRIPTION OF THE DRAWINGS

The following drawings form part of the present specification and are included to further demonstrate certain aspects of the present disclosure, the inventions of which can be better understood by reference to one or more of these drawings in combination with the detailed description of specific embodiments presented herein. The patent or application file contains at least one drawing executed in color. Copies of this patent or patent application publication with color drawing(s) will be provided by the Office upon request and payment of the necessary fee.

DETAILED DESCRIPTION OF CERTAIN EMBODIMENTS OF THE INVENTION

Figures 1A, 1B:
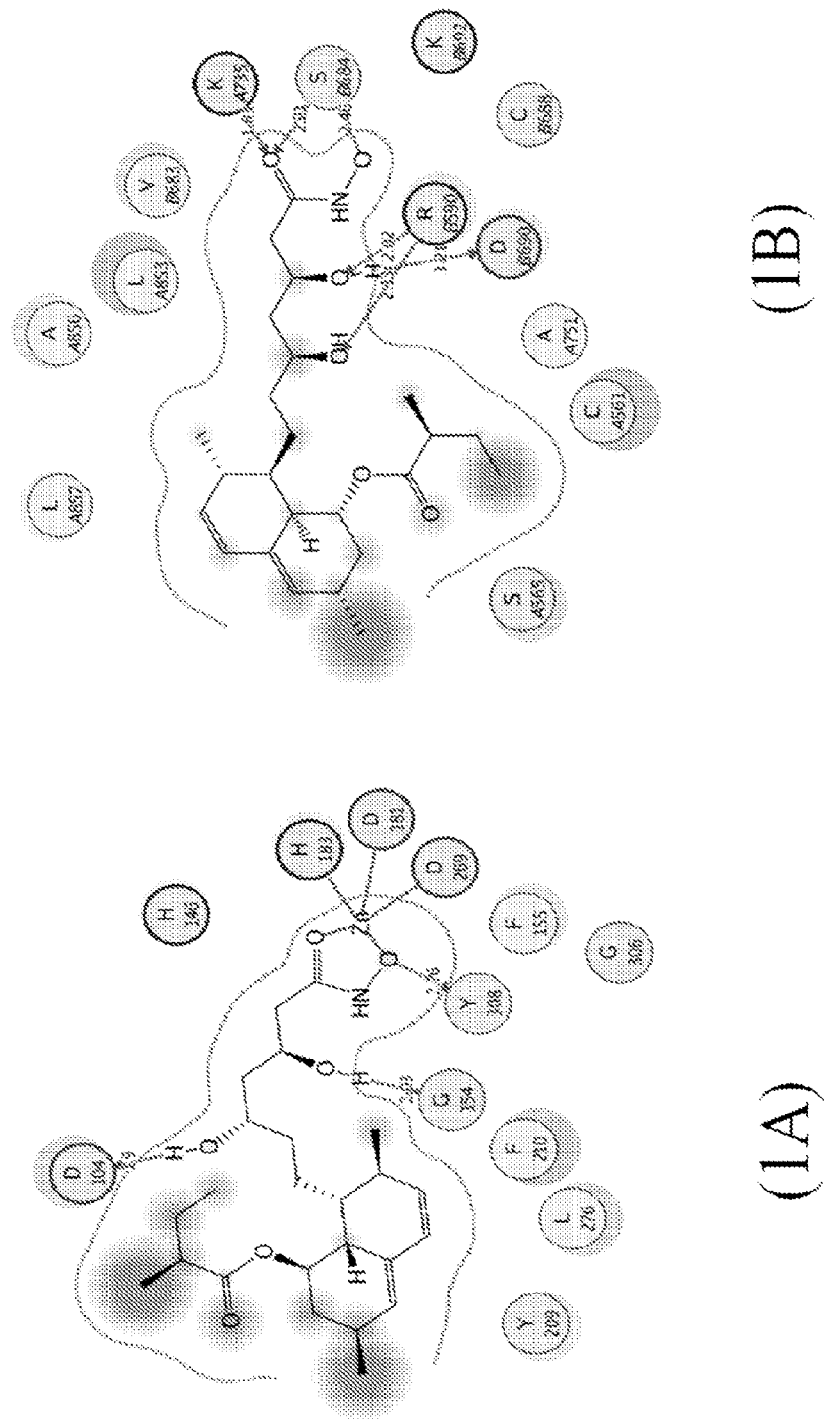
FIG. 1 is a diagram showing receptor-ligand interaction. (1A) and (1B) illustrate the key interactions of Lova-HA with HDAC2 and HMG-CoA reductase, respectively. (1C) and (1D) illustrate the key interactions of Simva-HA with HDAC2 and HMG-CoA reductase, respectively. (1E) and (1F) illustrate the key interactions of Atorva-HA with HDAC2 and HMG-CoA reductase, respectively. Amino acid residues within 4.5 Å of Lova-HA are presented in the two-dimensional interaction diagram. The blue circle on the ligand (Lova-HA, Simva-HA or Atorva-HA) represents its exposure to the solvent. The larger circle indicates more exposure of the ligand to solvent. The green and magenta dashed lines represent hydrogen bonding and metal chelation, respectively.

Described herein are novel hexanohydroxamic acid derivative compounds having the structures as set forth herein, pharmaceutical compositions comprising such, methods of preparing such, and methods of using one or more of such compounds for inhibiting cancer cell growth, and treating diseases associated with dysregulated HDAC and/or HMGR activity (e.g., cancer, inflammatory disease, autoimmue disease, allergic disease, hypercholesterolemia, neurogenerative disease, or infectious disease).

Without wishing to be bound by any particular theory, the compounds as described herein are surprisingly multifunctional compounds, including (1) a hydroxamate moiety that may bind to the catalytic zinc binding region of HDAC, (2) at least one hydroxyl moiety that may bind to the catalytic outer-tunnel of HDAC, and (3) a hydrophobic moiety (e.g., the cyclic moiety attached to C7) that may interact with the surface recognition hydrophobic binding region of HDAC. These compounds may bind to HMGR through similar binding motifs described herein. The compounds described here differ from atorvastatin and lovastatin in that the latter do not bind to the catalytic zinc binding region of HDAC. The compounds described here also differ from trichostatin A and suberoylanalide hydroxamic acid in that the latter do not bind to the catalytic outer-tunnel of HDAC. Thus, the compounds described herein are more active in inhibiting cancer cell growth and less toxic as compared to known compounds such as atorvastatin, lovastatin, trichostatin A, and suberoylanalide hydroxamic acid. Further, certain compounds described here were found to reduce cancer cell resistance to anti-cancer drugs such as Oxaliplatin under hypoxia conditions.

I. Compounds

The compounds as described herein can have the structure of Formula (I), which is described herein, and pharmaceutically acceptable salts thereof.

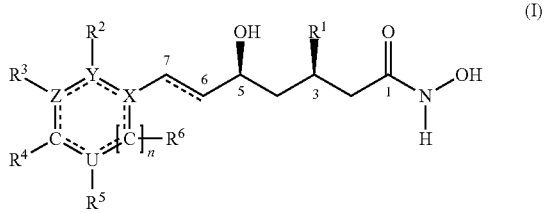

(I)

In some embodiments, they can be solvates, hydrates, polymorphs, co-crystals, tautomers, stereoisomers, isotopically labeled derivatives, and prodrugs of Formula (I).

In Formula (I), n can be 0 or 1. Alternatively or in addition, each of U, X, Y, and Z independently can be carbon, e.g. (=C($R^5$)— or —C($R^5$)=), (=C($R^2$)— or —C($R^2$)=), or (=C($R^3$)— or —C($R^3$)=), or nitrogen, e.g., (=N—, —N= or —N($R^5$)—, (=N—, —N=, or —N($R^2$)—), or (=N—, —N=, or —N($R^3$)—). In some examples, U or Y can be independently carbon or nitrogen; X can be carbon; and Z can be carbon. In other examples, all of U, Y, X, or Z can be carbon. In yet other examples, U can be nitrogen; and all of Y, X, or Z can be carbon. Alternatively, Y can be nitrogen; and all of U, X, or Z can be carbon. In still other examples, both U and Y can be nitrogen; and both X and Z can be carbon. Some specific examples follow: (i) all of U, Y, X, or Z are carbon; and n is 1; (ii) U is nitrogen, all of Y, X, and Z are carbon, and n is 1, (iii both U and Z are nitrogen, both Y and X are carbon, and n is 1; (iv) Y is nitrogen, all of U, X, and Z are carbon, and n is 0; and (v) X is nitrogen, all of U, Y, and Z are carbon; and n is 0.

In certain embodiments, ═══ can be a single bond. In certain embodiments, ═══ can be a double bond. In one example, X is carbon, all of Y, Z, and U are independently carbon or nitrogen, and the bond between C6 and C7 is a double bond when Y is carbon and Z or U is nitrogen.

Alternatively or in addition, substituent $R^1$ in Formula (I) can be substituted or unsubstituted, branched or unbranched alkyl, such as fluoroalkyl (e.g., perfluoroalkyl), chloroalkyl, bromoalkyl, or iodoalkyl. In certain embodiments, $R^1$ can be $C_{1-12}$ alkyl or $C_{1-6}$ alkyl (e.g., methyl, ethyl, propyl, butyl, pentyl, or hexyl).

Further, $R^1$ can be substituted or unsubstituted, branched or unbranched alkenyl (e.g., vinyl), substituted or unsubstituted, branched or unbranched alkynyl (e.g., ethynyl), substituted or unsubstituted aryl (e.g., 6- to 14-membered or 6- to 10-membered aryl, or monocyclic (e.g., phenyl) or bicyclic aryl (e.g., naphthyl)).

In other embodiments, $R^1$ can be substituted or unsubstituted heteroaryl, such as heteroaryl, wherein one, two, three, or four atoms in the heteroaryl ring can be independently nitrogen, oxygen, or sulfur. In certain embodiments, $R^1$ can be monocyclic or bicyclic heteroaryl. In certain embodiments, $R^1$ can be 5- or 6-membered, monocyclic heteroaryl (e.g., pyridyl). In certain embodiments, $R^1$ can be bicyclic heteroaryl, wherein the point of attachment may be on any atom of the bicyclic heteroaryl ring system, as valency permits. In certain embodiments, $R^1$ can be 9- or 10-membered, bicyclic heteroaryl.

In certain embodiments, $R^1$ can be substituted or unsubstituted cycloalkyl, such as monocyclic or bicyclic cycloalkyl. In certain examples, $R^1$ can be 3- to 7-membered, monocyclic cycloalkyl (e.g., cyclopropyl, cyclobutyl, cyclopentyl, cyclohexyl, or cycloheptyl). In other examples, $R^1$ can be 5- to 13-membered, bicyclic cycloalkyl.

In certain embodiments, $R^1$ can be substituted or unsubstituted cycloalkenyl, such as monocyclic or bicyclic cycloalkenyl. In certain examples, $R^1$ can be 3- to 7-membered, monocyclic cycloalkenyl (e.g., cyclopropenyl, cyclobutenyl, cyclopentenyl, cyclohexenyl, or cycloheptenyl). In other examples, $R^1$ can be 5- to 13-membered, bicyclic cycloalkenyl.

In certain embodiments, $R^1$ can be substituted or unsubstituted aralkyl, such as $R^1$ can be aralkyl, wherein the alkyl portion of aralkyl can be substituted or unsubstituted alkyl, such as $C_{1-12}$ or $C_{1-6}$ alkyl (e.g., methyl, ethyl, propyl, butyl, pentyl, or hexyl). In some examples, $R^1$ can be aralkyl, wherein the aryl portion of aralkyl can be substituted or unsubstituted aryl. In other examples, $R^1$ can be aralkyl, wherein the aryl portion of aralkyl can be 6- to 14-membered or 6- to 10-membered aryl. In yet other examples, $R^1$ can be aralkyl, wherein the aryl portion of aralkyl can be monocyclic (e.g., phenyl) or bicyclic (e.g., naphthyl) aryl. Alternatively, $R^1$ can be substituted or unsubstituted Bn.

In certain embodiments, $R^1$ can be substituted or unsubstituted aralkenyl, such as aralkenyl, wherein the alkenyl portion of aralkenyl can be substituted or unsubstituted alkenyl, such as $C_{1-12}$ or $C_{1-6}$ alkenyl (e.g., vinyl). In some examples, $R^1$ can be aralkenyl, wherein the aryl portion of aralkenyl can be substituted or unsubstituted aryl. In other examples, $R^1$ can be aralkenyl, wherein the aryl portion of aralkenyl can be 6- to 14-membered or 6- to 10-membered aryl. In yet other examples, $R^1$ can be aralkenyl, wherein the aryl portion of aralkenyl can be monocyclic (e.g., phenyl) or bicyclic (e.g., naphthyl) aryl.

In certain embodiments, $R^1$ can be substituted or unsubstituted aralkynyl, such as aralkynyl, wherein the alkynyl portion of aralkynyl can be substituted or unsubstituted alkynyl, such as $C_{1-12}$ or $C_{1-6}$ alkynyl (e.g., vinyl). In some examples, $R^1$ can be aralkynyl, wherein the aryl portion of aralkynyl can be substituted or unsubstituted aryl. In other examples, $R^1$ can be aralkynyl, wherein the aryl portion of aralkynyl can be 6- to 14-membered or 6- to 10-membered aryl. In yet other examples, $R^1$ can be aralkynyl, wherein the aryl portion of aralkynyl can be monocyclic (e.g., phenyl) or bicyclic (e.g., naphthyl) aryl.

In certain embodiments, $R^1$ can be substituted or unsubstituted heteroaralkyl, such as heteroaralkyl, wherein the alkyl portion of heteroaralkyl can be substituted or unsubstituted alkyl, such as $C_{1-12}$ or $C_{1-6}$ alkyl (e.g., methyl, ethyl, propyl, butyl, pentyl, or hexyl). In some examples, $R^1$ can be heteroaralkyl, wherein the heteroaryl portion of heteroaralkyl can be substituted or unsubstituted heteroaryl. In other examples, $R^1$ can be heteroaralkyl, wherein the heteroaryl portion of heteroaralkyl can be 5- to 6-membered monocyclic, or 9- to 10-membered bicyclic heteroaryl, wherein one, two, three, or four atoms in the heteroaryl ring can be independently nitrogen, oxygen, or sulfur. The point of attachment may be on any atom of the heteroaryl ring system, as valency permits.

In certain embodiments, $R^1$ can be substituted or unsubstituted heteroaralkenyl, such as heteroaralkenyl, wherein the alkenyl portion of heteroaralkenyl can be substituted or unsubstituted alkenyl, such as $C_{1-12}$ or $C_{1-6}$ alkenyl (e.g., vinyl). In some examples, $R^1$ can be heteroaralkenyl, wherein the heteroaryl portion of heteroaralkenyl can be substituted or unsubstituted heteroaryl. In other examples, $R^1$ can be heteroaralkenyl, wherein the heteroaryl portion of heteroaralkenyl can be 5- to 6-membered monocyclic, or 9- to 10-membered bicyclic heteroaryl, wherein one, two, three, or four atoms in the heteroaryl ring can be independently nitrogen, oxygen, or sulfur. The point of attachment may be on any atom of the heteroaryl ring system, as valency permits.

In certain embodiments, $R^1$ can be substituted or unsubstituted heteroaralkynyl, such as heteroaralkynyl, wherein the alkynyl portion of heteroaralkynyl can be substituted or unsubstituted alkynyl, such as $C_{1-12}$ or $C_{1-6}$ alkynyl (e.g., ethynyl). In some examples, $R^1$ can be heteroaralkynyl, wherein the heteroaryl portion of heteroaralkynyl can be substituted or unsubstituted heteroaryl. In other examples, $R^1$ can be heteroaralkynyl, wherein the heteroaryl portion of heteroaralkynyl can be 5- to 6-membered monocyclic, or 9- to 10-membered bicyclic heteroaryl, wherein one, two, three, or four atoms in the heteroaryl ring can be independently nitrogen, oxygen, or sulfur. The point of attachment may be on any atom of the heteroaryl ring system, as valency permits.

In certain embodiments, $R^1$ can be substituted or unsubstituted, saturated or unsaturated (e.g., partially unsaturated) heterocyclyl, such as heterocyclyl including one, two, or three double bonds in the heterocyclic ring. In some examples, $R^1$ can be heterocyclyl, wherein one, two, or three atoms in the heterocyclic ring can be independently nitrogen, oxygen, or sulfur. In other examples, $R^1$ can be monocyclic heterocyclyl (e.g., 3- to 7-membered monocyclic) or bicyclic (e.g., 5- to 13-membered bicyclic) heterocyclyl.

In certain embodiments, $R^1$ can be substituted or unsubstituted acyl. In some examples, $R^1$ can be —C(=O)—$R^{1a}$, wherein $R^{1a}$ can be H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, or heterocyclyl. In other examples, $R^1$ can be —C(=O)—$OR^{1b}$, wherein $R^{1b}$ can be H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, heterocyclyl, or an oxygen protecting group. In yet other examples, $R^1$ can be —C(=O)O-(oxygen protecting group), wherein the oxygen protecting group can be silyl, TBDPS, TBDMS, TIPS, TES, TMS, MOM, THP, t-Bu, Bn, allyl, acetyl, pivaloyl, or benzoyl. Alternatively, $R^1$ can be —C(=O)OH.

In certain embodiments, $R^1$ can be substituted or unsubstituted aminocarbonyl. In certain embodiments, $R^1$ can be C(=O)N($R^{1c}$)$_2$, wherein each instance of $R^{1c}$ can be independently H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, heterocyclyl, or a nitrogen protecting group. In certain embodiments, $R^1$ can be —C(=O)NH (nitrogen protecting group), wherein the nitrogen protecting group can be Bn, Boc, Cbz, Fmoc, trifluoroacetyl, triphenylmethyl, acetyl, or Ts. In certain embodiments, $R^1$ can be unsubstituted aminocarbonyl (i.e., —C(=O)NH$_2$).

In certain embodiments, $R^1$ can be substituted or unsubstituted amino. In certain embodiments, $R^1$ can be —N($R^{1d}$)$_2$, wherein each instance of $R^{1d}$ can be independently H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, heterocyclyl, or a nitrogen protecting group. In certain embodiments, $R^1$ can be —NH (nitrogen protecting group), wherein the nitrogen protecting group can be Bn, Boc, Cbz, Fmoc, trifluoroacetyl, triphenylmethyl, acetyl, or Ts. In certain embodiments, $R^1$ can be unsubstituted amino (i.e., —NH$_2$).

In certain embodiments, $R^1$ can be substituted or unsubstituted hydroxyl. In certain embodiments, $R^1$ can be —O(oxygen protecting group). In certain embodiments, $R^1$ can be —O (oxygen protecting group), wherein the oxygen protecting group can be silyl, TBDPS, TBDMS, TIPS, TES, TMS, MOM, THP, t-Bu, Bn, allyl, acetyl, pivaloyl, or benzoyl. In certain embodiments, $R^1$ can be unsubstituted hydroxyl (i.e., —OH).

In certain embodiments, $R^1$ can be substituted or unsubstituted alkoxy. In certain embodiments, $R^1$ can be —O (substituted or unsubstituted alkyl) (e.g., —O (substituted or unsubstituted $C_{1-6}$ alkyl)). In certain embodiments, $R^1$ can be —OCH$_2$ (substituted or unsubstituted phenyl) (e.g.,

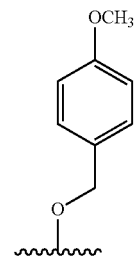

or —OBn). In certain embodiments, $R^1$ can be —O (unsubstituted $C_{1-6}$ alkyl) (e.g., —OMe, —OEt, —OPr, or —OBu).

In certain embodiments, $R^1$ can be substituted or unsubstituted acyloxy. In certain embodiments, $R^1$ can be —OC(=O)—$R^{1e}$, wherein $R^{1e}$ can be H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, or heterocyclyl. In certain embodiments, $R^1$ can be —OC(=O)-(substituted or unsubstituted alkyl). In certain embodiments, $R^1$ can be acetyl. In certain embodiments, $R^1$ can be —OC(=O)O—$R^{1f}$ wherein $R^{1f}$ can be H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, or heterocyclyl. In certain embodiments, $R^1$ can be —OC(=O)OH.

In certain embodiments, $R^1$ can be substituted or unsubstituted silyloxy. In certain embodiments, $R^1$ can be —OSi($R^{1g}$)$_3$, wherein each instance of $R^{1g}$ can be independently substituted or unsubstituted alkyl, substituted or unsubstituted aralkyl (e.g., benzyl), or substituted or unsubstituted aryl (e.g., phenyl). In certain embodiments, $R^1$ can be —O—Si(Me)$_3$, —O—Si(Et)$_3$, —O—Si(Pr)$_3$, —O—Si(Me)$_2$-tert-Bu, or —O—Si(Ph)$_2$-tert-Bu.

In certain embodiments, $R^1$ can be substituted or unsubstituted amido. In certain embodiments, $R^1$ can be —N($R^{1h}$)C(=O)$R^{1h}$, —N($R^{1h}$)—C(=O)—O$R^{1h}$, or N($R^{1h}$)—C(=O)—N($R^{1h}$)$_2$, wherein each instance of $R^{1h}$ can be independently H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, heterocyclyl, a nitrogen protecting group when attached to a nitrogen atom, or an oxygen protecting group when attached to an oxygen atom. In certain embodiments, $R^1$ can be —N($R^{1h}$)—C(=O)—$R^{1h}$, —N($R^{1h}$)—C(=O)—O$R^{1h}$, or —N($R^{1h}$)—C(=O)—N($R^{1h}$)$_2$.

In certain embodiments, $R^1$ can be substituted or unsubstituted carbamoyl. In certain embodiments, $R^1$ can be —OC(=O)N($R^{1j}$)$_2$, wherein each instance of $R^{1j}$ can be independently H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, heterocyclyl, or a nitrogen protecting group. In certain embodiments, $R^1$ can be —OC(=O)NH (nitrogen protecting group), wherein the nitrogen protecting group can be Bn, Boc, Cbz, Fmoc, trifluoroacetyl, triphenylmethyl, acetyl, or Ts. In certain embodiments, $R^1$ can be unsubstituted carbamoyl (i.e., —OC(=O)NH$_2$).

In certain embodiments, $R^1$ can be substituted or unsubstituted sulfonamido. In certain embodiments, $R^1$ can be —N($R^{1k}$)S(=O)$_2$$R^{1k}$, —N($R^{1k}$)S(=O)$_2$O$R^{1k}$, or —N($R^{1k}$)S(=O)$_2$N($R^{1k}$)$_2$, wherein each instance of $R^{1k}$ can be independently H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, heterocyclyl, a nitrogen protecting group when attached to a nitrogen atom, or an oxygen protecting group when attached to an oxygen group. In certain embodiments, $R^1$ can be —N($R^{1k}$)S(=O)$_2$$R^{1k}$, —N($R^{1k}$)S(=O)$_2$O$R^{1k}$, or —N($R^{1k}$)S(=O)$_2$N($R^{1k}$)$_2$.

In certain embodiments, $R^1$ can be unsubstituted hydroxyl or substituted or unsubstituted alkoxy.

The compounds of Formula (I) may include substituent $R^2$. In certain embodiments, $R^2$ can be substituted or unsubstituted, branched or unbranched alkyl. In certain embodiments, $R^2$ can be fluoroalkyl (e.g., perfluoroalkyl), chloroalkyl, bromoalkyl, or iodoalkyl. In certain embodiments, $R^2$ can be $C_{1-12}$ alkyl or $C_{1-6}$ alkyl (e.g., methyl, ethyl, propyl (e.g., isopropyl), butyl, pentyl, or hexyl).

In certain embodiments, $R^2$ can be substituted or unsubstituted, branched or unbranched alkenyl (e.g., vinyl).

In certain embodiments, $R^2$ can be substituted or unsubstituted, branched or unbranched alkynyl (e.g., ethynyl).

In certain embodiments, $R^2$ can be substituted or unsubstituted aryl. In certain embodiments, $R^2$ can be 6- to 14-membered or 6- to 10-membered aryl. In certain embodiments, $R^2$ can be monocyclic (e.g., phenyl (e.g., para-fluorophenyl)) or bicyclic aryl (e.g., naphthyl).

In certain embodiments, $R^2$ can be substituted or unsubstituted heteroaryl. In certain embodiments, $R^2$ can be heteroaryl, wherein one, two, three, or four atoms in the heteroaryl ring can be independently nitrogen, oxygen, or sulfur. In certain embodiments, $R^2$ can be monocyclic or bicyclic heteroaryl. In certain embodiments, $R^2$ can be 5- or 6-membered, monocyclic heteroaryl (e.g., pyridyl). In certain embodiments, $R^2$ can be bicyclic heteroaryl, wherein the point of attachment may be on any atom of the bicyclic heteroaryl ring system, as valency permits. In certain embodiments, $R^2$ can be 9- or 10-membered, bicyclic heteroaryl.

In certain embodiments, $R^2$ can be substituted or unsubstituted cycloalkyl. In certain embodiments, $R^2$ can be monocyclic or bicyclic cycloalkyl. In certain embodiments, $R^2$ can be 3- to 7-membered, monocyclic cycloalkyl (e.g., cyclopropyl, cyclobutyl, cyclopentyl, cyclohexyl, or cycloheptyl). In certain embodiments, $R^2$ can be 5- to 13-membered, bicyclic cycloalkyl.

In certain embodiments, $R^2$ can be substituted or unsubstituted cycloalkenyl. In certain embodiments, $R^2$ can be monocyclic or bicyclic cycloalkenyl. In certain embodiments, $R^2$ can be 3- to 7-membered, monocyclic cycloalkenyl (e.g., cyclopropenyl, cyclobutenyl, cyclopentenyl, cyclohexenyl, or cycloheptenyl). In certain embodiments, $R^2$ can be 5- to 13-membered, bicyclic cycloalkenyl.

In certain embodiments, $R^2$ can be substituted or unsubstituted aralkyl. In certain embodiments, $R^2$ can be aralkyl, wherein the alkyl portion of aralkyl can be substituted or unsubstituted alkyl, such as $C_{1-12}$ or $C_{1-6}$ alkyl (e.g., methyl, ethyl, propyl, butyl, pentyl, or hexyl). In certain embodiments, $R^2$ can be aralkyl, wherein the aryl portion of aralkyl can be substituted or unsubstituted aryl. In certain embodiments, $R^2$ can be aralkyl, wherein the aryl portion of aralkyl can be 6- to 14-membered or 6- to 10-membered aryl. In certain embodiments, $R^2$ can be aralkyl, wherein the aryl portion of aralkyl can be monocyclic (e.g., phenyl) or bicyclic (e.g., naphthyl) aryl. In certain embodiments, $R^2$ can be substituted or unsubstituted Bn.

In certain embodiments, $R^2$ can be substituted or unsubstituted aralkenyl. In certain embodiments, $R^2$ can be aralkenyl, wherein the alkenyl portion of aralkenyl can be substituted or unsubstituted alkenyl, such as $C_{1-12}$ or $C_{1-6}$ alkenyl (e.g., vinyl). In certain embodiments, $R^2$ can be aralkenyl, wherein the aryl portion of aralkenyl can be substituted or unsubstituted aryl. In certain embodiments, $R^2$ can be aralkenyl, wherein the aryl portion of aralkenyl can be 6- to 14-membered or 6- to 10-membered aryl. In certain embodiments, $R^2$ can be aralkenyl, wherein the aryl portion of aralkenyl can be monocyclic (e.g., phenyl) or bicyclic (e.g., naphthyl) aryl.

In certain embodiments, $R^2$ can be substituted or unsubstituted aralkynyl. In certain embodiments, $R^2$ can be aralkynyl, wherein the alkynyl portion of aralkynyl can be substituted or unsubstituted alkynyl, such as $C_{1-12}$ or $C_{1-6}$ alkynyl (e.g., vinyl). In certain embodiments, $R^2$ can be aralkynyl, wherein the aryl portion of aralkynyl can be substituted or unsubstituted aryl. In certain embodiments, $R^2$ can be aralkynyl, wherein the aryl portion of aralkynyl can be 6- to 14-membered or 6- to 10-membered aryl. In certain embodiments, $R^2$ can be aralkynyl, wherein the aryl portion of aralkynyl can be monocyclic (e.g., phenyl) or bicyclic (e.g., naphthyl) aryl.

In certain embodiments, $R^2$ can be substituted or unsubstituted heteroaralkyl. In certain embodiments, $R^2$ can be heteroaralkyl, wherein the alkyl portion of heteroaralkyl can be substituted or unsubstituted alkyl, such as $C_{1-12}$ or $C_{1-6}$ alkyl (e.g., methyl, ethyl, propyl, butyl, pentyl, or hexyl). In certain embodiments, $R^2$ can be heteroaralkyl, wherein the heteroaryl portion of heteroaralkyl can be substituted or unsubstituted heteroaryl. In certain embodiments, $R^2$ can be heteroaralkyl, wherein the heteroaryl portion of heteroaralkyl can be 5- to 6-membered monocyclic, or 9- to 10-membered bicyclic heteroaryl, wherein one, two, three, or four atoms in the heteroaryl ring can be independently nitrogen, oxygen, or sulfur. The point of attachment may be on any atom of the heteroaryl ring system, as valency permits.

In certain embodiments, $R^2$ can be substituted or unsubstituted heteroaralkenyl. In certain embodiments, $R^2$ can be heteroaralkenyl, wherein the alkenyl portion of heteroaralkenyl can be substituted or unsubstituted alkenyl, such as $C_{1-12}$ or $C_{1-6}$ alkenyl (e.g., vinyl). In certain embodiments, $R^2$ can be heteroaralkenyl, wherein the heteroaryl portion of heteroaralkenyl can be substituted or unsubstituted heteroaryl. In certain embodiments, $R^2$ can be heteroaralkenyl, wherein the heteroaryl portion of heteroaralkenyl can be 5- to 6-membered monocyclic, or 9- to 10-membered bicyclic heteroaryl, wherein one, two, three, or four atoms in the heteroaryl ring can be independently nitrogen, oxygen, or sulfur. The point of attachment may be on any atom of the heteroaryl ring system, as valency permits.

In certain embodiments, $R^2$ can be substituted or unsubstituted heteroaralkynyl. In certain embodiments, $R^2$ can be heteroaralkynyl, wherein the alkynyl portion of heteroaralkynyl can be substituted or unsubstituted alkynyl, such as $C_{1-12}$ or $C_{1-6}$ alkynyl (e.g., ethynyl). In certain embodiments, $R^2$ can be heteroaralkynyl, wherein the heteroaryl portion of heteroaralkynyl can be substituted or unsubstituted heteroaryl. In certain embodiments, $R^2$ can be heteroaralkynyl, wherein the heteroaryl portion of heteroaralkynyl can be 5- to 6-membered monocyclic, or 9- to 10-membered bicyclic heteroaryl, wherein one, two, three, or four atoms in the heteroaryl ring can be independently nitrogen, oxygen, or sulfur. The point of attachment may be on any atom of the heteroaryl ring system, as valency permits.

In certain embodiments, $R^2$ can be substituted or unsubstituted, saturated or unsaturated (e.g., partially unsaturated) heterocyclyl. In certain embodiments, $R^2$ can be heterocyclyl including one, two, or three double bonds in the heterocyclic ring. In certain embodiments, $R^2$ can be heterocyclyl, wherein one, two, or three atoms in the heterocyclic ring can be independently nitrogen, oxygen, or sulfur. In certain embodiments, $R^2$ can be monocyclic heterocyclyl (e.g., 3- to 7-membered monocyclic) or bicyclic (e.g., 5- to 13-membered bicyclic) heterocyclyl.

In certain embodiments, $R^2$ can be substituted or unsubstituted acyl. In certain embodiments, $R^2$ can be —C(=O)—$R^{2a}$, wherein $R^{2a}$ can be H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, or heterocyclyl. In certain embodiments, $R^2$ can be —C(=O)—$OR^{2b}$, wherein $R^{2b}$ can be H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, heterocyclyl, or an oxygen protecting group. In certain embodiments, $R^2$ can be —C(=O)O-(oxygen protecting group), wherein the oxygen protecting group can be silyl, TBDPS, TBDMS, TIPS, TES, TMS, MOM, THP, t-Bu, Bn, allyl, acetyl, pivaloyl, or benzoyl. In certain embodiments, $R^2$ can be —C(=O)OH.

In certain embodiments, $R^2$ can be substituted or unsubstituted aminocarbonyl. In certain embodiments, $R^2$ can be —C(=O)N($R^{2c}$)$_2$, wherein each instance of $R^{2c}$ can be independently H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, heterocyclyl, or a nitrogen protecting group. In certain embodiments, $R^2$ can be —C(=O)NH (nitrogen protecting group), wherein the nitrogen protecting group can be Bn, Boc, Cbz, Fmoc, trifluoroacetyl, triphenylmethyl, acetyl, or Ts. In certain embodiments, $R^2$ can be unsubstituted aminocarbonyl (i.e., —C(=O)NH$_2$).

In certain embodiments, $R^2$ can be substituted or unsubstituted amino. In certain embodiments, $R^2$ can be —N($R^{2d}$)$_2$, wherein each instance of $R^{2d}$ can be independently H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, heterocyclyl, or a nitrogen protecting group. In certain embodiments, $R^2$ can be —NH (nitrogen protecting group), wherein the nitrogen protecting group can be Bn, Boc, Cbz, Fmoc, trifluoroacetyl, triphenylmethyl, acetyl, or Ts. In certain embodiments, $R^2$ can be unsubstituted amino (i.e., —NH$_2$).

In certain embodiments, $R^2$ can be substituted or unsubstituted hydroxyl. In certain embodiments, $R^2$ can be —O(oxygen protecting group). In certain embodiments, $R^2$ can be —O (oxygen protecting group), wherein the oxygen protecting group can be silyl, TBDPS, TBDMS, TIPS, TES, TMS, MOM, THP, t-Bu, Bn, allyl, acetyl, pivaloyl, or benzoyl. In certain embodiments, $R^2$ can be unsubstituted hydroxyl (i.e., —OH).

In certain embodiments, $R^2$ can be substituted or unsubstituted alkoxy. In certain embodiments, $R^2$ can be —O (substituted or unsubstituted alkyl) (e.g., —O (substituted or unsubstituted $C_{1-6}$ alkyl)). In certain embodiments, $R^2$ can be —OCH$_2$ (substituted or unsubstituted phenyl) (e.g.,

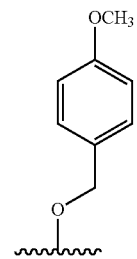

or —OBn. In certain embodiments, $R^2$ can be —O (unsubstituted $C_{1-6}$ alkyl) (e.g., —OMe, —OEt, —OPr, or —OBu).

In certain embodiments, $R^2$ can be substituted or unsubstituted acyloxy. In certain embodiments, $R^2$ can be —OC(=O)—$R^{2e}$, wherein $R^{2e}$ can be H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, or heterocyclyl. In certain embodiments, $R^2$ can be —OC(=O)-(substituted or unsubstituted alkyl). In certain embodiments, $R^2$ can be acetyl. In certain embodiments, $R^2$ can be —OC(=O)O—$R^{2f}$, wherein $R^{2f}$ can be H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, or heterocyclyl. In certain embodiments, $R^2$ can be —OC(=O)OH.

In certain embodiments, $R^2$ can be substituted or unsubstituted silyloxy. In certain embodiments, $R^2$ can be —OSi($R^{2g}$)$_3$, wherein each instance of $R^{2g}$ can be independently substituted or unsubstituted alkyl, substituted or unsubstituted aralkyl (e.g., benzyl), or substituted or unsubstituted aryl (e.g., phenyl). In certain embodiments, $R^2$ can be —O—Si(Me)$_3$, —O—Si(Et)$_3$, —O—Si(Pr)$_3$, —O—Si(Me)$_2$-tert-Bu, or —O—Si(Ph)$_2$-tert-Bu.

In certain embodiments, $R^2$ can be substituted or unsubstituted amido. In certain embodiments, $R^2$ can be —N($R^{2h}$)—C(=O)—$R^{2h}$, —N($R^{2h}$)—C(=O)—OR$^{2h}$, or —N($R^{2h}$)—C(=O)—N($R^2$)$_2$, wherein each instance of $R^{21}$ can be independently H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, heterocyclyl, a nitrogen protecting group when attached to a nitrogen atom, or an oxygen protecting group when attached to an oxygen atom. In certain embodiments, $R^2$ can be —N($R^{2h}$)—C(=O)—$R^{2h}$, —N($R^{2h}$)—C(=O)—OR$^{2h}$, or —N($R^{2h}$)—C(=O)—N($R^{2h}$)$_2$.

In certain embodiments, $R^2$ can be substituted or unsubstituted carbamoyl. In certain embodiments, $R^2$ can be —OC(=O)N($R^2$)$_2$, wherein each instance of $R^{2j}$ can be independently H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, heterocyclyl, or a nitrogen protecting group. In certain embodiments, $R^2$ can be —OC(=O)NH (nitrogen protecting group), wherein the nitrogen protecting group can be Bn, Boc, Cbz, Fmoc, trifluoroacetyl, triphenylmethyl, acetyl, or Ts. In certain embodiments, $R^2$ can be unsubstituted carbamoyl (i.e., —OC(=O)NH$_2$).

In certain embodiments, $R^2$ can be substituted or unsubstituted sulfonamido. In certain embodiments, $R^2$ can be —N($R^{2k}$)S(=O)$_2$$R^{2k}$, —N($R^{2k}$)S(=O)$_2$OR$^{2k}$, or —N($R^{2k}$)S(=O)$_2$N($R^{2k}$)$_2$, wherein each instance of $R^{2k}$ can be independently H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, heterocyclyl, a nitrogen protecting group when attached to a nitrogen atom, or an oxygen protecting group when attached to an oxygen group. In certain embodiments, $R^2$ can be —N($R^{2k}$)S(=O)$_2$$R^{2k}$, —N($R^{2k}$)S(=O)$_2$OR$^{2k}$, or —N($R^{2k}$)S(=O)$_2$N($R^{2k}$)$_2$.

In certain embodiments, $R^2$ can be connected with $R^3$ to form substituted or unsubstituted, saturated or unsaturated (e.g., partially unsaturated) carbocycle. In certain embodiments, $R^2$ can be connected with $R^3$ to form carbocycle including one, two, or three double bonds in the carbocycle. In certain embodiments, $R^2$ can be connected with $R^3$ to form 3- to 7-membered monocyclic (e.g., 3-membered monocyclic, 4-membered monocyclic, 5-membered monocyclic, 6-membered monocyclic (e.g., cyclohexenyl), or 7-membered monocyclic) or 5- to 13-membered bicyclic carbocycle.

In certain embodiments, $R^2$ can be connected with $R^3$ to form a substituted or unsubstituted, saturated or unsaturated heterocycle. In certain embodiments, $R^2$ can be connected with $R^3$ to form a heterocycle including one, two, or three double bonds in the heterocycle. In certain embodiments, $R^2$ can be connected with $R^3$ to form a heterocycle, wherein one, two, or three atoms in the heterocycle can be independently nitrogen, oxygen, or sulfur. In certain embodiments, $R^2$ can be connected with $R^3$ to form a 3- to 7-membered monocyclic or 5- to 13-membered bicyclic heterocycle.

In certain embodiments, $R^2$ can be $C_{1-6}$ alkyl or aryl (e.g., phenyl), or $R^2$ can be connected with $R^3$ to form carbocycle.

The compounds of Formula (I) may include substituent $R^3$. In certain embodiments, $R^3$ can be null. In certain embodiments, $R^3$ can be H. In certain embodiments, $R^3$ can be substituted or unsubstituted, branched or unbranched alkyl. In certain embodiments, $R^3$ can be fluoroalkyl (e.g., perfluoroalkyl), chloroalkyl, bromoalkyl, or iodoalkyl. In certain embodiments, $R^3$ can be $C_{1-12}$ alkyl or $C_{1-6}$ alkyl (e.g., methyl (e.g., methoxymethyl), ethyl, propyl, butyl, pentyl, or hexyl).

In certain embodiments, $R^3$ can be substituted or unsubstituted, branched or unbranched alkenyl (e.g., vinyl).

In certain embodiments, $R^3$ can be substituted or unsubstituted, branched or unbranched alkynyl (e.g., ethynyl).

In certain embodiments, $R^3$ can be substituted or unsubstituted aryl. In certain embodiments, $R^3$ can be 6- to 14-membered or 6- to 10-membered aryl. In certain embodiments, $R^3$ can be monocyclic (e.g., phenyl) or bicyclic aryl (e.g., naphthyl).

In certain embodiments, $R^3$ can be substituted or unsubstituted heteroaryl. In certain embodiments, $R^3$ can be heteroaryl, wherein one, two, three, or four atoms in the heteroaryl ring can be independently nitrogen, oxygen, or sulfur. In certain embodiments, $R^3$ can be monocyclic or bicyclic heteroaryl. In certain embodiments, $R^3$ can be 5- or 6-membered, monocyclic heteroaryl (e.g., pyridyl). In certain embodiments, $R^3$ can be bicyclic heteroaryl, wherein the point of attachment may be on any atom of the bicyclic heteroaryl ring system, as valency permits. In certain embodiments, $R^3$ can be 9- or 10-membered, bicyclic heteroaryl.

In certain embodiments, $R^3$ can be substituted or unsubstituted cycloalkyl. In certain embodiments, $R^3$ can be monocyclic or bicyclic cycloalkyl. In certain embodiments, $R^3$ can be 3- to 7-membered, monocyclic cycloalkyl (e.g., cyclopropyl, cyclobutyl, cyclopentyl, cyclohexyl, or cycloheptyl). In certain embodiments, $R^3$ can be 5- to 13-membered, bicyclic cycloalkyl.

In certain embodiments, $R^3$ can be substituted or unsubstituted cycloalkenyl. In certain embodiments, $R^3$ can be monocyclic or bicyclic cycloalkenyl. In certain embodiments, $R^3$ can be 3- to 7-membered, monocyclic cycloalkenyl (e.g., cyclopropenyl, cyclobutenyl, cyclopentenyl, cyclohexenyl, or cycloheptenyl). In certain embodiments, $R^3$ can be 5- to 13-membered, bicyclic cycloalkenyl.

In certain embodiments, $R^3$ can be substituted or unsubstituted aralkyl. In certain embodiments, $R^3$ can be aralkyl, wherein the alkyl portion of aralkyl can be substituted or unsubstituted alkyl, such as $C_{1-12}$ or $C_{1-6}$ alkyl (e.g., methyl, ethyl, propyl, butyl, pentyl, or hexyl). In certain embodiments, $R^3$ can be aralkyl, wherein the aryl portion of aralkyl can be substituted or unsubstituted aryl. In certain embodiments, $R^3$ can be aralkyl, wherein the aryl portion of aralkyl can be 6- to 14-membered or 6- to 10-membered aryl. In certain embodiments, $R^3$ can be aralkyl, wherein the aryl portion of aralkyl can be monocyclic (e.g., phenyl) or bicyclic (e.g., naphthyl) aryl. In certain embodiments, $R^3$ can be substituted or unsubstituted Bn.

In certain embodiments, $R^3$ can be substituted or unsubstituted aralkenyl. In certain embodiments, $R^3$ can be aralkenyl, wherein the alkenyl portion of aralkenyl can be substituted or unsubstituted alkenyl, such as $C_{1-12}$ or $C_{1-6}$ alkenyl (e.g., vinyl). In certain embodiments, $R^3$ can be aralkenyl, wherein the aryl portion of aralkenyl can be substituted or unsubstituted aryl. In certain embodiments, $R^3$ can be aralkenyl, wherein the aryl portion of aralkenyl can be 6- to 14-membered or 6- to 10-membered aryl. In certain embodiments, $R^3$ can be aralkenyl, wherein the aryl portion of aralkenyl can be monocyclic (e.g., phenyl) or bicyclic (e.g., naphthyl) aryl.

In certain embodiments, $R^3$ can be substituted or unsubstituted aralkynyl. In certain embodiments, $R^3$ can be aralkynyl, wherein the alkynyl portion of aralkynyl can be substituted or unsubstituted alkynyl, such as $C_{1-12}$ or $C_{1-6}$ alkynyl (e.g., vinyl). In certain embodiments, $R^3$ can be aralkynyl, wherein the aryl portion of aralkynyl can be substituted or unsubstituted aryl. In certain embodiments, $R^3$ can be aralkynyl, wherein the aryl portion of aralkynyl can be 6- to 14-membered or 6- to 10-membered aryl. In certain embodiments, $R^3$ can be aralkynyl, wherein the aryl portion of aralkynyl can be monocyclic (e.g., phenyl) or bicyclic (e.g., naphthyl) aryl.

In certain embodiments, $R^3$ can be substituted or unsubstituted heteroaralkyl. In certain embodiments, $R^3$ can be heteroaralkyl, wherein the alkyl portion of heteroaralkyl can be substituted or unsubstituted alkyl, such as $C_{1-12}$ or $C_{1-6}$ alkyl (e.g., methyl, ethyl, propyl, butyl, pentyl, or hexyl). In certain embodiments, $R^3$ can be heteroaralkyl, wherein the heteroaryl portion of heteroaralkyl can be substituted or unsubstituted heteroaryl. In certain embodiments, $R^3$ can be heteroaralkyl, wherein the heteroaryl portion of heteroaralkyl can be 5- to 6-membered monocyclic, or 9- to 10-membered bicyclic heteroaryl, wherein one, two, three, or four atoms in the heteroaryl ring can be independently nitrogen, oxygen, or sulfur. The point of attachment may be on any atom of the heteroaryl ring system, as valency permits.

In certain embodiments, $R^3$ can be substituted or unsubstituted heteroaralkenyl. In certain embodiments, $R^3$ can be heteroaralkenyl, wherein the alkenyl portion of heteroaralkenyl can be substituted or unsubstituted alkenyl, such as $C_{1-12}$ or $C_{1-6}$ alkenyl (e.g., vinyl). In certain embodiments, $R^3$ can be heteroaralkenyl, wherein the heteroaryl portion of heteroaralkenyl can be substituted or unsubstituted heteroaryl. In certain embodiments, $R^3$ can be heteroaralkenyl, wherein the heteroaryl portion of heteroaralkenyl can be 5- to 6-membered monocyclic, or 9- to 10-membered bicyclic heteroaryl, wherein one, two, three, or four atoms in the heteroaryl ring can be independently nitrogen, oxygen, or sulfur. The point of attachment may be on any atom of the heteroaryl ring system, as valency permits.

In certain embodiments, $R^3$ can be substituted or unsubstituted heteroaralkynyl. In certain embodiments, $R^3$ can be heteroaralkynyl, wherein the alkynyl portion of heteroaralkynyl can be substituted or unsubstituted alkynyl, such as $C_{1-12}$ or $C_{1-6}$ alkynyl (e.g., ethynyl). In certain embodiments, $R^3$ can be heteroaralkynyl, wherein the heteroaryl portion of heteroaralkynyl can be substituted or unsubstituted heteroaryl. In certain embodiments, $R^3$ can be heteroaralkynyl, wherein the heteroaryl portion of heteroaralkynyl can be 5- to 6-membered monocyclic, or 9- to 10-membered bicyclic heteroaryl, wherein one, two, three, or four atoms in the heteroaryl ring can be independently nitrogen, oxygen, or sulfur. The point of attachment may be on any atom of the heteroaryl ring system, as valency permits.

In certain embodiments, $R^3$ can be substituted or unsubstituted, saturated or unsaturated (e.g., partially unsaturated) heterocyclyl. In certain embodiments, $R^3$ can be heterocyclyl including one, two, or three double bonds in the heterocyclic ring. In certain embodiments, $R^3$ can be heterocyclyl, wherein one, two, or three atoms in the heterocyclic ring can be independently nitrogen, oxygen, or sulfur. In certain embodiments, $R^3$ can be monocyclic heterocyclyl (e.g., 3- to 7-membered monocyclic) or bicyclic (e.g., 5- to 13-membered bicyclic) heterocyclyl.

In certain embodiments, $R^3$ can be substituted or unsubstituted acyl. In certain embodiments, $R^3$ can be —C(=O)—$R^{3a}$, wherein $R^{3a}$ can be H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, or heterocyclyl. In certain embodiments, $R^3$ can be —C(=O)—$OR^{3b}$, wherein $R^{3b}$ can be H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, heterocyclyl, or an oxygen protecting group. In certain embodiments, $R^3$ can be —C(=O)O-(oxygen protecting group), wherein the oxygen protecting group can be silyl, TBDPS, TBDMS, TIPS, TES, TMS, MOM, THP, t-Bu, Bn, allyl, acetyl, pivaloyl, or benzoyl. In certain embodiments, $R^3$ can be —C(=O)OH.

In certain embodiments, $R^3$ can be substituted or unsubstituted aminocarbonyl. In certain embodiments, $R^3$ can be —C(=O)N($R^{3c}$)$_2$, wherein each instance of $R^{3c}$ can be independently H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, heterocyclyl, or a nitrogen protecting group. In certain embodiments, $R^3$ can be —C(=O)NHPh. In certain embodiments, $R^3$ can be —C(=O)NH (nitrogen protecting group), wherein the nitrogen protecting group can be Bn, Boc, Cbz, Fmoc, trifluoroacetyl, triphenylmethyl, acetyl, or Ts. In certain embodiments, $R^3$ can be unsubstituted aminocarbonyl (i.e., —C(=O)NH$_2$).

In certain embodiments, $R^3$ can be substituted or unsubstituted amino. In certain embodiments, $R^3$ can be —N($R^{3d}$)$_2$, wherein each instance of $R^{3d}$ can be independently H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, heterocyclyl, or a nitrogen protecting group. In certain embodiments, $R^3$ can be —NH (nitrogen protecting group), wherein the nitrogen protecting group can be Bn, Boc, Cbz, Fmoc, trifluoroacetyl, triphenylmethyl, acetyl, or Ts. In certain embodiments, $R^3$ can be unsubstituted amino (i.e., —NH$_2$).

In certain embodiments, $R^3$ can be substituted or unsubstituted hydroxyl. In certain embodiments, $R^3$ can be —O(oxygen protecting group). In certain embodiments, $R^3$ can be —O(oxygen protecting group), wherein the oxygen protecting group can be silyl, TBDPS, TBDMS, TIPS, TES, TMS, MOM, THP, t-Bu, Bn, allyl, acetyl, pivaloyl, or benzoyl. In certain embodiments, $R^3$ can be unsubstituted hydroxyl (i.e., —OH).

In certain embodiments, $R^3$ can be substituted or unsubstituted alkoxy. In certain embodiments, $R^3$ can be —O (substituted or unsubstituted alkyl) (e.g., —O (substituted or unsubstituted $C_{1-6}$ alkyl)). In certain embodiments, $R^3$ can be —OCH$_2$ (substituted or unsubstituted phenyl) (e.g.,

or —OBn. In certain embodiments, $R^3$ can be —O (unsubstituted $C_{1-6}$ alkyl) (e.g., —OMe, —OEt, —OPr, or —OBu).

In certain embodiments, $R^3$ can be substituted or unsubstituted acyloxy. In certain embodiments, $R^3$ can be —OC (=O)—$R^{3e}$, wherein $R^{3e}$ can be H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, or heterocyclyl. In certain embodiments, $R^3$ can be —OC(=O)-(substituted or unsubstituted alkyl). In certain embodiments, $R^3$ can be acetyl. In certain embodiments, $R^3$ can be —OC(=O)O—$R^{3f}$, wherein $R^{3f}$ can be H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, or heterocyclyl. In certain embodiments, $R^3$ can be —OC(=O)OH.

In certain embodiments, $R^3$ can be substituted or unsubstituted silyloxy. In certain embodiments, $R^3$ can be —OSi($R^{3g}$)$_3$, wherein each instance of $R^{3g}$ can be independently substituted or unsubstituted alkyl, substituted or unsubstituted aralkyl (e.g., benzyl), or substituted or unsubstituted aryl (e.g., phenyl). In certain embodiments, $R^3$ can be —O—Si(Me)$_3$, —O—Si(Et)$_3$, —O—Si(Pr)$_3$, —O—Si(Me)$_2$-tert-Bu, or —O—Si(Ph)$_2$-tert-Bu.

In certain embodiments, $R^3$ can be substituted or unsubstituted amido. In certain embodiments, $R^3$ can be —N($R^{3h}$)—C(=O)—$R^{3h}$, —N($R^{3h}$)—C(=O)—OR$^{3h}$, or —N($R^{3h}$)—C(=O)—N($R^{3h}$)$_2$, wherein each instance of $R^{3h}$ can be independently H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, heterocyclyl, a nitrogen protecting group when attached to a nitrogen atom, or an oxygen protecting group when attached to an oxygen atom. In certain embodiments, $R^3$ can be —N($R^{3h}$)—C(=O)—$R^{3h}$, —N($R^{3h}$)—C(=O)—OR$^{3h}$, or —N($R^{3h}$)—C(=O)—N($R^{3h}$)$_2$.

In certain embodiments, $R^3$ can be substituted or unsubstituted carbamoyl. In certain embodiments, $R^3$ can be —OC(=O)N($R^{3j}$)$_2$, wherein each instance of $R^{3j}$ can be independently H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, heterocyclyl, or a nitrogen protecting group. In certain embodiments, $R^3$ can be —OC(=O)NH (nitrogen protecting group), wherein the nitrogen protecting group can be Bn, Boc, Cbz, Fmoc, trifluoroacetyl, triphenylmethyl, acetyl, or Ts. In certain embodiments, $R^3$ can be unsubstituted carbamoyl (i.e., —OC(=O)NH$_2$).

In certain embodiments, $R^3$ can be substituted or unsubstituted sulfonamido. In certain embodiments, $R^3$ can be —N($R^{3k}$)S(=O)$_2$$R^{3k}$, —N($R^{3k}$)S(=O)$_2$OR$^{3k}$, or —N($R^{3k}$)S(=O)$_2$N($R^{3k}$)$_2$, wherein each instance of $R^{3k}$ can be independently H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, heterocyclyl, a nitrogen protecting group when attached to a nitrogen atom, or an oxygen protecting group when attached to an oxygen group. In certain embodiments, $R^3$ can be —N($R^{3k}$)S(=O)$_2$$R^{3k}$, —N($R^{3k}$)S(=O)$_2$OR$^{3k}$, or —N($R^{3k}$)S(=O)$_2$N($R^{3k}$)$_2$.

In certain embodiments, $R^3$ can be connected with $R^4$ to form substituted or unsubstituted, saturated or unsaturated (e.g., partially unsaturated) carbocycle. In certain embodiments, $R^3$ can be connected with $R^4$ to form carbocycle including one, two, or three double bonds in the carbocycle. In certain embodiments, $R^3$ can be connected with $R^4$ to form 3- to 7-membered monocyclic (e.g., 3-membered monocyclic, 4-membered monocyclic, 5-membered monocyclic, 6-membered monocyclic (e.g., cyclohexenyl), or 7-membered monocyclic) or 5- to 13-membered bicyclic carbocycle.

In certain embodiments, $R^3$ can be connected with $R^4$ to form a substituted or unsubstituted, saturated or unsaturated heterocycle. In certain embodiments, $R^3$ can be connected with $R^4$ to form a heterocycle including one, two, or three double bonds in the heterocycle. In certain embodiments, $R^3$ can be connected with $R^4$ to form a heterocycle, wherein one, two, or three atoms in the heterocycle can be independently nitrogen, oxygen, or sulfur. In certain embodiments, $R^3$ can be connected with $R^4$ to form a 3- to 7-membered monocyclic or 5- to 13-membered bicyclic heterocycle.

In certain embodiments, $R^3$ can be null, $C_{1-6}$ alkyl, or aminocarbonyl, or $R^3$ can be connected with $R^2$ or $R^4$ to form carbocycle (e.g., phenyl) or heterocycle.

The compounds of Formula (I) may include substituent $R^4$. In certain embodiments, $R^4$ can be null. In certain embodiments, $R^4$ can be H. In certain embodiments, $R^4$ can be substituted or unsubstituted, branched or unbranched alkyl. In certain embodiments, $R^4$ can be fluoroalkyl (e.g., perfluoroalkyl), chloroalkyl, bromoalkyl, or iodoalkyl. In certain embodiments, $R^4$ can be $C_{1-12}$ alkyl or $C_{1-6}$ alkyl (e.g., methyl, ethyl, propyl (e.g., isopropyl), butyl, pentyl, or hexyl).

In certain embodiments, $R^4$ can be substituted or unsubstituted, branched or unbranched alkenyl (e.g., vinyl).

In certain embodiments, $R^4$ can be substituted or unsubstituted, branched or unbranched alkynyl (e.g., ethynyl).

In certain embodiments, $R^4$ can be substituted or unsubstituted aryl. In certain embodiments, $R^4$ can be 6- to 14-membered or 6- to 10-membered aryl. In certain embodiments, $R^4$ can be monocyclic (e.g., phenyl) or bicyclic aryl (e.g., naphthyl).

In certain embodiments, $R^4$ can be substituted or unsubstituted heteroaryl. In certain embodiments, $R^4$ can be heteroaryl, wherein one, two, three, or four atoms in the heteroaryl ring can be independently nitrogen, oxygen, or sulfur. In certain embodiments, $R^4$ can be monocyclic or bicyclic heteroaryl. In certain embodiments, $R^4$ can be 5- or 6-membered, monocyclic heteroaryl (e.g., pyridyl). In certain embodiments, $R^4$ can be bicyclic heteroaryl, wherein the point of attachment may be on any atom of the bicyclic heteroaryl ring system, as valency permits. In certain embodiments, $R^4$ can be 9- or 10-membered, bicyclic heteroaryl.

In certain embodiments, $R^4$ can be substituted or unsubstituted cycloalkyl. In certain embodiments, $R^4$ can be monocyclic or bicyclic cycloalkyl. In certain embodiments, $R^4$ can be 3- to 7-membered, monocyclic cycloalkyl (e.g., cyclopropyl, cyclobutyl, cyclopentyl, cyclohexyl, or cycloheptyl). In certain embodiments, $R^4$ can be 5- to 13-membered, bicyclic cycloalkyl.

In certain embodiments, $R^4$ can be substituted or unsubstituted cycloalkenyl. In certain embodiments, $R^4$ can be monocyclic or bicyclic cycloalkenyl. In certain embodiments, $R^4$ can be 3- to 7-membered, monocyclic cycloalkenyl (e.g., cyclopropenyl, cyclobutenyl, cyclopentenyl, cyclohexenyl, or cycloheptenyl). In certain embodiments, $R^4$ can be 5- to 13-membered, bicyclic cycloalkenyl.

In certain embodiments, $R^4$ can be substituted or unsubstituted aralkyl. In certain embodiments, $R^4$ can be aralkyl, wherein the alkyl portion of aralkyl can be substituted or unsubstituted alkyl, such as $C_{1-12}$ or $C_{1-6}$ alkyl (e.g., methyl, ethyl, propyl, butyl, pentyl, or hexyl). In certain embodiments, $R^4$ can be aralkyl, wherein the aryl portion of aralkyl can be substituted or unsubstituted aryl. In certain embodiments, $R^4$ can be aralkyl, wherein the aryl portion of aralkyl can be 6- to 14-membered or 6- to 10-membered aryl. In certain embodiments, $R^4$ can be aralkyl, wherein the aryl portion of aralkyl can be monocyclic (e.g., phenyl) or bicyclic (e.g., naphthyl) aryl. In certain embodiments, $R^4$ can be substituted or unsubstituted Bn.

In certain embodiments, $R^4$ can be substituted or unsubstituted aralkenyl. In certain embodiments, $R^4$ can be aralkenyl, wherein the alkenyl portion of aralkenyl can be substituted or unsubstituted alkenyl, such as $C_{1-12}$ or $C_{1-6}$ alkenyl (e.g., vinyl). In certain embodiments, $R^4$ can be aralkenyl, wherein the aryl portion of aralkenyl can be substituted or unsubstituted aryl. In certain embodiments, $R^4$ can be aralkenyl, wherein the aryl portion of aralkenyl can be 6- to 14-membered or 6- to 10-membered aryl. In certain embodiments, $R^4$ can be aralkenyl, wherein the aryl portion of aralkenyl can be monocyclic (e.g., phenyl) or bicyclic (e.g., naphthyl) aryl.

In certain embodiments, $R^4$ can be substituted or unsubstituted aralkynyl. In certain embodiments, $R^4$ can be aralkynyl, wherein the alkynyl portion of aralkynyl can be substituted or unsubstituted alkynyl, such as $C_{1-12}$ or $C_{1-6}$ alkynyl (e.g., vinyl). In certain embodiments, $R^4$ can be aralkynyl, wherein the aryl portion of aralkynyl can be substituted or unsubstituted aryl. In certain embodiments, $R^4$ can be aralkynyl, wherein the aryl portion of aralkynyl can be 6- to 14-membered or 6- to 10-membered aryl. In certain embodiments, $R^4$ can be aralkynyl, wherein the aryl portion of aralkynyl can be monocyclic (e.g., phenyl) or bicyclic (e.g., naphthyl) aryl.

In certain embodiments, $R^4$ can be substituted or unsubstituted heteroaralkyl. In certain embodiments, $R^4$ can be heteroaralkyl, wherein the alkyl portion of heteroaralkyl can be substituted or unsubstituted alkyl, such as $C_{1-12}$ or $C_{1-6}$ alkyl (e.g., methyl, ethyl, propyl, butyl, pentyl, or hexyl). In certain embodiments, $R^4$ can be heteroaralkyl, wherein the heteroaryl portion of heteroaralkyl can be substituted or unsubstituted heteroaryl. In certain embodiments, $R^4$ can be heteroaralkyl, wherein the heteroaryl portion of heteroaralkyl can be 5- to 6-membered monocyclic, or 9- to 10-membered bicyclic heteroaryl, wherein one, two, three, or four atoms in the heteroaryl ring can be independently nitrogen, oxygen, or sulfur. The point of attachment may be on any atom of the heteroaryl ring system, as valency permits.

In certain embodiments, $R^4$ can be substituted or unsubstituted heteroaralkenyl. In certain embodiments, $R^4$ can be heteroaralkenyl, wherein the alkenyl portion of heteroaralkenyl can be substituted or unsubstituted alkenyl, such as $C_{1-12}$ or $C_{1-6}$ alkenyl (e.g., vinyl). In certain embodiments, $R^4$ can be heteroaralkenyl, wherein the heteroaryl portion of heteroaralkenyl can be substituted or unsubstituted heteroaryl. In certain embodiments, $R^4$ can be heteroaralkenyl, wherein the heteroaryl portion of heteroaralkenyl can be 5- to 6-membered monocyclic, or 9- to 10-membered bicyclic heteroaryl, wherein one, two, three, or four atoms in the heteroaryl ring can be independently nitrogen, oxygen, or sulfur. The point of attachment may be on any atom of the heteroaryl ring system, as valency permits.

In certain embodiments, $R^4$ can be substituted or unsubstituted heteroaralkynyl. In certain embodiments, $R^4$ can be heteroaralkynyl, wherein the alkynyl portion of heteroaralkynyl can be substituted or unsubstituted alkynyl, such as $C_{1-12}$ or $C_{1-6}$ alkynyl (e.g., ethynyl). In certain embodiments, $R^4$ can be heteroaralkynyl, wherein the heteroaryl portion of heteroaralkynyl can be substituted or unsubstituted heteroaryl. In certain embodiments, $R^4$ can be heteroaralkynyl, wherein the heteroaryl portion of heteroaralkynyl can be 5- to 6-membered monocyclic, or 9- to 10-membered bicyclic heteroaryl, wherein one, two, three, or four atoms in the heteroaryl ring can be independently nitrogen, oxygen, or sulfur. The point of attachment may be on any atom of the heteroaryl ring system, as valency permits.

In certain embodiments, $R^4$ can be substituted or unsubstituted, saturated or unsaturated (e.g., partially unsaturated) heterocyclyl. In certain embodiments, $R^4$ can be heterocyclyl including one, two, or three double bonds in the heterocyclic ring. In certain embodiments, $R^4$ can be heterocyclyl, wherein one, two, or three atoms in the heterocyclic ring can be independently nitrogen, oxygen, or sulfur. In certain embodiments, $R^4$ can be monocyclic heterocyclyl (e.g., 3- to 7-membered monocyclic) or bicyclic (e.g., 5- to 13-membered bicyclic) heterocyclyl.

In certain embodiments, $R^4$ can be substituted or unsubstituted acyl. In certain embodiments, $R^4$ can be —C(=O)—$R^{4a}$, wherein $R^{4a}$ can be H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, or heterocyclyl. In certain embodiments, $R^4$ can be —C(=O)—$OR^{4b}$, wherein $R^{4b}$ can be H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, heterocyclyl, or an oxygen protecting group. In certain embodiments, $R^4$ can be —C(=O)O-(oxygen protecting group), wherein the oxygen protecting group can be silyl, TBDPS, TBDMS, TIPS, TES, TMS, MOM, THP, t-Bu, Bn, allyl, acetyl, pivaloyl, or benzoyl. In certain embodiments, $R^4$ can be —C(=O)OH.

In certain embodiments, $R^4$ can be substituted or unsubstituted aminocarbonyl. In certain embodiments, $R^4$ can be —C(=O)N($R^{4c}$)$_2$, wherein each instance of $R^{4a}$ can be independently H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, heterocyclyl, or a nitrogen protecting group. In certain embodiments, $R^4$ can be —C(=O)NH (nitrogen protecting group), wherein the nitrogen protecting group can be Bn, Boc, Cbz, Fmoc, trifluoroacetyl, triphenylmethyl, acetyl, or Ts. In certain embodiments, $R^4$ can be unsubstituted aminocarbonyl (i.e., —C(=O)NH$_2$).

In certain embodiments, $R^4$ can be substituted or unsubstituted amino. In certain embodiments, $R^4$ can be —N($R^{4d}$)$_2$, wherein each instance of $R^{4d}$ can be independently H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, heterocyclyl, or a nitrogen protecting group. In certain embodiments, $R^4$ can be —NH (nitrogen protecting group), wherein the nitrogen protecting group can be Bn, Boc, Cbz, Fmoc, trifluoroacetyl, triphenylmethyl, acetyl, or Ts. In certain embodiments, $R^4$ can be unsubstituted amino (i.e., —NH$_2$).

In certain embodiments, $R^4$ can be substituted or unsubstituted hydroxyl. In certain embodiments, $R^4$ can be —O(oxygen protecting group). In certain embodiments, $R^4$ can be —O(oxygen protecting group), wherein the oxygen protecting group can be silyl, TBDPS, TBDMS, TIPS, TES, TMS, MOM, THP, t-Bu, Bn, allyl, acetyl, pivaloyl, or benzoyl. In certain embodiments, $R^4$ can be unsubstituted hydroxyl (i.e., —OH).

In certain embodiments, $R^4$ can be substituted or unsubstituted alkoxy. In certain embodiments, $R^4$ can be —O (substituted or unsubstituted alkyl) (e.g., —O (substituted or unsubstituted $C_{1-6}$ alkyl)). In certain embodiments, $R^4$ can be —OCH$_2$ (substituted or unsubstituted phenyl) (e.g.,

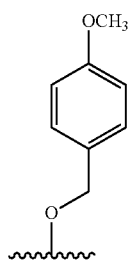 [SMILES: *OCc1ccc(OC)cc1]

for —OBn. In certain embodiments, $R^4$ can be —O (unsubstituted $C_{1-6}$ alkyl) (e.g., —OMe, —OEt, —OPr, or —OBu).

In certain embodiments, $R^4$ can be substituted or unsubstituted acyloxy. In certain embodiments, $R^4$ can be —OC(=O)—$R^{4e}$, wherein $R^{4e}$ can be H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, or heterocyclyl. In certain embodiments, $R^4$ can be —OC(=O)-(substituted or unsubstituted alkyl). In certain embodiments, $R^4$ can be acetyl. In certain embodiments, $R^4$ can be —OC(=O)O—$R^{4f}$, wherein $R^{4f}$ can be H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, or heterocyclyl. In certain embodiments, $R^4$ can be —OC(=O)OH.

In certain embodiments, $R^4$ can be substituted or unsubstituted silyloxy. In certain embodiments, $R^4$ can be —OSi($R^{4g}$)$_3$, wherein each instance of $R^{4g}$ can be independently substituted or unsubstituted alkyl, substituted or unsubstituted aralkyl (e.g., benzyl), or substituted or unsubstituted aryl (e.g., phenyl). In certain embodiments, $R^4$ can be —O—Si(Me)$_3$, —O—Si(Et)$_3$, —O—Si(Pr)$_3$, —O—Si(Me)$_2$-tert-Bu, or —O—Si(Ph)$_2$-tert-Bu.

In certain embodiments, $R^4$ can be substituted or unsubstituted amido. In certain embodiments, $R^4$ can be —N($R^{4h}$)—C(=O)—$R^{4h}$, —N($R^{4h}$)—C(=O)—OR$^{4h}$, or —N($R^{4h}$)—C(=O)—N($R^{4h}$)$_2$, wherein each instance of $R^{4h}$ can be independently H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, heterocyclyl, a nitrogen protecting group when attached to a nitrogen atom, or an oxygen protecting group when attached to an oxygen atom. In certain embodiments, $R^4$ can be —N($R^{4h}$)—C(=O)—$R^{4h}$, —N($R^{4h}$)—C(=O)—OR$^{4h}$ or —N($R^{4h}$)—C(=O)—N($R^{4h}$)$_2$.

In certain embodiments, $R^4$ can be substituted or unsubstituted carbamoyl. In certain embodiments, $R^4$ can be —OC(=O)N($R^{4j}$)$_2$, wherein each instance of $R^{4j}$ can be independently H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, heterocyclyl, or a nitrogen protecting group. In certain embodiments, $R^4$ can be —OC(=O)NH (nitrogen protecting group), wherein the nitrogen protecting group can be Bn, Boc, Cbz, Fmoc, trifluoroacetyl, triphenylmethyl, acetyl, or Ts. In certain embodiments, $R^4$ can be unsubstituted carbamoyl (i.e., —OC(=O)NH$_2$).

In certain embodiments, $R^4$ can be substituted or unsubstituted sulfonamido. In certain embodiments, $R^4$ can be —N($R^{4k}$)S(=O)$_2$R$^{4k}$, —N($R^{4k}$)S(=O)$_2$OR$^{4k}$, or —N($R^{4k}$)S(=O)$_2$N($R^{4k}$)$_2$, wherein each instance of $R^{4k}$ can be independently H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, heterocyclyl, a nitrogen protecting group when attached to a nitrogen atom, or an oxygen protecting group when attached to an oxygen group. In certain embodiments, $R^4$ can be —N($R^{4k}$)S(=O)$_2$R$^{4k}$, —N($R^{4k}$)S(=O)$_2$OR$^{4k}$, or —N($R^{4k}$)S(=O)$_2$N($R^{4k}$)$_2$. In certain embodiments, $R^4$ can be of the formula:

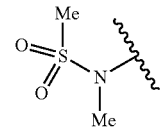

In certain embodiments, $R^4$ can be $C_{1-6}$ alkyl, aryl (e.g., phenyl), or sulfonamido, or $R^4$ can be connected with $R^3$ to form carbocycle (e.g., phenyl).

The compounds of Formula (I) may include substituent $R^5$. In certain embodiments, $R^5$ can be null. In certain embodiments, $R^5$ can be H. In certain embodiments, $R^1$ can be substituted or unsubstituted, branched or unbranched alkyl. In certain embodiments, $R^5$ can be fluoroalkyl (e.g., perfluoroalkyl), chloroalkyl, bromoalkyl, or iodoalkyl. In certain embodiments, $R^5$ can be $C_{1-12}$ alkyl or $C_{1-6}$ alkyl (e.g., methyl, ethyl, propyl, butyl, pentyl, or hexyl).

In certain embodiments, $R^5$ can be substituted or unsubstituted, branched or unbranched alkenyl (e.g., vinyl).

In certain embodiments, $R^5$ can be substituted or unsubstituted, branched or unbranched alkynyl (e.g., ethynyl).

In certain embodiments, $R^5$ can be substituted or unsubstituted aryl. In certain embodiments, $R^5$ can be 6- to 14-membered or 6- to 10-membered aryl. In certain embodiments, $R^5$ can be monocyclic (e.g., phenyl (e.g., para-fluorophenyl)) or bicyclic aryl (e.g., naphthyl).

In certain embodiments, $R^5$ can be substituted or unsubstituted heteroaryl. In certain embodiments, $R^5$ can be heteroaryl, wherein one, two, three, or four atoms in the heteroaryl ring can be independently nitrogen, oxygen, or sulfur. In certain embodiments, $R^5$ can be monocyclic or bicyclic heteroaryl. In certain embodiments, $R^5$ can be 5- or 6-membered, monocyclic heteroaryl (e.g., pyridyl). In certain embodiments, $R^5$ can be bicyclic heteroaryl, wherein the point of attachment may be on any atom of the bicyclic heteroaryl ring system, as valency permits. In certain embodiments, $R^5$ can be 9- or 10-membered, bicyclic heteroaryl.

In certain embodiments, $R^5$ can be substituted or unsubstituted cycloalkyl. In certain embodiments, $R^5$ can be monocyclic or bicyclic cycloalkyl. In certain embodiments, $R^5$ can be 3- to 7-membered, monocyclic cycloalkyl (e.g., cyclopropyl, cyclobutyl, cyclopentyl, cyclohexyl, or cycloheptyl). In certain embodiments, $R^5$ can be 5- to 13-membered, bicyclic cycloalkyl.

In certain embodiments, $R^5$ can be substituted or unsubstituted cycloalkenyl. In certain embodiments, $R^5$ can be monocyclic or bicyclic cycloalkenyl. In certain embodiments, $R^5$ can be 3- to 7-membered, monocyclic cycloalkenyl (e.g., cyclopropenyl, cyclobutenyl, cyclopentenyl, cyclohexenyl, or cycloheptenyl). In certain embodiments, $R^5$ can be 5- to 13-membered, bicyclic cycloalkenyl.

In certain embodiments, $R^5$ can be substituted or unsubstituted aralkyl. In certain embodiments, $R^5$ can be aralkyl, wherein the alkyl portion of aralkyl can be substituted or unsubstituted alkyl, such as $C_{1-12}$ or $C_{1-6}$ alkyl (e.g., methyl, ethyl, propyl, butyl, pentyl, or hexyl). In certain embodiments, $R^5$ can be aralkyl, wherein the aryl portion of aralkyl can be substituted or unsubstituted aryl. In certain embodiments, $R^5$ can be aralkyl, wherein the aryl portion of aralkyl can be 6- to 14-membered or 6- to 10-membered aryl. In certain embodiments, $R^5$ can be aralkyl, wherein the aryl portion of aralkyl can be monocyclic (e.g., phenyl) or bicyclic (e.g., naphthyl) aryl. In certain embodiments, $R^5$ can be substituted or unsubstituted Bn.

In certain embodiments, $R^5$ can be substituted or unsubstituted aralkenyl. In certain embodiments, $R^5$ can be aralkenyl, wherein the alkenyl portion of aralkenyl can be substituted or unsubstituted alkenyl, such as $C_{1-12}$ or $C_{1-6}$ alkenyl (e.g., vinyl). In certain embodiments, $R^5$ can be aralkenyl, wherein the aryl portion of aralkenyl can be substituted or unsubstituted aryl. In certain embodiments, $R^5$ can be aralkenyl, wherein the aryl portion of aralkenyl can be 6- to 14-membered or 6- to 10-membered aryl. In certain embodiments, $R^5$ can be aralkenyl, wherein the aryl portion of aralkenyl can be monocyclic (e.g., phenyl) or bicyclic (e.g., naphthyl) aryl.

In certain embodiments, $R^5$ can be substituted or unsubstituted aralkynyl. In certain embodiments, $R^5$ can be aralkynyl, wherein the alkynyl portion of aralkynyl can be substituted or unsubstituted alkynyl, such as $C_{1-12}$ or $C_{1-6}$ alkynyl (e.g., vinyl). In certain embodiments, $R^5$ can be aralkynyl, wherein the aryl portion of aralkynyl can be substituted or unsubstituted aryl. In certain embodiments, $R^5$ can be aralkynyl, wherein the aryl portion of aralkynyl can be 6- to 14-membered or 6- to 10-membered aryl. In certain embodiments, $R^5$ can be aralkynyl, wherein the aryl portion of aralkynyl can be monocyclic (e.g., phenyl) or bicyclic (e.g., naphthyl) aryl.

In certain embodiments, $R^5$ can be substituted or unsubstituted heteroaralkyl. In certain embodiments, $R^5$ can be heteroaralkyl, wherein the alkyl portion of heteroaralkyl can be substituted or unsubstituted alkyl, such as $C_{1-12}$ or $C_{1-6}$ alkyl (e.g., methyl, ethyl, propyl, butyl, pentyl, or hexyl). In certain embodiments, $R^5$ can be heteroaralkyl, wherein the heteroaryl portion of heteroaralkyl can be substituted or unsubstituted heteroaryl. In certain embodiments, $R^5$ can be heteroaralkyl, wherein the heteroaryl portion of heteroaralkyl can be 5- to 6-membered monocyclic, or 9- to 10-membered bicyclic heteroaryl, wherein one, two, three, or four atoms in the heteroaryl ring can be independently nitrogen, oxygen, or sulfur. The point of attachment may be on any atom of the heteroaryl ring system, as valency permits.

In certain embodiments, $R^5$ can be substituted or unsubstituted heteroaralkenyl. In certain embodiments, $R^5$ can be heteroaralkenyl, wherein the alkenyl portion of heteroaralkenyl can be substituted or unsubstituted alkenyl, such as $C_{1-12}$ or $C_{1-6}$ alkenyl (e.g., vinyl). In certain embodiments, $R^5$ can be heteroaralkenyl, wherein the heteroaryl portion of heteroaralkenyl can be substituted or unsubstituted heteroaryl. In certain embodiments, $R^5$ can be heteroaralkenyl, wherein the heteroaryl portion of heteroaralkenyl can be 5- to 6-membered monocyclic, or 9- to 10-membered bicyclic heteroaryl, wherein one, two, three, or four atoms in the heteroaryl ring can be independently nitrogen, oxygen, or sulfur. The point of attachment may be on any atom of the heteroaryl ring system, as valency permits.

In certain embodiments, $R^5$ can be substituted or unsubstituted heteroaralkynyl. In certain embodiments, $R^5$ can be heteroaralkynyl, wherein the alkynyl portion of heteroaralkynyl can be substituted or unsubstituted alkynyl, such as $C_{1-12}$ or $C_{1-6}$ alkynyl (e.g., ethynyl). In certain embodiments, $R^5$ can be heteroaralkynyl, wherein the heteroaryl portion of heteroaralkynyl can be substituted or unsubstituted heteroaryl. In certain embodiments, $R^5$ can be heteroaralkynyl, wherein the heteroaryl portion of heteroaralkynyl can be 5- to 6-membered monocyclic, or 9- to 10-membered bicyclic heteroaryl, wherein one, two, three, or four atoms in the heteroaryl ring can be independently nitrogen, oxygen, or sulfur. The point of attachment may be on any atom of the heteroaryl ring system, as valency permits.

In certain embodiments, $R^5$ can be substituted or unsubstituted, saturated or unsaturated (e.g., partially unsaturated) heterocyclyl. In certain embodiments, $R^5$ can be heterocyclyl including one, two, or three double bonds in the heterocyclic ring. In certain embodiments, $R^5$ can be heterocyclyl, wherein one, two, or three atoms in the heterocyclic ring can be independently nitrogen, oxygen, or sulfur. In certain embodiments, $R^5$ can be monocyclic heterocyclyl (e.g., 3- to 7-membered monocyclic) or bicyclic (e.g., 5- to 13-membered bicyclic) heterocyclyl.

In certain embodiments, $R^5$ can be substituted or unsubstituted acyl. In certain embodiments, $R^5$ can be —C(=O)—$R^{5a}$, wherein $R^{5a}$ can be H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, or heterocyclyl. In certain embodiments, $R^5$ can be —C(=O)—$OR^{5b}$, wherein $R^{5b}$ can be H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, heterocyclyl, or an oxygen protecting group. In certain embodiments, $R^5$ can be —C(=O)O-(oxygen protecting group), wherein the oxygen protecting group can be silyl, TBDPS, TBDMS, TIPS, TES, TMS, MOM, THP, t-Bu, Bn, allyl, acetyl, pivaloyl, or benzoyl. In certain embodiments, $R^5$ can be —C(=O)OH.

In certain embodiments, $R^5$ can be substituted or unsubstituted aminocarbonyl. In certain embodiments, $R^5$ can be —C(=O)N($R^{5c}$)$_2$, wherein each instance of $R^{5c}$ can be independently H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, heterocyclyl, or a nitrogen protecting group. In certain embodiments, $R^5$ can be —C(=O)NH (nitrogen protecting group), wherein the nitrogen protecting group can be Bn, Boc, Cbz, Fmoc, trifluoroacetyl, triphenylmethyl, acetyl, or Ts. In certain embodiments, $R^5$ can be unsubstituted aminocarbonyl (i.e., —C(=O)NH$_2$).

In certain embodiments, $R^5$ can be substituted or unsubstituted amino. In certain embodiments, $R^5$ can be —N($R^{5d}$)$_2$, wherein each instance of $R^{5d}$ can be independently H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, heterocyclyl, or a nitrogen protecting group. In certain embodiments, $R^5$ can be —NH (nitrogen protecting group), wherein the nitrogen protecting group can be Bn, Boc, Cbz, Fmoc, trifluoroacetyl, triphenylmethyl, acetyl, or Ts. In certain embodiments, $R^5$ can be unsubstituted amino (i.e., —NH$_2$).

In certain embodiments, $R^5$ can be substituted or unsubstituted hydroxyl. In certain embodiments, $R^5$ can be —O (oxygen protecting group). In certain embodiments, $R^5$ can be —O (oxygen protecting group), wherein the oxygen protecting group can be silyl, TBDPS, TBDMS, TIPS, TES, TMS, MOM, THP, t-Bu, Bn, allyl, acetyl, pivaloyl, or benzoyl. In certain embodiments, $R^5$ can be unsubstituted hydroxyl (i.e., —OH).

In certain embodiments, $R^5$ can be substituted or unsubstituted alkoxy. In certain embodiments, $R^5$ can be —O (substituted or unsubstituted alkyl) (e.g., —O (substituted or unsubstituted $C_{1-6}$ alkyl)). In certain embodiments, $R^5$ can be —OCH$_2$ (substituted or OCH$_3$ unsubstituted phenyl) (e.g.,

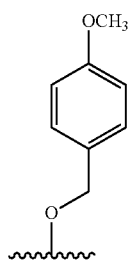 [SMILES: *OCc1ccc(OC)cc1]

or —OBn. In certain embodiments, $R^5$ can be —O (unsubstituted $C_{1-6}$ alkyl) (e.g., —OMe, —OEt, —OPr, or —OBu).

In certain embodiments, $R^5$ can be substituted or unsubstituted acyloxy. In certain embodiments, $R^5$ can be —OC(=O)—$R^{5e}$, wherein $R^{5e}$ can be H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, or heterocyclyl. In certain embodiments, $R^5$ can be —OC(=O)-(substituted or unsubstituted alkyl). In certain embodiments, $R^5$ can be acetyl. In certain embodiments, $R^5$ can be —OC(=O)O—$R^{5f}$, wherein $R^{5f}$ can be H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, or heterocyclyl. In certain embodiments, $R^5$ can be —OC(=O)OH.

In certain embodiments, $R^5$ can be substituted or unsubstituted silyloxy. In certain embodiments, $R^5$ can be —OSi($R^{5g}$)$_3$, wherein each instance of $R^{5g}$ can be independently substituted or unsubstituted alkyl, substituted or unsubstituted aralkyl (e.g., benzyl), or substituted or unsubstituted aryl (e.g., phenyl). In certain embodiments, $R^5$ can be —O—Si(Me)$_3$, —O—Si(Et)$_3$, —O—Si(Pr)$_3$, —O—Si(Me)$_2$-tert-Bu, or —O—Si(Ph)$_2$-tert-Bu.

In certain embodiments, $R^5$ can be substituted or unsubstituted amido. In certain embodiments, $R^5$ can be —N($R^{5h}$)—C(=O)—$R^{5h}$, —N($R^{5h}$)—C(=O)—OR$^{5h}$, Or —N($R^{5h}$)—C(=O)—N($R^{5h}$)$_2$, wherein each instance of $R^{5h}$ can be independently H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, heterocyclyl, a nitrogen protecting group when attached to a nitrogen atom, or an oxygen protecting group when attached to an oxygen atom. In certain embodiments, $R^5$ can be —N($R^{5h}$)—C(=O)—$R^{5h}$, —N($R^{5h}$)—C(=O)—OR$^{5h}$, or —N($R^{5h}$)—C(=O)—N($R^{5h}$)$_2$.

In certain embodiments, $R^5$ can be substituted or unsubstituted carbamoyl. In certain embodiments, $R^5$ can be —OC(=O)N($R^{5i}$)$_2$, wherein each instance of $R^{5i}$ can be independently H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, heterocyclyl, or a nitrogen protecting group. In certain embodiments, $R^5$ can be —OC(=O)NH (nitrogen protecting group), wherein the nitrogen protecting group can be Bn, Boc, Cbz, Fmoc, trifluoroacetyl, triphenylmethyl, acetyl, or Ts. In certain embodiments, $R^5$ can be unsubstituted carbamoyl (i.e., —OC(=O)NH$_2$).

In certain embodiments, $R^5$ can be substituted or unsubstituted sulfonamido. In certain embodiments, $R^5$ can be —N($R^{5k}$)S(=O)$_2$R$^{5k}$, —N($R^{5k}$)S(=O)$_2$OR$^{5k}$, or —N($R^{5k}$)S(=O)$_2$N($R^{5k}$)$_2$, wherein each instance of $R^{5k}$ can be independently H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, heterocyclyl, a nitrogen protecting group when attached to a nitrogen atom, or an oxygen protecting group when attached to an oxygen group. In certain embodiments, $R^5$ can be —N($R^{5k}$)S(=O)$_2$R$^{5k}$, —N($R^{5k}$)S(=O)$_2$OR$^{5k}$, or —N($R^{5k}$)S(=O)$_2$N($R^{5k}$)$_2$.

In certain embodiments, $R^5$ can be null, H, or aryl (e.g., phenyl).

The compounds of Formula (I) may include substituent $R^6$. In certain embodiments, $R^6$ can be null. In certain embodiments, $R^6$ can be H. In certain embodiments, $R^6$ can be substituted or unsubstituted, branched or unbranched alkyl. In certain embodiments, $R^6$ can be fluoroalkyl (e.g., perfluoroalkyl), chloroalkyl, bromoalkyl, or iodoalkyl. In certain embodiments, $R^6$ can be $C_{1-12}$ alkyl or $C_{1-6}$ alkyl (e.g., methyl, ethyl, propyl (e.g., isopropyl), butyl, pentyl, or hexyl).

In certain embodiments, $R^6$ can be substituted or unsubstituted, branched or unbranched alkenyl (e.g., vinyl).

In certain embodiments, $R^6$ can be substituted or unsubstituted, branched or unbranched alkynyl (e.g., ethynyl).

In certain embodiments, $R^6$ can be substituted or unsubstituted aryl. In certain embodiments, $R^6$ can be 6- to 14-membered or 6- to 10-membered aryl. In certain embodiments, $R^6$ can be monocyclic (e.g., phenyl) or bicyclic aryl (e.g., naphthyl).

In certain embodiments, $R^6$ can be substituted or unsubstituted heteroaryl. In certain embodiments, $R^6$ can be heteroaryl, wherein one, two, three, or four atoms in the heteroaryl ring can be independently nitrogen, oxygen, or sulfur. In certain embodiments, $R^6$ can be monocyclic or bicyclic heteroaryl. In certain embodiments, $R^6$ can be 5- or 6-membered, monocyclic heteroaryl (e.g., pyridyl). In certain embodiments, $R^6$ can be bicyclic heteroaryl, wherein the point of attachment may be on any atom of the bicyclic heteroaryl ring system, as valency permits. In certain embodiments, $R^6$ can be 9- or 10-membered, bicyclic heteroaryl.

In certain embodiments, $R^6$ can be substituted or unsubstituted cycloalkyl. In certain embodiments, $R^6$ can be monocyclic or bicyclic cycloalkyl. In certain embodiments, $R^6$ can be 3- to 7-membered, monocyclic cycloalkyl (e.g., cyclopropyl, cyclobutyl, cyclopentyl, cyclohexyl, or cycloheptyl). In certain embodiments, $R^6$ can be 5- to 13-membered, bicyclic cycloalkyl.

In certain embodiments, $R^6$ can be substituted or unsubstituted cycloalkenyl. In certain embodiments, $R^6$ can be monocyclic or bicyclic cycloalkenyl. In certain embodiments, $R^6$ can be 3- to 7-membered, monocyclic cycloalkenyl (e.g., cyclopropenyl, cyclobutenyl, cyclopentenyl, cyclohexenyl, or cycloheptenyl). In certain embodiments, $R^6$ can be 5- to 13-membered, bicyclic cycloalkenyl.

In certain embodiments, $R^6$ can be substituted or unsubstituted aralkyl. In certain embodiments, $R^6$ can be aralkyl, wherein the alkyl portion of aralkyl can be substituted or unsubstituted alkyl, such as $C_{1-12}$ or $C_{1-6}$ alkyl (e.g., methyl, ethyl, propyl, butyl, pentyl, or hexyl). In certain embodiments, $R^6$ can be aralkyl, wherein the aryl portion of aralkyl can be substituted or unsubstituted aryl. In certain embodiments, $R^6$ can be aralkyl, wherein the aryl portion of aralkyl can be 6- to 14-membered or 6- to 10-membered aryl. In certain embodiments, $R^6$ can be aralkyl, wherein the aryl portion of aralkyl can be monocyclic (e.g., phenyl) or bicyclic (e.g., naphthyl) aryl. In certain embodiments, $R^6$ can be substituted or unsubstituted Bn.

In certain embodiments, $R^6$ can be substituted or unsubstituted aralkenyl. In certain embodiments, $R^6$ can be aralkenyl, wherein the alkenyl portion of aralkenyl can be substituted or unsubstituted alkenyl, such as $C_{1-12}$ or $C_{1-6}$ alkenyl (e.g., vinyl). In certain embodiments, $R^6$ can be aralkenyl, wherein the aryl portion of aralkenyl can be substituted or unsubstituted aryl. In certain embodiments, $R^6$ can be aralkenyl, wherein the aryl portion of aralkenyl can be 6- to 14-membered or 6- to 10-membered aryl. In certain embodiments, $R^6$ can be aralkenyl, wherein the aryl portion of aralkenyl can be monocyclic (e.g., phenyl) or bicyclic (e.g., naphthyl) aryl.

In certain embodiments, $R^6$ can be substituted or unsubstituted aralkynyl. In certain embodiments, $R^6$ can be aralkynyl, wherein the alkynyl portion of aralkynyl can be substituted or unsubstituted alkynyl, such as $C_{1-12}$ or $C_{1-6}$ alkynyl (e.g., vinyl). In certain embodiments, $R^6$ can be aralkynyl, wherein the aryl portion of aralkynyl can be substituted or unsubstituted aryl. In certain embodiments, $R^6$ can be aralkynyl, wherein the aryl portion of aralkynyl can be 6- to 14-membered or 6- to 10-membered aryl. In certain embodiments, $R^6$ can be aralkynyl, wherein the aryl portion of aralkynyl can be monocyclic (e.g., phenyl) or bicyclic (e.g., naphthyl) aryl.

In certain embodiments, $R^6$ can be substituted or unsubstituted heteroaralkyl. In certain embodiments, $R^6$ can be heteroaralkyl, wherein the alkyl portion of heteroaralkyl can be substituted or unsubstituted alkyl, such as $C_{1-12}$ or $C_{1-6}$ alkyl (e.g., methyl, ethyl, propyl, butyl, pentyl, or hexyl). In certain embodiments, $R^6$ can be heteroaralkyl, wherein the heteroaryl portion of heteroaralkyl can be substituted or unsubstituted heteroaryl. In certain embodiments, $R^6$ can be heteroaralkyl, wherein the heteroaryl portion of heteroaralkyl can be 5- to 6-membered monocyclic, or 9- to 10-membered bicyclic heteroaryl, wherein one, two, three, or four atoms in the heteroaryl ring can be independently nitrogen, oxygen, or sulfur. The point of attachment may be on any atom of the heteroaryl ring system, as valency permits.

In certain embodiments, $R^6$ can be substituted or unsubstituted heteroaralkenyl. In certain embodiments, $R^6$ can be heteroaralkenyl, wherein the alkenyl portion of heteroaralkenyl can be substituted or unsubstituted alkenyl, such as $Cp_{112}$ or $C_{1-6}$ alkenyl (e.g., vinyl). In certain embodiments, $R^6$ can be heteroaralkenyl, wherein the heteroaryl portion of heteroaralkenyl can be substituted or unsubstituted heteroaryl. In certain embodiments, $R^6$ can be heteroaralkenyl, wherein the heteroaryl portion of heteroaralkenyl can be 5- to 6-membered monocyclic, or 9- to 10-membered bicyclic heteroaryl, wherein one, two, three, or four atoms in the heteroaryl ring can be independently nitrogen, oxygen, or sulfur. The point of attachment may be on any atom of the heteroaryl ring system, as valency permits.

In certain embodiments, $R^6$ can be substituted or unsubstituted heteroaralkynyl. In certain embodiments, $R^6$ can be heteroaralkynyl, wherein the alkynyl portion of heteroaralkynyl can be substituted or unsubstituted alkynyl, such as $C_{1-12}$ or $C_{1-6}$ alkynyl (e.g., ethynyl). In certain embodiments, $R^6$ can be heteroaralkynyl, wherein the heteroaryl portion of heteroaralkynyl can be substituted or unsubstituted heteroaryl. In certain embodiments, $R^6$ can be heteroaralkynyl, wherein the heteroaryl portion of heteroaralkynyl can be 5- to 6-membered monocyclic, or 9- to 10-membered bicyclic heteroaryl, wherein one, two, three, or four atoms in the heteroaryl ring can be independently nitrogen, oxygen, or sulfur. The point of attachment may be on any atom of the heteroaryl ring system, as valency permits.

In certain embodiments, $R^6$ can be substituted or unsubstituted, saturated or unsaturated (e.g., partially unsaturated) heterocyclyl. In certain embodiments, $R^6$ can be heterocyclyl including one, two, or three double bonds in the heterocyclic ring. In certain embodiments, $R^6$ can be heterocyclyl, wherein one, two, or three atoms in the heterocyclic ring can be independently nitrogen, oxygen, or sulfur. In certain embodiments, $R^6$ can be monocyclic heterocyclyl (e.g., 3- to 7-membered monocyclic) or bicyclic (e.g., 5- to 13-membered bicyclic) heterocyclyl.

In certain embodiments, $R^6$ can be substituted or unsubstituted acyl. In certain embodiments, $R^6$ can be —C(=O)—$R^{6a}$, wherein $R^{6a}$ can be H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, or heterocyclyl. In certain embodiments, $R^6$ can be —C(=O)—$OR^{6b}$, wherein $R^{6b}$ can be H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, heterocyclyl, or an oxygen protecting group. In certain embodiments, $R^6$ can be —C(=O)O-(oxygen protecting group), wherein the oxygen protecting group can be silyl, TBDPS, TBDMS, TIPS, TES, TMS, MOM, THP, t-Bu, Bn, allyl, acetyl, pivaloyl, or benzoyl. In certain embodiments, $R^6$ can be —C(=O)OH.

In certain embodiments, $R^6$ can be substituted or unsubstituted aminocarbonyl. In certain embodiments, $R^6$ can be —C(=O)N($R^{6c}$)$_2$, wherein each instance of $R^{6c}$ can be independently H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, heterocyclyl, or a nitrogen protecting group. In certain embodiments, $R^6$ can be —C(=O)NH (nitrogen protecting group), wherein the nitrogen protecting group can be Bn, Boc, Cbz, Fmoc, trifluoroacetyl, triphenylmethyl, acetyl, or Ts. In certain embodiments, $R^6$ can be unsubstituted aminocarbonyl (i.e., —C(=O)NH$_2$).

In certain embodiments, $R^6$ can be substituted or unsubstituted amino. In certain embodiments, $R^6$ can be —N($R^{6d}$)$_2$, wherein each instance of $R^{6d}$ can be independently H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, heterocyclyl, or a nitrogen protecting group. In certain embodiments, $R^6$ can be —NH (nitrogen protecting group), wherein the nitrogen protecting group can be Bn, Boc, Cbz, Fmoc, trifluoroacetyl, triphenylmethyl, acetyl, or Ts. In certain embodiments, $R^6$ can be unsubstituted amino (i.e., —NH$_2$).

In certain embodiments, $R^6$ can be substituted or unsubstituted hydroxyl. In certain embodiments, $R^6$ can be —O(oxygen protecting group). In certain embodiments, $R^6$ can be —O(oxygen protecting group), wherein the oxygen protecting group can be silyl, TBDPS, TBDMS, TIPS, TES, TMS, MOM, THP, t-Bu, Bn, allyl, acetyl, pivaloyl, or benzoyl. In certain embodiments, $R^6$ can be unsubstituted hydroxyl (i.e., —OH).

In certain embodiments, $R^6$ can be substituted or unsubstituted alkoxy. In certain embodiments, $R^6$ can be —O (substituted or unsubstituted alkyl) (e.g., —O (substituted or unsubstituted $C_{1-6}$ alkyl)). In certain embodiments, $R^6$ can be —OCH$_2$ (substituted or unsubstituted phenyl) (e.g.,

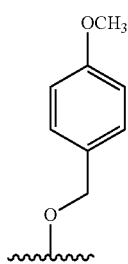 [SMILES: *OCc1ccc(OC)cc1]

or —OBn. In certain embodiments, $R^6$ can be —O (unsubstituted $C_{1-6}$ alkyl) (e.g., —OMe, —OEt, —OPr, or —OBu).

In certain embodiments, $R^6$ can be substituted or unsubstituted acyloxy. In certain embodiments, $R^6$ can be —OC(=O)—$R^{6e}$, wherein $R^{6e}$ can be H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, or heterocyclyl. In certain embodiments, $R^6$ can be —OC(=O)-(substituted or unsubstituted alkyl). In certain embodiments, $R^6$ can be acetyl. In certain embodiments, $R^6$ can be —OC(=O)O—$R^{6f}$, wherein $R^{6f}$ can be H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, or heterocyclyl. In certain embodiments, $R^6$ can be —OC(=O)OH.

In certain embodiments, $R^6$ can be substituted or unsubstituted silyloxy. In certain embodiments, $R^6$ can be —OSi($R^{6g}$)$_3$, wherein each instance of $R^{6g}$ can be independently substituted or unsubstituted alkyl, substituted or unsubstituted aralkyl (e.g., benzyl), or substituted or unsubstituted aryl (e.g., phenyl). In certain embodiments, $R^6$ can be —O—Si(Me)$_3$, —O—Si(Et)$_3$, —O—Si(Pr)$_3$, —O—Si(Me)$_2$-tert-Bu, or —O—Si(Ph)$_2$-tert-Bu.

In certain embodiments, $R^6$ can be substituted or unsubstituted amido. In certain embodiments, $R^6$ can be —N($R^{6h}$)—C(=O)—$R^{6h}$, —N($R^{6h}$)—C(=O)—O$R^{6h}$, or —N($R^{6h}$)—C(=O)—N($R^{6h}$)$_2$, wherein each instance of $R^{6h}$ can be independently H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, heterocyclyl, a nitrogen protecting group when attached to a nitrogen atom, or an oxygen protecting group when attached to an oxygen atom. In certain embodiments, $R^6$ can be —N($R^{6h}$)—C(=O)—$R^{6h}$, —N($R^{6h}$)—C(=O)—O$R^{6h}$, or —N($R^{6h}$)—C(=O)—N($R^{6h}$)$_2$.

In certain embodiments, $R^6$ can be substituted or unsubstituted carbamoyl. In certain embodiments, $R^6$ can be —OC(=O)N($R^{6j}$)$_2$, wherein each instance of $R^{6j}$ can be independently H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, heterocyclyl, or a nitrogen protecting group. In certain embodiments, $R^6$ can be —OC(=O)NH (nitrogen protecting group), wherein the nitrogen protecting group can be Bn, Boc, Cbz, Fmoc, trifluoroacetyl, triphenylmethyl, acetyl, or Ts. In certain embodiments, $R^6$ can be unsubstituted carbamoyl (i.e., —OC(=O)NH$_2$).

In certain embodiments, $R^6$ can be substituted or unsubstituted sulfonamido. In certain embodiments, $R^6$ can be —N($R^{6k}$)S(=O)$_2$$R^{6k}$, —N($R^{6k}$)S(=O)$_2$O$R^{6k}$, or —N($R^{6k}$)S(=O)$_2$N($R^{6k}$)$_2$, wherein each instance of $R^{6k}$ can be independently H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, heterocyclyl, a nitrogen protecting group when attached to a nitrogen atom, or an oxygen protecting group when attached to an oxygen group. In certain embodiments, $R^6$ can be —N($R^{6k}$)S(=O)$_2$$R^{6k}$, —N($R^{6k}$)S(=O)$_2$O$R^{6k}$, or —N($R^{6k}$)S(=O)$_2$N($R^{6k}$)$_2$.

In certain embodiments, $R^6$ can be substituted or unsubstituted $C_{1-6}$ alkyl or substituted or unsubstituted cycloalkyl.

In certain embodiments, the compound of Formula (I) can be of Formula (III), or a pharmaceutically acceptable salt, solvate, hydrate, polymorph, co-crystal, tautomer, stereoisomer, isotopically labeled derivative, or prodrug thereof, wherein $R^1$ can be as described herein. In certain embodiments, the present invention provides the compounds of Formula (III), or pharmaceutically acceptable salts thereof.

The compounds of Formula (III) include substituent $R^7$. In certain embodiments, $R^7$ can be H. In certain embodiments, $R^7$ can be substituted or unsubstituted, branched or unbranched alkyl. In certain embodiments, $R^7$ can be fluoroalkyl (e.g., perfluoroalkyl), chloroalkyl, bromoalkyl, or iodoalkyl. In certain embodiments, $R^7$ can be $C_{1-12}$ alkyl or $C_{1-6}$ alkyl (e.g., methyl, ethyl, propyl, butyl, pentyl, or hexyl).

In certain embodiments, $R^7$ can be substituted or unsubstituted, branched or unbranched alkenyl (e.g., vinyl).

In certain embodiments, $R^7$ can be substituted or unsubstituted, branched or unbranched alkynyl (e.g., ethynyl).

In certain embodiments, $R^7$ can be substituted or unsubstituted aralkyl. In certain embodiments, $R^7$ can be aralkyl, wherein the alkyl portion of aralkyl can be substituted or unsubstituted alkyl, such as $C_{1-12}$ or $C_{1-6}$ alkyl (e.g., methyl, ethyl, propyl, butyl, pentyl, or hexyl). In certain embodiments, $R^7$ can be aralkyl, wherein the aryl portion of aralkyl can be substituted or unsubstituted aryl. In certain embodiments, $R^7$ can be aralkyl, wherein the aryl portion of aralkyl can be 6- to 14-membered or 6- to 10-membered aryl. In certain embodiments, $R^7$ can be aralkyl, wherein the aryl portion of aralkyl can be monocyclic (e.g., phenyl) or bicyclic (e.g., naphthyl) aryl. In certain embodiments, $R^7$ can be substituted or unsubstituted Bn.

In certain embodiments, $R^7$ can be substituted or unsubstituted acyl. In certain embodiments, $R^7$ can be C(=O)—$R^{7a}$, wherein $R^{7a}$ can be H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, or heterocyclyl. In certain embodiments, $R^7$ can be

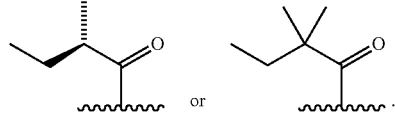

In certain embodiments, R can be —C(=O)—O$R^{7b}$, wherein $R^{7b}$ can be H, alkyl, alkenyl, alkynyl, aryl (e.g., phenyl), heteroaryl, cycloalkyl, cycloalkenyl, aralkyl (e.g., benzyl), aralkenyl, aralkynyl, heteroaralkyl, heteroaralkenyl, heteroaralkynyl, heterocyclyl, or an oxygen protecting group. In certain embodiments, $R^7$ can be —C(=O)O-(oxygen protecting group), wherein the oxygen protecting group can be silyl, TBDPS, TBDMS, TIPS, TES, TMS, MOM, THP, t-Bu, Bn, allyl, acetyl, pivaloyl, or benzoyl. In certain embodiments, $R^7$ can be —C(=O)OH.

The compounds of Formula (III) include substituent $R^8$. In certain embodiments, $R^8$ can be H, methyl, or hydroxyl.

In certain embodiments, n can be 1; the bond between C6 and C7 can be a single bond; all of U, X, Y, and Z can be carbon; $R^1$ can be —OH; $R^2$ and $R^3$ can be connected to form substituted or unsubstituted, 3- to 7-membered, monocyclic carbocycle including zero, one, or two double bonds in the carbocyclic ring; both $R^4$ and $R^5$ can be H; $R^6$ can be substituted or unsubstituted $C_{1-6}$ alkyl; and $R^7$ can be substituted or unsubstituted acyl. In certain embodiments, n can be 1; the bond between C6 and C7 can be a single bond; all of U, X, Y, and Z can be carbon; $R^1$ can be —OH; $R^2$ and $R^3$ can be connected to form substituted or unsubstituted cyclohexenyl; both $R^4$ and $R^5$ can be H; $R^6$ can be unsubstituted $C_{1-6}$ alkyl; and $R^7$ can be —C(=O)(substituted or unsubstituted $C_{1-6}$ alkyl). In certain embodiments, n can be 1; the bond between C6 and C7 can be a single bond; all of U, X, Y, and Z can be carbon; $R^1$ can be —OH; $R^2$ and $R^3$ can be connected to form substituted cyclohexenyl; both $R^4$ and $R^5$ can be H; $R^6$ can be methyl; $R^7$ can be —C(=O)(unsubstituted $C_{1-6}$ alkyl); and $R^8$ can be methyl. In certain embodiments, n can be 1; the bond between C6 and C7 can be a single bond; all of U, X, Y, and Z can be carbon; $R^1$ can be —OH; $R^2$ and $R^3$ can be connected to form substituted cyclohexenyl; both $R^4$ and $R^5$ can be H; $R^6$ can be methyl; $R^7$ can be —C(=O)(unsubstituted $C_{1-6}$ alkyl); and $R^8$ can be H or —OH.

In certain embodiments, n can be 1; the bond between C6 and C7 can be a single bond; all of U, X, Y, and Z can be carbon; $R^1$ can be —OCH$_2$ (substituted or unsubstituted phenyl); $R^2$ and $R^3$ can be connected to form substituted or unsubstituted, 3- to 7-membered, monocyclic carbocycle including zero, one, or two double bonds in the carbocyclic ring; both $R^4$ and $R^5$ can be H; $R^6$ can be substituted or unsubstituted $C_{1-6}$ alkyl; and $R^7$ can be substituted or unsubstituted acyl. In certain embodiments, n can be 1; the bond between C6 and C7 can be a single bond; all of U, X, Y, and Z can be carbon; $R^1$ can be

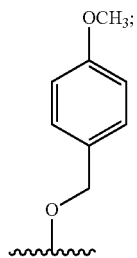

$R^2$ and $R^3$ can be connected to form substituted cyclohexenyl; both $R^4$ and $R^5$ can be H; $R^6$ can be unsubstituted $C_{1-6}$ alkyl; and $R^7$ can be —C(=O)(unsubstituted $C_{1-6}$ alkyl).

In certain embodiments, n can be 0; the bond between C6 and C7 can be a single bond; X can be nitrogen; all of Y, Z, and U can be carbon; $R^1$ can be —OCH$_2$ (substituted or unsubstituted phenyl); $R^2$ can be substituted or unsubstituted $C_{1-6}$ alkyl; $R^3$ can be —C(=O)N($R^{3c}$)$_2$; and both $R^4$ and $R^5$ can be substituted or unsubstituted 6- to 10-membered aryl. In certain embodiments, n can be 0; the bond between C6 and C7 can be a single bond; X can be nitrogen; all of Y, Z, and U can be carbon; $R^1$ can be

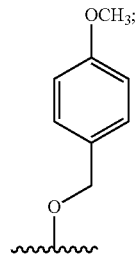

$R^2$ can be unsubstituted $C_{1-6}$ alkyl; $R^3$ can be —C(=O)NHPh; $R^4$ can be unsubstituted phenyl; and $R^5$ can be substituted or substituted phenyl (e.g., para-fluorophenyl).

In certain embodiments, n can be 0; the bond between C6 and C7 can be a double bond; Y can be nitrogen; all of X, Z, and U can be carbon; $R^1$ can be —OH; $R^2$ can be substituted or unsubstituted $C_{1-6}$ alkyl; $R^3$ and $R^4$ can be connected to form substituted or unsubstituted phenyl; and $R^5$ can be substituted or unsubstituted phenyl. In certain embodiments, n can be 0; the bond between C6 and C7 can be a double bond; Y can be nitrogen; all of X, Z, and U can be carbon; $R^1$ can be —OH; $R^2$ can be unsubstituted $C_{1-6}$ alkyl; $R^3$ and $R^4$ can be connected to form unsubstituted phenyl; and $R^5$ can be substituted or unsubstituted phenyl (e.g., para-fluorophenyl).

In certain embodiments, n can be 0; the bond between C6 and C7 can be a double bond; Y can be nitrogen; all of X, Z, and U can be carbon; $R^1$ can be —OCH$_2$ (substituted or unsubstituted phenyl); $R^2$ can be substituted or unsubstituted $C_{1-6}$ alkyl; $R^3$ and $R^4$ can be connected to form substituted or unsubstituted phenyl; and $R^5$ can be substituted or unsubstituted phenyl. In certain embodiments, n can be 0; the bond between C6 and C7 can be a double bond; Y can be nitrogen; all of X, Z, and U can be carbon; $R^1$ can be

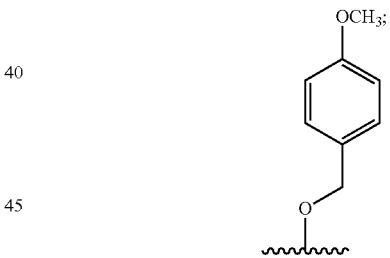

$R^2$ can be unsubstituted $C_{1-6}$ alkyl; $R^3$ and $R^4$ can be connected to form unsubstituted phenyl; and $R^5$ can be substituted or unsubstituted phenyl (e.g., para-fluorophenyl).

In certain embodiments, n can be 1; the bond between C6 and C7 can be a double bond; both X and Y can be carbon; both Z and U can be nitrogen; $R^1$ can be —OH; $R^2$ can be substituted or unsubstituted phenyl; $R^3$ can be null; $R^4$ can be substituted or unsubstituted sulfonamido; $R^5$ can be null; and $R^6$ can be substituted or unsubstituted $C_{1-6}$ alkyl. In certain embodiments, n can be 1; the bond between C6 and C7 can be a double bond; both X and Y can be carbon; both Z and U can be nitrogen; $R^1$ can be —OH; $R^2$ can be substituted or unsubstituted phenyl (e.g., para-fluorophenyl); $R^3$ can be null; $R^4$ can be —N(unsubstituted $C_{1-6}$ alkyl)S(=O)$_2$(unsubstituted $C_{1-6}$ alkyl); $R^5$ can be null; and $R^6$ can be unsubstituted $C_{1-6}$ alkyl.

In certain embodiments, n can be 1; the bond between C6 and C7 can be a double bond; both X and Y can be carbon; both Z and U can be nitrogen; $R^1$ can be —OCH$_2$ (substituted or unsubstituted phenyl); $R^2$ can be substituted or unsubstituted phenyl; $R^3$ can be null; $R^4$ can be substituted or unsubstituted sulfonamido; $R^5$ can be null; and $R^6$ can be substituted or unsubstituted $C_{1-6}$ alkyl. In certain embodiments, n can be 1; the bond between C6 and C7 can be a double bond; both X and Y can be carbon; both Z and U can be nitrogen; $R^1$ can be

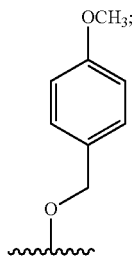

$R^2$ can be substituted or unsubstituted phenyl (e.g., para-fluorophenyl); $R^3$ can be null; $R^4$ can be —N(unsubstituted $C_{1-6}$ alkyl)S(=O)$_2$(unsubstituted $C_{1-6}$ alkyl); $R^5$ can be null; and $R^6$ can be unsubstituted $C_{1-6}$ alkyl.

In certain embodiments, n can be 1; the bond between C6 and C7 can be a double bond; all of X, Y, and Z can be carbon; U can be nitrogen; $R^1$ can be —OH; $R^2$ can be substituted or unsubstituted phenyl; all of $R^3$, $R^4$, and $R^6$ can be substituted or unsubstituted $C_{1-6}$ alkyl; and $R^5$ can be null. In certain embodiments, n can be 1; the bond between $C_6$ and $C_7$ can be a double bond; all of X, Y, and Z can be carbon; U can be nitrogen; $R^1$ can be —OH; $R^2$ can be substituted or unsubstituted phenyl (e.g., para-fluorophenyl); $R^3$ can be substituted or unsubstituted $C_{1-6}$ alkyl (e.g., methoxymethyl); both $R^4$ and $R^6$ can be unsubstituted $C_{1-6}$ alkyl; and $R^5$ can be null.

In certain embodiments, n can be 1; the bond between C6 and C7 can be a double bond; all of X, Y, and Z can be carbon; U can be nitrogen; $R^1$ can be —OCH$_2$(substituted or unsubstituted phenyl); $R^2$ can be substituted or unsubstituted phenyl; all of $R^3$, $R^4$, and $R^6$ can be substituted or unsubstituted $C_{1-6}$ alkyl; and $R^5$ can be null. In certain embodiments, n can be 1; the bond between C6 and C7 can be a double bond; all of X, Y, and Z can be carbon; U can be nitrogen; $R^1$ can be

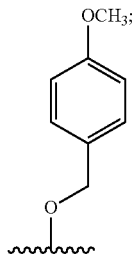

$R^2$ can be substituted or unsubstituted phenyl (e.g., para-fluorophenyl); $R^3$ can be substituted or unsubstituted $C_{1-6}$ alkyl (e.g., methoxymethyl); both $R^4$ and $R^6$ can be unsubstituted $C_{1-6}$ alkyl; and $R^5$ can be null.

In certain embodiments, n can be 1; the bond between C6 and C7 can be a double bond; all of X, Y, and Z can be carbon; U can be nitrogen; $R^1$ can be —OH; $R^2$ can be substituted or unsubstituted phenyl; $R^3$ and $R^4$ can be connected to form substituted or unsubstituted phenyl; $R^5$ can be null; and $R^6$ can be substituted or unsubstituted, 3- to 7-membered, monocyclic cycloalkyl. In certain embodiments, n can be 1; the bond between C6 and C7 can be a double bond; all of X, Y, and Z can be carbon; U can be nitrogen; $R^1$ can be —OH; $R^2$ can be substituted or unsubstituted phenyl (e.g., para-fluorophenyl); $R^3$ and $R^4$ can be connected to form unsubstituted phenyl; $R^5$ can be null; and $R^6$ can be unsubstituted, 3- to 7-membered, monocyclic cycloalkyl.

In certain embodiments, n can be 1; the bond between C6 and C7 can be a double bond; all of X, Y, and Z can be carbon; U can be nitrogen; $R^1$ can be —OCH$_2$(substituted or unsubstituted phenyl); $R^2$ can be substituted or unsubstituted phenyl; $R^3$ and $R^4$ can be connected to form substituted or unsubstituted phenyl; $R^5$ can be null; and $R^6$ can be substituted or unsubstituted, 3- to 7-membered, monocyclic cycloalkyl. In certain embodiments, n can be 1; the bond between C6 and C7 can be a double bond; all of X, Y, and Z can be carbon; U can be nitrogen; $R^1$ can be

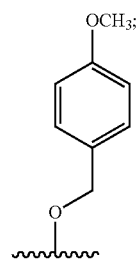

$R^2$ can be substituted or unsubstituted phenyl (e.g., para-fluorophenyl); $R^3$ and $R^4$ can be connected to form unsubstituted phenyl; $R^5$ can be null; and $R^6$ can be unsubstituted, 3- to 7-membered, monocyclic cycloalkyl.

In certain embodiments, the compound of Formula (III) can be selected from the group consisting of:

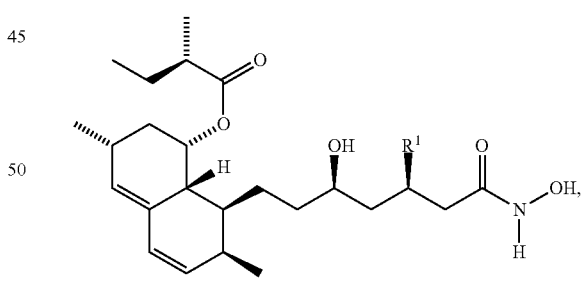

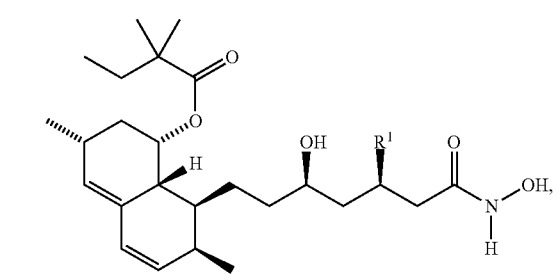

-continued

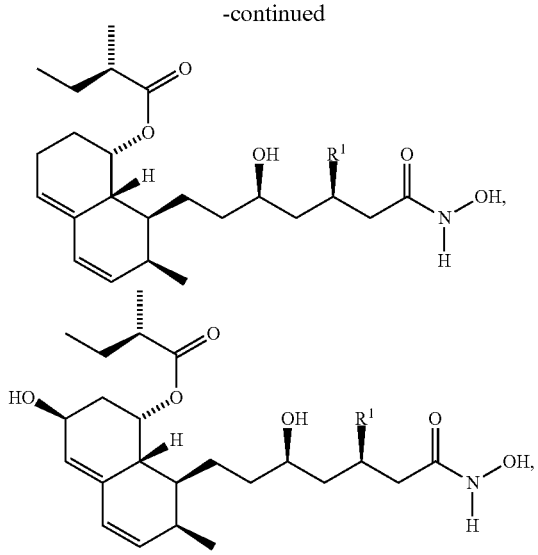

and a pharmaceutically acceptable salt, solvate, hydrate, polymorph, co-crystal, tautomer, stereoisomer, isotopically labeled derivative, or prodrug thereof; wherein $R^1$ is selected from the group consisting of $C_{1-6}$ alkyl, alkenyl, alkynyl, fluoroalkyl, chloroalkyl, bromoalkyl, iodoalkyl, perfluoroalkyl, aryl, heteroaryl, cycloalkyl, cycloalkenyl, aralkyl, aralkenyl, aralkynyl, heteroaralkyl, heteroaralkenyl, heteroaralkynyl, heterocyclyl, acyl, aminocarbonyl, amino, hydroxyl, alkoxy, acyloxy, silyloxy, amido, carbamoyl, and sulfonamido.

In certain embodiments, the compound of Formula (III) can be a 3,5,N-trihydroxy-alkanamide derivative selected from the group consisting of compounds 1, 2, 3, 4, and a pharmaceutically acceptable salt, solvate, hydrate, polymorph, co-crystal, tautomer, stereoisomer, isotopically labeled derivative, and prodrug thereof.

In certain embodiments, the compound of Formula (III) can be a 3-O-(p-methoxybenzyl) derivative selected from the group consisting of compounds 10, 12, 13, 14, and a pharmaceutically acceptable salt, solvate, hydrate, polymorph, co-crystal, tautomer, stereoisomer, isotopically labeled derivative, and prodrug thereof.

In certain embodiments, the compound of Formula (IV) can be compound 5 (which is a 3,5,N-trihydroxy-alkanamide derivative), or a pharmaceutically acceptable salt, solvate, hydrate, polymorph, co-crystal, tautomer, stereoisomer, isotopically labeled derivative, or prodrug thereof.

In certain embodiments, the compound of Formula (I) can be of Formula (V), or a pharmaceutically acceptable salt, solvate, hydrate, polymorph, co-crystal, tautomer, stereoisomer, isotopically labeled derivative, or prodrug thereof; wherein $R^1$ is selected from the group consisting of $C_{1-6}$ alkyl, alkenyl, alkynyl, fluoroalkyl, chloroalkyl, bromoalkyl, iodoalkyl, perfluoroalkyl, aryl, heteroaryl, cycloalkyl, cycloalkenyl, aralkyl, aralkenyl, aralkynyl, heteroaralkyl, heteroaralkenyl, heteroaralkynyl, heterocyclyl, acyl, aminocarbonyl, amino, hydroxyl, alkoxy, acyloxy, silyloxy, amido, carbamoyl, and sulfonamido.

In certain embodiments, the present invention provides the compounds of Formula (V), and pharmaceutically acceptable salts thereof.

In certain embodiments, the compound of Formula (I) can be of Formula (VII), or a pharmaceutically acceptable salt, solvate, hydrate, polymorph, co-crystal, tautomer, stereoisomer, isotopically labeled derivative, or prodrug thereof; wherein $R^1$ is selected from the group consisting of $C_{1-6}$ alkyl, alkenyl, alkynyl, fluoroalkyl, chloroalkyl, bromoalkyl, iodoalkyl, perfluoroalkyl, aryl, heteroaryl, cycloalkyl, cycloalkenyl, aralkyl, aralkenyl, aralkynyl, heteroaralkyl, heteroaralkenyl, heteroaralkynyl, heterocyclyl, acyl, aminocarbonyl, amino, hydroxyl, alkoxy, acyloxy, silyloxy, amido, carbamoyl, and sulfonamido.

In certain embodiments, the present invention provides the compounds of Formula (VII), and pharmaceutically acceptable salts thereof.

In certain embodiments, the compound of Formula (I) can be of Formula (VIII), or a pharmaceutically acceptable salt, solvate, hydrate, polymorph, co-crystal, tautomer, stereoisomer, isotopically labeled derivative, or prodrug thereof; wherein $R^1$ is selected from the group consisting of $C_{1-6}$ alkyl, alkenyl, alkynyl, fluoroalkyl, chloroalkyl, bromoalkyl, iodoalkyl, perfluoroalkyl, aryl, heteroaryl, cycloalkyl, cycloalkenyl, aralkyl, aralkenyl, aralkynyl, heteroaralkyl, heteroaralkenyl, heteroaralkynyl, heterocyclyl, acyl, aminocarbonyl, amino, hydroxyl, alkoxy, acyloxy, silyloxy, amido, carbamoyl, and sulfonamido.

In certain embodiments, the present invention provides the compounds of Formula (VIII), and pharmaceutically acceptable salts thereof.

In certain embodiments, the compound of Formula (V) can be compound 6 (which is a 3,5,N-trihydroxy-6-alkenamide derivative), or a pharmaceutically acceptable salt, solvate, hydrate, polymorph, co-crystal, tautomer, stereoisomer, isotopically labeled derivative, or prodrug thereof.

In certain embodiments, the compound of Formula (VII) can be compound 9 (which is a 3,5,N-trihydroxy-6-alkenamide derivative), or a pharmaceutically acceptable salt, solvate, hydrate, polymorph, co-crystal, tautomer, stereoisomer, isotopically labeled derivative, or prodrug thereof.

In certain embodiments, the compound of Formula (VIII) can be compound 8 (which is a 3,5,N-trihydroxy-6-alkenamide derivative), or a pharmaceutically acceptable salt, solvate, hydrate, polymorph, co-crystal, tautomer, stereoisomer, isotopically labeled derivative, or prodrug thereof.

In certain embodiments, the compound of Formula (V) can be compound 15 (which is a p-methoxybenzyl derivative), or a pharmaceutically acceptable salt, solvate, hydrate, polymorph, co-crystal, tautomer, stereoisomer, isotopically labeled derivative, or prodrug thereof.

In certain embodiments, the compound of Formula (VII) can be compound 17 (which is a p-methoxybenzyl derivative), or a pharmaceutically acceptable salt, solvate, hydrate, polymorph, co-crystal, tautomer, stereoisomer, isotopically labeled derivative, or prodrug thereof.

In certain embodiments, the compound of Formula (VIII) can be compound 16 (which is a p-methoxybenzyl derivative), or a pharmaceutically acceptable salt, solvate, hydrate, polymorph, co-crystal, tautomer, stereoisomer, isotopically labeled derivative, or prodrug thereof.

In certain embodiments, the compound of Formula (I) can be of the formula:

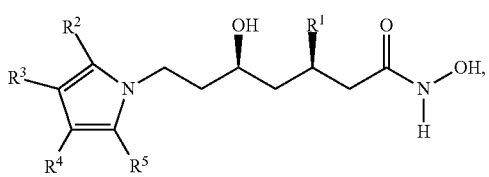

or a pharmaceutically acceptable salt, solvate, hydrate, polymorph, co-crystal, tautomer, stereoisomer, isotopically labeled derivative, or prodrug thereof, wherein $R^1$, $R^2$, $R^3$, $R^4$, and $R^5$ are as described herein.

In certain embodiments, the compound of Formula (I) can be of Formula (IV), or a pharmaceutically acceptable salt, solvate, hydrate, polymorph, co-crystal, tautomer, stereoisomer, isotopically labeled derivative, or prodrug thereof; wherein $R^1$ is selected from the group consisting of $C_{1-6}$ alkyl, alkenyl, alkynyl, fluoroalkyl, chloroalkyl, bromoalkyl, iodoalkyl, perfluoroalkyl, aryl, heteroaryl, cycloalkyl, cycloalkenyl, aralkyl, aralkenyl, aralkynyl, heteroaralkyl, heteroaralkenyl, heteroaralkynyl, heterocyclyl, acyl, aminocarbonyl, amino, alkoxy, acyloxy, silyloxy, amido, carbamoyl, and sulfonamido.

In certain embodiments, the present invention provides the compounds of Formula (IV), and pharmaceutically acceptable salts thereof.

In certain embodiments, the compound of Formula (IV) can be compound 11 (which is a 3-O-(p-methoxybenzyl) derivative), or a pharmaceutically acceptable salt, solvate, hydrate, polymorph, co-crystal, tautomer, stereoisomer, isotopically labeled derivative, or prodrug thereof.

In certain embodiments, the compound of Formula (I) can be of Formula (VI), or a pharmaceutically acceptable salt, solvate, hydrate, polymorph, co-crystal, tautomer, stereoisomer, isotopically labeled derivative, or prodrug thereof; wherein $R^1$ is selected from the group consisting of $C_{1-6}$ alkyl, alkenyl, alkynyl, fluoroalkyl, chloroalkyl, bromoalkyl, iodoalkyl, perfluoroalkyl, aryl, heteroaryl, cycloalkyl, cycloalkenyl, aralkyl, aralkenyl, aralkynyl, heteroaralkyl, heteroaralkenyl, heteroaralkynyl, heterocyclyl, acyl, aminocarbonyl, amino, hydroxyl, alkoxy, acyloxy, silyloxy, amido, carbamoyl, and sulfonamide.

In certain embodiments, the present invention provides the compounds of Formula (VI), and pharmaceutically acceptable salts thereof.

In certain embodiments, the compound of Formula (VI) can be compound 7 or 18 (each of which is a 3,5,N-trihydroxy-6-alkenamide derivative), or a pharmaceutically acceptable salt, solvate, hydrate, polymorph, co-crystal, tautomer, stereoisomer, isotopically labeled derivative, or prodrug thereof.

In certain embodiments, n can be 1; and $R^4$ cannot be sulfonamido. In certain embodiments, n can be 1; and at least one of U and Z can be carbon. In certain embodiments, n can be 0; and X can be carbon. In certain embodiments, n can be 0; and at least one of U and Y can be nitrogen. In certain embodiments, n can be 0; and $R^3$ can be null, $C_{1-6}$ alkyl, alkenyl, alkynyl, fluoroalkyl, chloroalkyl, bromoalkyl, iodoalkyl, perfluoroalkyl, aryl, heteroaryl, cycloalkyl, cycloalkenyl, aralkyl, aralkenyl, aralkynyl, heteroaralkyl, heteroaralkenyl, heteroaralkynyl, heterocyclyl, aminocarbonyl, amino, hydroxyl, alkoxy, acyloxy, silyloxy, amido, carbamoyl, or sulfonamido, or $R^3$ can be connected with $R^2$ or $R^4$ to form carbocycle or heterocycle. In certain embodiments, n can be 0; and $R^4$ can be $C_{1-6}$ alkyl, alkenyl, alkynyl, fluoroalkyl, chloroalkyl, bromoalkyl, iodoalkyl, perfluoroalkyl, heteroaryl, cycloalkyl, cycloalkenyl, aralkyl, aralkenyl, aralkynyl, heteroaralkyl, heteroaralkenyl, heteroaralkynyl, heterocyclyl, acyl, aminocarbonyl, amino, hydroxyl, alkoxy, acyloxy, silyloxy, amido, carbamoyl, or sulfonamido, or $R^4$ can be connected with $R^3$ to form carbocycle or heterocycle. In certain embodiments, the compound of Formula (I) can be of the formula:

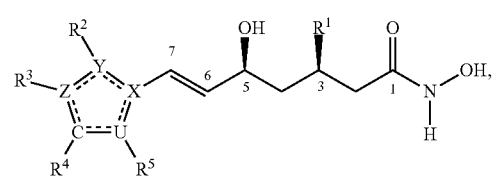

or a pharmaceutically acceptable salt, solvate, hydrate, polymorph, co-crystal, tautomer, stereoisomer, isotopically labeled derivative, or prodrug thereof.

Exemplary hexanohydroxamic acid derivative compounds described here include, but are not limited to:

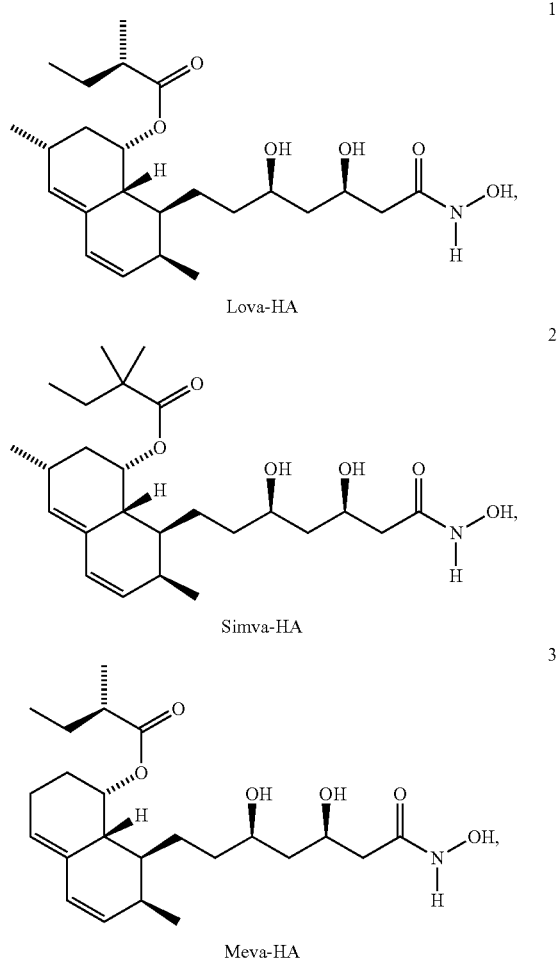

-continued
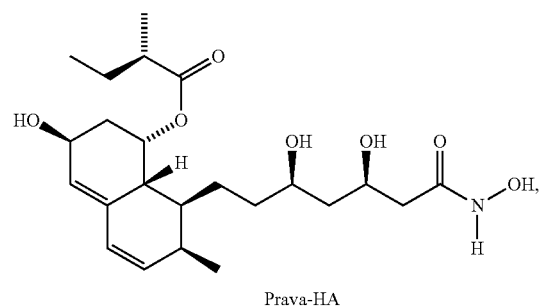
Prava-HA
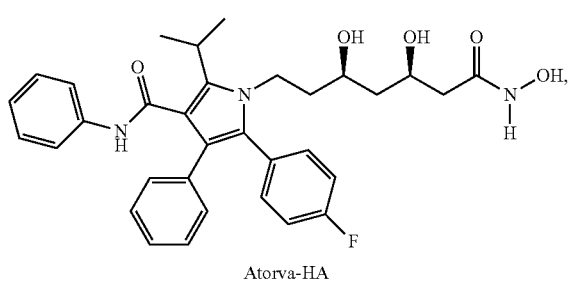
Atorva-HA
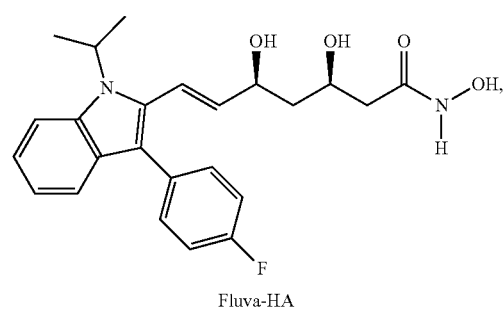
Fluva-HA
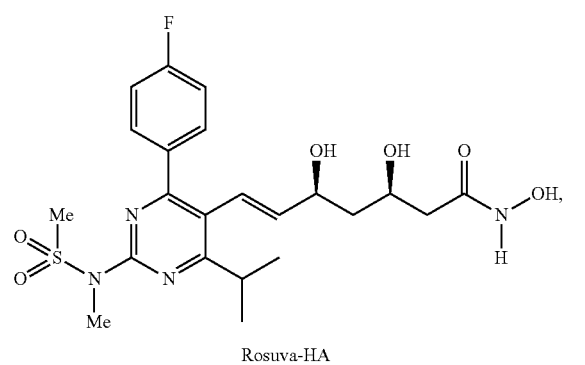
Rosuva-HA
-continued
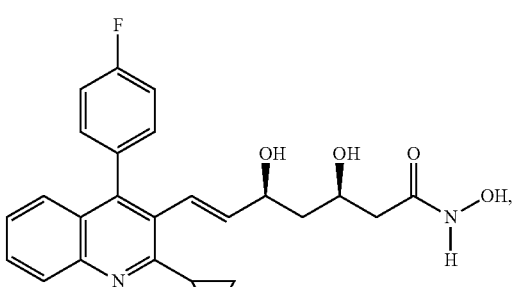
Pitava-HA
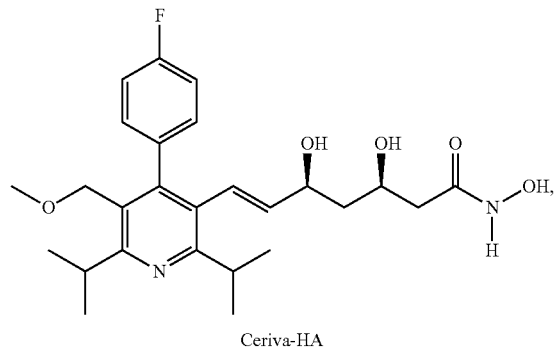
Ceriva-HA
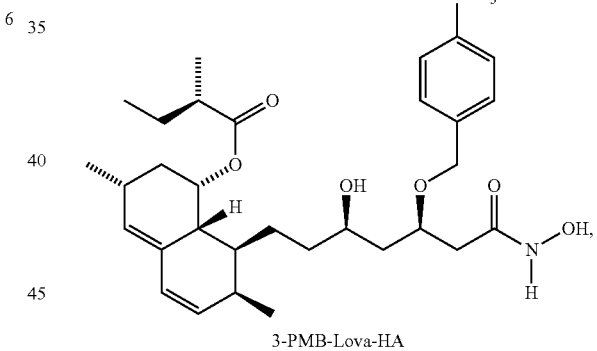
3-PMB-Lova-HA
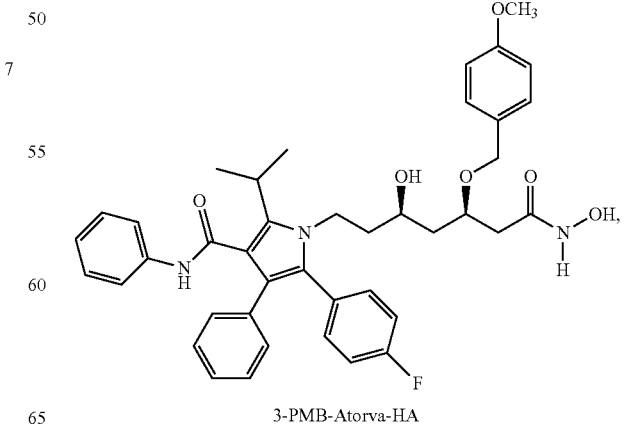
3-PMB-Atorva-HA In certain embodiments, compounds of the invention are the compounds described herein, and pharmaceutically acceptable salts, solvates, hydrates, polymorphs, co-crystals, tautomers, stereoisomers, isotopically labeled derivatives, and prodrugs thereof. In certain embodiments, compounds of the invention are the compounds described herein, and pharmaceutically acceptable salts, solvates, derivatives, and prodrugs thereof. In certain embodiments, compounds of the invention are the compounds described herein, and pharmaceutically acceptable salts, solvates, and prodrugs thereof. In certain embodiments, compounds of the invention are the compounds described herein, and pharmaceutically acceptable salts thereof. In certain embodiments, compounds of the invention are the compounds of any one of Formulae (I) and (III) to (VIII), and pharmaceutically acceptable salts, solvates, hydrates, polymorphs, co-crystals, tautomers, stereoisomers, isotopically labeled derivatives, and prodrugs thereof. In certain embodiments, compounds of the invention are the compounds of any one of Formulae (I) and (III) to (VIII), and pharmaceutically acceptable salts thereof.

Compounds of the invention are inhibitors of an HDAC (e.g., HDAC1, HDAC2, HDAC3, HDAC4, HDAC5, HDAC6, HDAC7, HDAC8, HDAC9, HDAC10, HDAC11, SIRT1, SIRT2, SIRT3, SIRT4, SIRT5, SIRT6, SIRT7). In certain embodiments, the compounds of the invention (e.g., compounds 1, 2, 5, and 7) inhibit the activity of HDAC1. In certain embodiments, the compounds of the invention (e.g., compounds 1, 2, 5, and 7) inhibit the activity of HDAC2. In certain embodiments, the compounds of the invention (e.g., compounds 1, 2, 5, and 7) inhibit the activity of HDAC6. Compounds of the invention (e.g., compounds 1, 2, 5, and 7) are also inhibitors of HMGR.

In certain embodiments, the activity of the HDAC and/or HMGR is inhibited by the inventive compounds. The inhibition of the activity of the HDAC and/or HMGR by an inventive compound may be measured by the half maximal inhibitory concentrations ($IC_{50}$) value of a compound of the invention when the inventive compound, or a pharmaceutical composition thereof, is contacted, directly or indirectly, with the HDAC and/or HMGR. In certain embodiments, the $IC_{50}$ value of a compound of the invention is at most about 1 mM, at most about 300 µM, at most about 100 µM, at most about 30 µM, at most about 10 µM, at most about 3 µM, at most about 1 µM, at most about 300 nM, at most about 100 nM, at most about 30 nM, at most about 10 nM, at most about 3 nM, or at most about 1 nM. In certain embodiments, the $IC_{50}$ value of a compound of the invention is at least about 1 nM, at least about 3 nM, at least about 10 nM, at least about 30 nM, at least about 100 nM, at least about 300 nM, at least about 1 µM, at least about 3 µM, at least about 10 µM, at least about 30 µM, at least about 100 µM, at least about 300 µM, or at least 1 mM. Combinations of the above-referenced ranges (e.g., at most about 30 µM and at least about 3 nM) are also contemplated to be within the scope of the invention. Other ranges are also possible.

The compounds of the invention may selectively inhibit the activity of an HDAC and/or HMGR. In certain embodiments, the inventive compounds that selectively inhibit the activity of the HDAC and/or HMGR show a greater inhibitory activity against the HDAC and/or HMGR than against one or more other proteins or one or more other HDAC.

The selectivity of an inventive compound for an HDAC and/or HMGR over another protein or another HDAC may be measured by the quotient of the $IC_{50}$ value of the inventive compound in inhibiting the activity of the another protein or another HDAC over the $IC_{50}$ value of the inventive compound in inhibiting the activity of the HDAC and/or HMGR. In certain embodiments, the selectivity is at least about 1-fold, at least about 3-fold, at least about 10-fold, at least about 30-fold, at least about 50-fold, at least about 100-fold, at least about 300-fold, at least about 1,000-fold, or at least about 10,000-fold. In certain embodiments, the selectivity is at most about 1,000-fold, at most about 300-fold, at most about 100-fold, at most about 30-fold, at most about 10-fold, at most about 3-fold, or at most about 1-fold. Combinations of the above-referenced ranges (e.g., and at least about 3-fold and at most about 300-fold) are also contemplated to be within the scope of the invention. Other ranges are also possible. In certain embodiments, the compounds of the invention selectively inhibit an HDAC described herein (e.g., HDAC1, HDAC2, HDAC6). In certain embodiments, the compounds of the invention selectively inhibit HMGR. In certain embodiments, the compounds of the invention selectively inhibit an HDAC described herein and HMGR.

II. Methods of Preparing the Compounds

Any of the compounds described herein can be prepared by routine methods known in the art. For example, one can use synthetic chemistry transformations (including protecting group methodologies), e.g., those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

In some embodiments, a compound as described herein (e.g., compounds of Formula (I), can be prepared by treating (e.g., contacting) a lactone (II), or a salt thereof, with hydroxylamine, or a salt thereof:

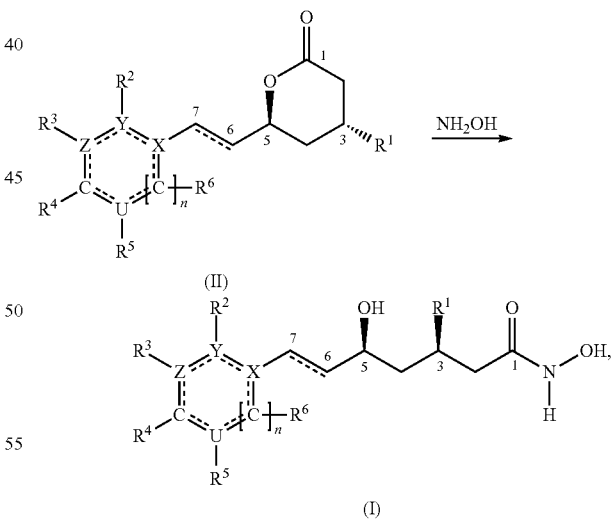

wherein:
n represents 0 or 1;
X, Y, Z, and U are independently selected from the group consisting of carbon and nitrogen;
══ represents a single or double bond;
$R^1$, $R^2$, $R^3$, $R^4$, $R^5$ and $R^6$ are substituents independently selected from the group consisting of $C_{1-6}$ alkyl, alkenyl, alkynyl, fluoroalkyl, chloroalkyl, bromoalkyl, iodoalkyl, perfluoroalkyl, aryl, heteroaryl, cycloalkyl, cycloalkenyl, aralkyl, aralkenyl, aralkynyl, heteroaralkyl, heteroaralkenyl, heteroaralkynyl, heterocyclyl, acyl, aminocarbonyl, amino, hydroxyl, alkoxy, acyloxy, silyloxy, amido, carbamoyl, and sulfonamido; and $R^3$ is optionally connected with $R^2$ or $R^4$ to form carbocycle or heterocycle.

In certain embodiments, n, X, Y, Z, U, ═══, $R^1$, $R^2$, $R^3$, $R^4$, $R^5$ and $R^6$ are as described herein. In certain embodiments, X can be carbon; and all of Y, Z, and U can independently be carbon or nitrogen; with the proviso that the bond between C6 and C7 can be a double bond when Y is carbon and both Z and U are nitrogen.

Hydroxylamine can be a solution or generated in situ from a salt of hydroxylamine with a base. The salt is selected from a group consisting of hydrochloride, nitrate, phosphate, and sulfate salts. The base is selected from a group consisting of hydroxide, carbonate, bicarbonate, methoxide, ethoxide, isopropoxide, and tert-butoxide with the counter cation selected from a group consisting of lithium, sodium, potassium, cesium, calcium, and barium;

A Lewis acid can be used as a reaction promotor, which is selected from a group consisting of lithium, magnesium, calcium, zinc, aluminum, boron, indium, scandium, ytterbium, cerium, silicon, tin, titanium, zirconium, vanadium, iron, and cobalt salts with the counter anion selected from a group consisting of fluoride, chloride, bromide, iodide, hydroxide, methoxide, ethoxide, isoproproxide, tert-butoxide, acetate, oxalate, acetylacetonate, nitrate, phosphate, sulfate, bisulfate, and sulfonate.

The reaction (e.g., the step of contacting) can be conducted in a hydrocarbon, ethereal, chlorinated, and alcoholic solvent, or a mixture thereof (e.g., their co-solvent system in varied ratios). The hydrocarbon solvent comprises an acyclic, cyclic, or aromatic solvent selected from the group consisting of n-hexane, cyclohexane, benzene, toluene, and xylene. The ethereal solvent comprises an acyclic or cyclic solvent selected from the group consisting of diethyl ether, methyl tert-butyl ether, dimethoxyethane, tetrahydrofuran, and 1,4-dioxane.

Two conventional methods are often utilized to prepare N-hydroxyalkanamides: (1) condensation of alkanoic acids with hydroxylamine in the presence of an activating agent, such as ethyl chloroformate and (benzotriazol-1-yloxy) tripyrrolidinophosphonium hexafluorophosphate (PyBOP), and (2) reaction of ester or lactone with hydroxylamine hydrochloride in alkaline solution.

In an initial attempt to synthesize 3,5,N-trihydroxy-alkanamide, free hydroxylamine was prepared by neutralization of its hydrochloric salt with KOH or NaOMe in MeOH, and reacted in situ with lactone at ambient temperature. Though the desired product of was obtained according to the spectral analysis (MS, $^1$H and $^{13}$C NMR), this reaction was complicated by the competitive attacks of —OH and —OMe nucleophiles at the lactone group to give side products of carboxylic acid and its methyl ester.

To achieve a balance between activation of lactone (II) and nucleophilicity of hydroxylamine, compounds of Formula (I) may be prepared by using appropriate Lewis acids to promote the reaction. See, e.g., Scheme 1.

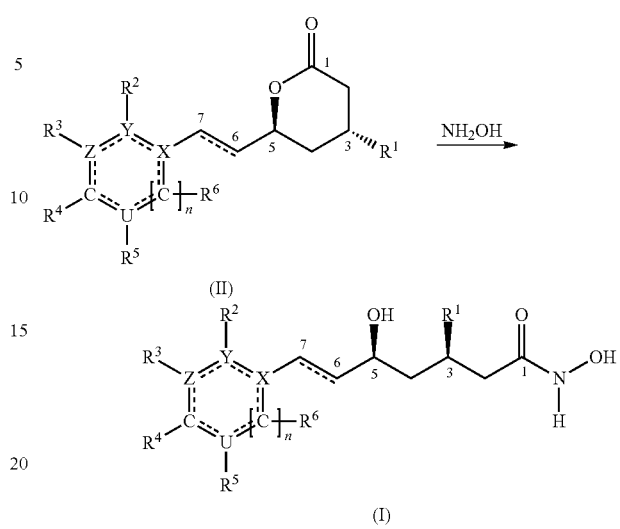

Scheme 1.

For example, sodium bicarbonate was used as a base for in situ neutralization of hydroxylamine hydrochloric salt in a mixed solvent of tetrahydrofuran and methanol, and lovastatin in the lactone form reacted smoothly in the presence of magnesium bromide to give Lova-HA (1) in 79% yield after chromatographic purification.

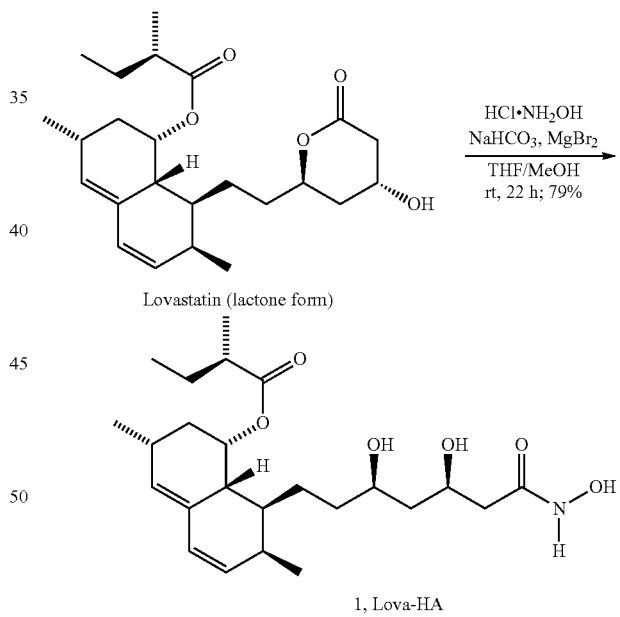

Lova-HA was considered a condensed dual-functional inhibitor of HMGR and HDAC. The hydroxamate group in Lova-HA (1) might act as an essential zinc-binding group for targeting HDAC, whereas the most structural elements in lovastatin were retained to assure its HMGR inhibitory activity.

By this approach, a variety of Formula (I) compounds were synthesized. The practical manufacture from representative HMGR inhibitors was carried out as shown. Two 3-O-(p-methoxybenzyl) derivatives were similarly prepared. The reactions were conducted in mild conditions to retain other functional groups such as an ester and C═C double bond.

Different from synthesis methods known in the art (see, e.g., Indian patent application IN2007-CH1492), the instant method is straightforward and efficient for the synthesis of Rosuva-HA, Lova-HA, Simva-HA and Fluva-HA. For example, the synthesis methods described herein do not require saturation of the C=C double bond in rosuvastatin or extra steps for protection-deprotection.

III. Pharmaceutical Compositions and Kits

Another aspect of the present disclosure relates to pharmaceutical compositions comprising one or more of the compounds as described herein (e.g., the 3,5,N-trihydroxy-alkanamide and 3,5,N-trihydroxy-6-alkenamide derivatives described herein such as Compounds 1-11), and optionally a pharmaceutically acceptable excipient.

Any of the pharmaceutical compositions described herein can be formulated for a suitable administration route, e.g., orally, parenterally, by inhalation spray, topically, rectally, nasally, buccally, vaginally or via an implanted reservoir. The term "parenteral" as includes subcutaneous, intracutaneous, intravenous, intramuscular, intraarticular, intraarterial, intrasynovial, intrasternal, intrathecal, intralesional and intracranial injection or infusion techniques.

A sterile injectable pharmaceutical composition, e.g., a sterile injectable aqueous or oleaginous suspension, can be formulated according to techniques known in the art using suitable dispersing or wetting agents (such as Tween® 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A pharmaceutical composition for oral administration can be any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation pharmaceutical composition can be prepared according to techniques well-known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art. A pharmaceutical composition of the invention can also be administered in the form of suppositories for rectal administration.

Pharmaceutically acceptable excipients that may be included in a pharmaceutical composition of the invention include inert diluents, solubilizing agents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the pharmaceutical composition.

An excipient present in an inventive pharmaceutical composition must be "pharmaceutically acceptable" in the sense that the excipient is compatible with the active ingredient of the pharmaceutical composition (and preferably, capable of stabilizing the pharmaceutical composition) and not deleterious to a subject to whom the pharmaceutical composition is administered. For example, solubilizing agents such as cyclodextrins, which may form specific, more soluble complexes with the compounds of the invention, can be utilized as pharmaceutically acceptable excipients for delivery of the compounds of the invention into the subject. Examples of other pharmaceutically acceptable excipients include colloidal silicon dioxide, magnesium stearate, cellulose, sodium lauryl sulfate, and D&C Yellow #10.

Also disclosure herein are kits (e.g., pharmaceutical packs) comprising one or more of the compounds or pharmaceutical compositions described herein, and a container (e.g., a vial, ampule, bottle, syringe, and/or dispenser package, or other suitable container). In some embodiments, the kits may include a second container comprising a pharmaceutically acceptable excipient for dilution or suspension of an inventive pharmaceutical composition or compound. In some embodiments, the inventive pharmaceutical composition or compound provided in the first container and the second container are combined to form one unit dosage form.

In certain embodiments, a kit as described herein is for use in inhibiting the activity of an HDAC, HMGR, or both in cells. In certain embodiments, a kit as described herein is for use in treating any of the target diseases as described herein, e.g., cancer, hypercholesterolemia, an acute or chronic inflammatory disease, autoimmune disease, allergic disease, pathogen infection, neurodegenerative disease, or a disease associated with oxidative stress) in a subject in need thereof, or inhibiting drug resistance of cancer cells.

Any of the kits described herein can thus include instructions for administering the compound or pharmaceutical composition contained therein. A kit of the invention may also include information as required by a regulatory agency such as the FDA. In certain embodiments, the information included in the kit is prescribing information. In certain embodiments, the kit and instructions provide for inhibiting the activity of HDAC. In certain embodiments, the kit and instructions provide for inhibiting the activity of HMGR. In certain embodiments, the kit and instructions provide for treating a disease described herein. In certain embodiments, the kit and instructions provide for preventing a disease described herein. A kit of the invention may include one or more additional pharmaceutical agents described herein as a separate composition.

IV. Methods of Treatment

Any of the compounds or pharmaceutical compositions described herein can be used for inhibiting the activity of an HDAC (e.g., HDAC1, HDAC2, and/or HDAC6), an HMGR, or both. They also can be used in treating a disease associated with HDAC or HMGR, including, but are not limited to, cancer, hypercholesterolemia, inflammatory diseases (e.g., acute or chronic), autoimmune diseases, allergic diseases, infectious diseases, neurodegenerative diseases, or diseases associated with oxidative stress.

In some embodiments, the treatment methods described herein can comprise administering to a subject in need of the treatment an effective amount of the pharmaceutical composition as described herein. The term "treating" or "treatment" as used herein refers to the application or administration of a pharmaceutical composition or compound as described herein to a subject, who has a disorder (e.g., cancer), a symptom of the disorder, a disease or disorder secondary to the disorder, or a predisposition toward the disorder, with the purpose to cure, alleviate, relieve, remedy, or ameliorate the disorder, the symptom of the disorder, the disease or disorder secondary to the disorder, or the predisposition toward the disorder.

A "subject" to be treated by any of the methods described herein can be a human subject (e.g., a pediatric subject such as an infant, a child, or an adolescent, or an adult subject such as a young adult, middle-aged adult, or senior adult), or a non-human animal, such as dogs, cats, cows, pigs, horses, sheep, goats, rodents (e.g., mice, rats), and non-human primates (e.g., cynomolgus monkeys, rhesus monkeys). The non-human mammal may be a transgenic animal or genetically engineered animal. In some examples, the subject is a human patient having a target disease as described herein (e.g., cancer), suspected of having the disease, or is at risk for the disease.

In some embodiments, the subject is a human or non-human mammal having, suspected of having, or at risk for cancer. The term "cancer" refers to a class of diseases characterized by the development of abnormal cells that proliferate uncontrollably and have the ability to infiltrate and destroy normal body tissues. The compounds described herein are useful in treating cancers of any type, particularly those that are associated with dysregulated HDAC and/or HMGR activity. Examples include, but are not limited to, leukemia, Hodgkin's disease, lymphoma, Ewing's sarcoma, multiple myeloma, Wilms' tumor, bone tumor, neuroblastoma, retinoblastoma, testicular cancer, thyroid cancer, prostate cancer, larynx cancer, cervical cancer, nasopharynx cancer, breast cancer, colon cancer, pancreatic cancer, head and neck cancer, esophageal cancer, rectal cancer, small-cell lung cancer, non-small-cell lung cancer, brain cancer, melanoma and other skin cancers, and CNS neoplasm.

In one example, the subject is a human patient having colon cancer. In another example, the subject is a human patient having lung cancer.

In other embodiments, the subject to be treated by a method as described herein can be a human or non-human mammal having, suspected of having, or at risk for hypercholesterolemia, which refers to the presence of high levels of cholesterol in the blood as compared to that in a healthy subject.

In yet other embodiments, the subject can be a human or non-human mammal having, suspected of having, or at risk for an inflammatory disease, which can be acute or chronic. The term "inflammatory disease" refers to a disease characterized by inflammation, including a dysregulated inflammatory reaction that causes an exaggerated response by macrophages, granulocytes, and/or T-lymphocytes leading to abnormal tissue damage and/or cell death. Exemplary inflammatory diseases include, but are not limited to, inflammatory bowel disease, necrotizing enterocolitis, and rheumatoid arthritis.

In addition, the subject to be treated by a method as described herein can be a human or non-human mammal having, suspected of having, or at risk for an autoimmune disease. The term "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). Exemplary autoimmune diseases include, but are not limited to, systemic lupus erythematosis, rheumatoid, arthritis, psoriasis, Crohn's disease, and multiple sclerosis.

The subject also can be a human or non-human mammal having, suspected of having, or at risk for an allergic disease (e.g., allergic bronchitis or asthma), an infectious disease (e.g., a disease caused by viral or bacterial infection), a neurodegenerative disease (e.g., Alzheimer's disease, Amyotrophic lateral sclerosis, Huntington's disease, and Parkinson's disease), or a disease associated with oxidative stress.

An "effective amount" of a compound described herein (either taken alone or in combination of another agent) refers to an amount sufficient to elicit the desired biological response, e.g., inhibiting an HDAC, HMGR, or both, or alleviating a target disease described herein or a symptom associated with the disease. As will be appreciated by those of ordinary skill in this art, the effective amount of a compound described herein may vary depending on such factors as the desired biological endpoint, the pharmacokinetics of the compound, the condition being treated, the mode of administration, and the age and health of a subject. In some examples, an effective amount can be a therapeutically effective amount, which refers to an amount of a therapeutic agent, alone or in combination with other therapies, sufficient to provide a therapeutic benefit in the treatment of a condition or to delay the onset or minimize one or more symptoms associated with the condition. The term "therapeutically effective amount" can encompass an amount that improves overall therapy, reduces or avoids symptoms, signs, or causes of the condition, and/or enhances the therapeutic efficacy of another therapeutic agent. In other examples, the effective amount can be a prophylactically effective amount. A prophylactically effective amount of a compound means an amount of a therapeutic agent, alone or in combination with other agents, which provides a prophylactic benefit in the prevention of the condition. For example, a "prophylactically effective amount" of a compound can be an amount sufficient to prevent or delay the onset of a condition, or one or more symptoms associated with the condition or prevent its recurrence. It may also be an amount that improves overall prophylaxis or enhances the prophylactic efficacy of another prophylactic agent.

In some examples, the method described herein is performed by administering one or more compounds or pharmaceutical compositions described herein to a subject in need of the treatment (e.g., any of the subject described herein such as a human cancer patient) in an amount effective in inhibiting the activity of an HDAC, HMGR, or both in the subject. In other examples, the compound(s) or pharmaceutical composition(s) is administered to the subject in an amount effective in treating a target disease as described herein, e.g., cancer or hypercholesterolemia.

An effective amount of a compound may vary from about 0.001 mg/kg to about 1000 mg/kg in one or more dose administrations for one or several days (depending on the mode of administration). In certain embodiments, the effective amount per dose varies from about 0.001 mg/kg to about 1000 mg/kg, from about 0.01 mg/kg to about 750 mg/kg, from about 0.1 mg/kg to about 500 mg/kg, from about 1.0 mg/kg to about 250 mg/kg, and from about 10.0 mg/kg to about 150 mg/kg.

The terms "administer," "administering," or "administration" refer to implanting, absorbing, ingesting, injecting, inhaling, or otherwise introducing a compound or pharmaceutical composition of the invention, in or on a subject. Any of the suitable administration routes can be used for delivering the compounds or pharmaceutical compositions described herein. Examples include, but are not limited to, orally, parenterally, by inhalation spray, topically, rectally, nasally, buccally, vaginally or via an implanted reservoir.

Also described herein are methods for inhibiting the activity of HDAC, HMGR or both in cells. Such method may comprise contacting one or more compounds as described herein with cells in an amount effective to inhibit the activity of HDAC (e.g., the activity of HDAC1, HDAC2, HDAC6, or a combination thereof), the activity of HMGR, or both. The amount of the one or more compounds can be sufficient to inhibit at least 20% (e.g., 30%, 40%, 50%, 60%, 70%, 80%, 90%, or 95%) of the enzymatic activity. In some embodiments, the methods can be performed in intro. In other embodiments, they can be performed in vivo by administering the compound to a subject in need of the treatment as described herein.

It will be also appreciated that a compound or pharmaceutical composition, as described herein, can be used in combination with one or more additional pharmaceutical agents (e.g., therapeutically and/or prophylactically active agents) in any of the methods described herein. The compounds or pharmaceutical compositions can be administered in combination with additional pharmaceutical agents that improve their activity (e.g., activity (e.g., potency and/or efficacy) in treating a disease described herein in a subject in need thereof, in preventing a disease described herein in a subject in need thereof, in inhibiting the activity of an HDAC in a subject or cell, in inhibiting the activity of HMGR in a subject or cell), bioavailability, and/or safety, reduce drug resistance, reduce and/or modify their metabolism, inhibit their excretion, and/or modify their distribution within the body of a subject. It will also be appreciated that the therapy employed may achieve a desired effect for the same disorder, and/or it may achieve different effects. In certain embodiments, an inventive pharmaceutical composition including a compound of the invention and an additional pharmaceutical agent shows a synergistic effect that is absent in a pharmaceutical composition including one of the compound and the additional pharmaceutical agent, but not both.

In some embodiments, the compound or pharmaceutical composition can be administered concurrently with, prior to, or subsequent to one or more additional pharmaceutical agents, which may be useful as, e.g., combination therapies. Pharmaceutical agents can be therapeutically active agents or prophylactically active agents. The additional pharmaceutical agents include, but are not limited to, anti-cancer agents, anti-angiogenesis agents, anti-inflammatory agents, immunosuppressants, anti-bacterial agents, anti-viral agents, anti-diabetic agents, anti-allergic agents, and pain-relieving agents. In certain embodiments, the additional pharmaceutical agent is an HDAC inhibitor or HMGR inhibitor different from the compound described herein. In certain embodiments, the compounds or pharmaceutical compositions described herein can be administered in combination with an anti-cancer therapy including, but not limited to, surgery, radiation therapy, and chemotherapy.

The compounds described herein are capable of reducing cancer cell resistance to anti-cancer drugs such as platinum-based antineoplastic agents, one or more compounds as described herein can be co-used with such anti-cancer drugs so as to improve their therapeutic efficacy via reduction of drug resistance, particularly under hypoxia conditions. In some examples, the anti-cancer drug for co-use with any of the compounds described herein (e.g., the compound described in Example 10 below) can be a platinum-based antineoplastic agent, e.g., oxaliplatin, cisplatin, carboplatin, satraplatin, picoplatin, nedaplatin, or triplatin.

Another aspect of the invention relates to methods of screening a library of compounds, and pharmaceutical acceptable salts thereof, to identify a compound, or a pharmaceutical acceptable salt thereof, which is useful in the methods of the invention. In certain embodiments, the methods of screening a library include obtaining at least two different compounds of the invention; and performing an assay using the different compounds of the invention. In certain embodiments, the assay is useful in identifying a compound that is useful in the inventive methods.

EXAMPLES

Without intent to limit the scope of the invention, exemplary compounds and methods of using or making such, as well as their related results according to the embodiments of the present invention are given below. Note that titles or subtitles may be used in the examples for convenience of a reader, which in no way should limit the scope of the invention. Moreover, certain theories are proposed and disclosed herein; however, in no way they, should limit the scope of the invention so long as the invention is practiced according to the invention without regard for any particular theory or scheme of action.

Example 1

Synthesis of Lova-HA ((3R,5R)-7-{(1S,2S,6R,8S,8aR)-Hexahydro-2,6-dimethyl-8-[2-methylbutyryloxy]naphthalenyl}-3,5-dihydroxy-N-hydroxyheptanamide) Instrumentation Melting points were recorded on a Yanaco or Electrothermal MEL-TEMP 1101D apparatus in open capillaries and are not corrected. Optical rotations were measured on digital polarimeter of Japan JASCO Co. DIP-1000. $[\alpha]_D$ values are given in units of $10^{-1}$ deg cm$^2$ g$^{-1}$ Infrared (IR) spectra were recorded on Nicolct Magna 550-11 or Thermo Nicolet 380 FT-IR spectrometers. UV-visible spectra were measured on a Perkin Elmer Lambda 35 spectrophotometer. Nuclear magnetic resonance (NMR) spectra were obtained on Bruker Advance-400 (400 MHz) spectrometer. Chemical shifts (6) are given in parts per million (ppm) relative to $\delta_H$ 7.24/$\delta_C$ 77.0 (central line oft) for CHCl$_3$/CDCl$_3$, $\delta_H$ 4.80 for H$_2$O/D$_2$O, $\delta_H$ 3.31/$\delta_C$ 48.2 for CD$_3$OD, or $\delta_H$ 2.49/$\delta_C$ 39.5 for DMSO-d$_6$. The splitting patterns are reported as s (singlet), d (doublet), t (triplet), q (quartet), m (multiplet), dd (double of doublets) and br (broad). Coupling constants (J) are given in Hz. Distortionless enhancement polarization transfer (DEPT) spectra were taken to determine the types of carbon signals. The ESI-MS experiments were conducted on a Bruker Daltonics BioTOF III high-resolution mass spectrometer. The MALDI-MS measurements were performed on a Bruker Daltonics Ultraflez II MALDI-TOF/TOF 2000 mass spectrometer. The 2,5-dihydroxybenzoic acid (DHB), as MALDI matrix, was photoionized at different irradiances of a UV laser with $\lambda_{max}$ at 337 nm and 355 nm.

All the reagents and solvents were reagent grade and were used without further purification unless otherwise specified. All solvents were anhydrous grade unless indicated otherwise. Lovastatin and simvastatin was obtained from Lotus Pharmaceutical Co. (Nantou, Taiwan). Atorvastatin was obtained from Synpac Kingdom Pharmaceutical Co. (Taipei, Taiwan). SAHA was obtained from Merck (Frankfurter Sparkasse, Germany). The antibody specific for acetyl-histone H3 was obtained from Millipore (Bedford, Mass., USA). Anti-acetyl-tubulin antibody was obtained from Sigma (St. Louis, Mo., USA). Anti-β-actin antibody was purchased from Gene Tex (Irvine, Calif., USA). HDAC Fluorimetric Assay/Drug Discovery Kit (AK-500) was purchased from Biomol (Plymouth Meeting, Pa., USA). HMG-CoA reductase activity kit (CS-1090) and Azoxymethane (AOM) were purchased from Sigma (St. Loius, Mo., USA). Dextran sulfate sodium (DSS) was perchased from MP Biomedicals (Irvine, Calif., USA). $CH_2Cl_2$ was distilled from $CaH_2$. All non-aqueous reactions were carried out in oven-dried glassware under a slight positive pressure of argon unless otherwise noted. Reactions were magnetically stirred and monitored by thin-layer chromatography on silica gel using aqueous p-anisaldehyde as visualizing agent. Silica gel (0.040-0.063 mm particle sizes) and LiChroprep® RP-18 (0.040-0.063 mm particle sizes) were used for column chromatography. Flash chromatography was performed on silica gel of 60-200 μm particle size. Molecular sieves were activated under high vacuum at 220° C. over 6 hours. Purity of test compounds was assessed to be >95% by HPLC (Agilent HP-1100) with detection at 254 or 360 nm wavelength.

To a solution of lovastatin (300 mg, 0.74 mmol) and $MgBr_2$ (273 mg, 1.48 mmol) in anhydrous THF/MeOH (7:3, 3 mL) was added hydroxylamine hydrochloride (438 mg, 6.3 mmol) and sodium bicarbonate (498 mg, 5.9 mmol). The mixture was stirred at ambient temperature for 22 h, and concentrated under reduced pressure. The residue was extracted with EtOAc and saturated NaCl aqueous solution. The organic layer was dried over $MgSO_4$, filtered, concentrated and purified by flash chromatography (silica gel; $CH_2Cl_2$/MeOH (15:1)) to give Lova-HA (256 mg, 79%). The purity was 96% as shown by HPLC on an HC—$C_{18}$ column (Agilent, 4.6×250 mm, 5 μm), $t_R$=14.1 min (gradients of 30-80% aqueous $CH_3CN$ in 30 min). $C_{24}H_{39}NO_6$; colorless oil; $[\alpha]^{24}_D$=+208.1 (EtOAc, c=1.0); TLC ($CH_2Cl_2$/MeOH (9:1)) $R_f$=0.32; IR $\nu_{max}$ (neat) 3323, 3017, 2963, 2932, 2872, 1725, 1659, 1459, 1382, 1264, 1191, 1115, 1081, 1016, 975, 860 $cm^{-1}$; $^1H$ NMR ($CDCl_3$, 400 MHz) δ 5.98 (1H, d, J=9.6 Hz), 5.76-5.80 (1H, m), 5.51 (1H, br s), 5.41 (1H, br s), 4.27 (1H, br s), 3.76 (1H, br s), 2.24-2.43 (6H, m), 1.93 (2H, br s), 1.59-1.68 (5H, m), 1.42-1.47 (2H, m), 1.26 (2H, br s), 1.06-1.11 (6H, m), 0.87 (6H, br s) ppm; $^{13}C$ NMR ($CDCl_3$, 100 MHz) δ 177.4, 169.7, 133.4, 131.8, 129.3, 128.1, 71.5, 68.4, 68.2, 43.0, 41.5, 40.6, 37.3, 36.6, 34.9, 32.7, 30.6, 27.4, 26.8, 24.4, 22.8, 16.2, 13.8, 11.6 ppm; ESI-HRMS (negative mode) calcd. for $C_{24}H_{38}NO_6$: 436.2699. found: m/z 436.2697 $[M–H]^-$.

Example 2

Synthesis of Sim va-HA ((3R,5R)-7-{(1S,2S,6R,8S,8aR)-Hexahydro-2,6-dimethyl-8-[2-dimethylbutyryloxy]naphthalenyl}-3,5-dihydroxy-N-hydroxyheptanamide By a procedure similar to that for Lova-HA, simvastatin (100 mg, 0.24 mmol) was treated with $MgBr_2$ (88 mg, 0.48 mmol), hydroxylamine hydrochloride (438 mg, 6.3 mmol), and sodium bicarbonate (160 mg, 1.9 mmol) in anhydrous THF/MeOH (7:3, 1 mL) at ambient temperature for 22 h to give Simva-HA (52 mg, 48%). The purity was 98% as shown by HPLC on an HC—$C_{18}$ column (Agilent, 4.6×250 mm, 5 μm), $t_R$=20.6 min (gradients of 30-80% aqueous $CH_3CN$ in 30 min). $C_{25}H_{41}NO_6$; colorless oil; $[\alpha]^{24}_D$=+194.1 (EtOAc, c=1.0); TLC ($CH_2Cl_2$/MeOH (9:1)) $R_f$=0.33; IR $\nu_{max}$ (neat) 3309, 3017, 2963, 2928, 2871, 1718, 1659, 1539, 1461, 1261, 1162, 1125, 1058, 975, 860 $cm^{-1}$; $^1H$ NMR ($CDCl_3$, 400 MHz) δ 5.98 (1H, d, J=9.6 Hz), 5.76-5.79 (1H, m), 5.49 (1H, br s), 5.44 (1H, br s), 4.22 (1H, br s), 3.77 (1H, br s), 2.22-2.44 (6H, m), 1.99 (1H, dd, J=13.2, 8.0 Hz), 1.85-1.89 (1H, m), 1.50-1.58 (7H, m), 1.26 (2H, br s), 1.09-1.12 (9H, m), 0.80-0.87 (6H, m) ppm; $^{13}C$ NMR ($CDCl_3$, 100 MHz) δ 178.5, 169.7, 133.2, 131.7, 129.3, 128.2, 71.4, 68.4, 68.3, 43.0, 40.6, 37.5, 36.6, 34.9, 33.0, 32.8, 30.6, 29.6, 27.2, 24.7, 24.6, 24.4, 23.0, 13.8, 9.2 ppm; ESI-HRMS (negative mode) calcd. for $C_{25}H_{40}NO_6$: 450.2856. found: m/z 450.2854 $[M–H]^-$.

Example 3

Synthesis of Atorva-HA ((3R,5R)-7-[2-(4-Fluorophenyl)-5-isopropyl-3-phenyl-4-phenylcarbamoyl pyrrol-1-yl]-3,5-dihydroxy-N-hydroxyheptanamide)

By a procedure similar to Lova-HA, atorvastatin (168 mg, 0.31 mmol, in the lactone form) was treated with $MgBr_2$ (115 mg, 0.62 mmol), hydroxylamine hydrochloride (184 mg, 2.6 mmol), and sodium bicarbonate (209 mg, 2.5 mmol) in anhydrous THF/MeOH (7:3, 1 mL) at ambient temperature for 20 h to give Atorva-HA (91 mg, 51%). The purity was 95% as shown by HPLC analysis on an HC—$C_{18}$ column (Agilent, 4.6×250 mm, 5 Gm), $t_R$=14.8 min (gradients of 30-100% aqueous $CH_3CN$ in 30 min). $C_{33}H_{36}FN_3O_5$; colorless oil; $[\alpha]^{26}_D$=−1.3 (EtOAc, c=1.0); TLC ($CH_2Cl_2$/MeOH (9:1)) $R_f$=0.33; IR $\nu_{max}$ (neat) 3405, 3301, 3059, 2960, 2926, 1738, 1657, 1595, 1527, 1508, 1436, 1314, 1241, 1223, 1157, 1108, 1078, 1046, 843, 753, 692 $cm^{-1}$; $^1H$ NMR (DMSO-$d_6$, 400 MHz) δ 10.31 (1H, br s), 9.77 (1H, br s), 8.68 (1H, br s), 7.50 (2H, d, J=7.6 Hz), 7.18-7.24 (6H, m), 7.07 (4H, br s), 6.98-7.00 (2H, m), 4.69 (1H, br s), 4.60 (1H, d, J=4.0 Hz), 3.92-3.95 (1H, m), 3.72-3.83 (2H, m), 3.53 (1H, br s), 3.21-3.25 (1H, m), 2.01 (2H, d, J=6.0 Hz), 1.63 (1H, br s), 1.53 (1H, br s), 1.28-1.38 (8H, m) ppm; $^{13}C$ NMR (DMSO-$d_6$, 100 MHz) δ 167.4, 166.1, 162.8, 160.3, 139.4, 135.9, 134.9, 133.4, 129.1 (2×), 128.7, 128.4 (2×), 127.6 (2×), 127.3, 125.3, 122.9, 120.6, 119.4 (2×), 117.5, 115.4, 115.2, 66.0, 65.6, 43.8, 40.9, 40.7, 25.6, 22.3 (2×) ppm; ESI-HRMS (negative mode) calcd. for $C_{33}H_{35}FN_3O_5$: 572.2561. found: m/z 572.2562 $[M–H]^-$.

Example 4

Synthesis of Rosuva-HA ((3R,5S,6E)-7-[4-(4-fluorophenyl)-2-(N-methylmethanesulfonamido)-6-isopropyl pyrimidin-5-yl]-3,5-dihydroxy-N-hydroxy-6-heptanamide)

By a procedure similar to Lova-HA, rosuvastatin (68 mg, 0.15 mmol, in the lactone form) was treated with $MgBr_2$ (54 mg, 0.29 mmol), hydroxylamine hydrochloride (87 mg, 1.25 mmol), and sodium bicarbonate (99 mg, 1.18 mmol) in anhydrous THF/MeOH (7:3, 647 L) at ambient temperature for 6 h to give Rosuva-HA (37 mg, 51%). The purity was 97% as shown by HPLC analysis on an HC—$C_{18}$ column (Agilent, 4.6×250 mm, 5 am), $t_R$=13.8 min (gradients of 25-80% aqueous $CH_3CN$ in 30 min). $C_{22}H_{29}FN_4O_6S$; colorless oil;

$[\alpha]^{24}{}_D$=−1.1 (EtOAc, c=1.0); TLC (CH$_2$Cl$_2$/MeOH (9:1)) R$_f$=0.35; IR $\nu_{max}$ (neat) 3326, 2925, 2853, 1737, 1660, 1604, 1546, 1510, 1437, 1381, 1336, 1230, 1153, 1069, 965, 901, 845, 776 cm$^{-1}$; $^1$H NMR (DMSO-d$_6$, 400 MHz) δ 10.32 (1H, br s), 8.70 (1H, br s), 7.71-7.74 (2H, m), 7.30 (2H, t, J=8.8 Hz), 6.50 (1H, dd, J=1.2, 16.2 Hz), 5.54 (1H, dd, J=5.6, 16.2 Hz), 4.94 (1H, d, J=4.4 Hz), 4.70 (1H, d, J=4.8 Hz), 4.19-4.22 (1H, m), 3.88 (1H, br s), 3.55 (3H, s), 3.41-3.48 (4H, m), 2.05 (2H, d, J=6.4 Hz), 1.48-1.56 (1H, m), 1.37-1.43 (1H, m), 1.22 (6H, d, J=6.8 Hz) ppm; $^{13}$C NMR (DMSO-d$_6$, 100 MHz) δ 174.8, 167.9, 164.3, 163.3, 161.8, 157.3, 141.7, 134.9, 134.8, 132.6, 132.5, 122.2, 121.9, 115.6, 115.4, 69.1, 65.6, 44.6, 42.0, 41.2, 33.7, 31.7, 22.0 (2×) ppm; ESI-HRMS (negative mode) calcd. for C$_{33}$H$_{35}$FN$_3$O$_5$: 572.2561. found: m/z 572.2562 [M−H]$^-$.

Example 5

Synthesis of Fluva-HA ((3R,5S,6E)-7-[3-(4-Fluorophenyl)-1-isopropyl-1H-indol-2-yl]-3,5-dihydroxy-N-hydroxy-6-heptenamide)

To a solution of fluvastatin (100 mg, 0.25 mmol, in the lactone form) in THF (1 mL) was added 50% hydroxylamine in H$_2$O (0.12 mL, 1.91 mmol). The mixture was stirred at ambient temperature for 16 h, and concentrated under reduced pressure. The residue was extracted with CH$_2$Cl$_2$. The organic layer was washed with brine, dried over MgSO$_4$, filtered, concentrated, and purified by flash chromatography (silica gel; CH$_2$Cl$_2$/MeOH/NEt$_3$ (89:1:9 to 5:5:1)) to give fluva-HA (30 mg, 30%). C$_{24}$H$_{27}$FN$_2$O$_4$; white foam; TLC (CH$_2$Cl$_2$/MeOH (9:1)) R$_f$=0.13; $^1$H NMR (CDCl$_3$, 400 MHz) δ 7.57-7.59 (1H, d, J=8.4 Hz), 7.41-7.44 (3H, m), 7.13-7.19 (3H, m), 6.99-7.03 (1H, t), 6.69-6.73 (1H, d, J=14.8 Hz), 5.74-5.79 (1H, dd, J=16.4 Hz), 4.95 (1H, br s), 4.39-4.42 (1H, m), 4.21-4.24 (1H, m), 2.24-2.25 (2H, m), 1.64-1.73 (6H, m), 1.32-1.36 (2H, m) ppm; ESI-HRMS calcd for C$_{24}$H$_{28}$FN$_2$O$_4$: 427.2033. found: m/z 427.2034 [M+H]$^+$.

Example 6

Synthesis of 3-PMB-Lova-HA ((3R,5R)-7-{(1S,2S,6R,8S,8aR)-Hexahydro-2,6-dimethyl-8-[2-methylbutyryloxy]naphthalenyl}-5-hydroxy-3-(p-methoxybenzyloxy)-N-hydroxyheptanamide)

By a procedure similar to that for Lova-HA, 3-O-(p-methoxybenzyl)lovastatin (130 mg, 0.25 mmol) was treated with MgBr$_2$ (91 mg, 0.49 mmol), hydroxylamine hydrochloride (146 mg, 2.1 mmol), and sodium bicarbonate (166 mg, 2.0 mmol) in anhydrous THF/MeOH (7:3, 1.1 mL) at ambient temperature for 76.5 h to give the title compound (39 mg, 28%). The purity was 97.3% as shown by HPLC on an HC—C$_{18}$ column (Agilent, 4.6×250 mm, 5 μm), t$_R$=14.4 min (gradients of 50-100% aqueous CH$_3$CN in 30 min). C$_{32}$H$_{47}$NO$_7$; colorless oil; $[\alpha]^{24}{}_D$=+222.9 (EtOAc, c=1.0); TLC (EtOAc/hexane (5:5)) R$_f$=0.06; IR $\nu_{max}$ (neat) 3269, 2962, 2934, 2873, 1730, 1660, 1613, 1516, 1461, 1377, 1302, 1251, 1184, 1081, 1034, 861, 822, 756 cm$^{-1}$; $^1$H NMR (CDCl$_3$, 400 MHz) δ 7.24 (2H, d, J=8.0 Hz), 6.88 (2H, d, J=8.0 Hz), 5.98 (1H, d, J=9.6 Hz), 5.76-5.80 (1H, m), 5.51 (1H, br s), 5.45 (1H, br s), 4.50 (2H, dd, J=10.8, 30.0 Hz), 4.04 (1H, br s), 3.80 (3H, s), 3.69 (1H, br s), 2.58 (1H, br s), 2.22-2.44 (6H, m), 1.91 (2H, br s), 1.61-1.68 (5H, m), 1.39-1.46 (2H, m), 1.06-1.11 (8H, m), 0.85-0.89 (6H, m) ppm; $^{13}$C NMR (CDCl$_3$, 100 MHz) δ 177.8, 168.4, 159.5, 133.3, 131.6, 129.6 (2×), 129.4, 129.3, 128.2, 114.1 (2×), 75.7, 71.1, 70.6, 68.3, 55.3, 41.7, 40.4, 38.2, 37.3, 36.5, 34.8, 32.9, 30.6, 27.4, 26.8, 24.3, 22.9, 16.2, 13.8, 11.7 ppm; ESI-HRMS (positive mode) calcd. for C$_{32}$H$_{47}$NO$_7$: 558.3431. found: m/z 558.3436 [M+H]$^+$.

Example 7

Synthesis of 3-PMB-Atorva-HA ((3R,5R)-7-[2-(4-Fluorophenyl)-5-isopropyl-3-phenyl-4-phenylcarbamoyl-pyrrol-1-yl]-5-hydroxy-3-(p-methoxybenzyloxy)-N-hydroxyheptanamide)

By a procedure similar to to that for Lova-HA, 3-O-(p-methoxybenzyl)atorvastatin was treated with MgBr$_2$ (88 mg, 0.48 mmol), hydroxylamine hydrochloride (139 mg, 2.0 mmol), and sodium bicarbonate (162 mg, 1.9 mmol) in anhydrous THF/MeOH (7:3, 0.7 mL) at ambient temperature for 31 h to give the title compound (82 mg, 74%). The purity was 95% as shown by HPLC on an HC—C$_{18}$ column (Agilent, 4.6×250 mm, 5 μm), t$_R$=15.2 min (gradients of 40-100% aqueous CH$_3$CN in 30 min). C$_{41}$H$_{44}$FN$_3$O$_6$; colorless oil; $[\alpha]^{25}{}_D$=+11.6 (EtOAc, c=1.0); TLC (EtOAc/hexane (5:5)) R$_f$=0.08; IR $\nu_{max}$ (neat) 3402, 3250, 2957, 2930, 2872, 1735, 1654, 1596, 1512, 1437, 1313, 1247, 1157, 1078, 1043, 848, 820, 754, 698 cm$^{-1}$; $^1$H NMR (CDCl$_3$, 400 MHz) δ 7.16-7.19 (11H, m), 10.06 (2H, d, J=7.6 Hz), 7.00-6.95 (3H, m), 6.92 (1H, s), 6.84 (2H, d, J=7.2 Hz), 4.37 (2H, dd, J=10.0, 44.4 Hz), 4.06 (1H, br s), 3.91 (2H, br s), 3.76 (3H, s), 3.51-3.56 (2H, m), 2.33 (2H, br s), 1.59 (3H, br s), 1.50-1.51 (7H, m) ppm; $^{13}$C NMR (CDCl$_3$, 100 MHz) δ 168.4, 165.4, 163.5, 161.0, 159.6, 141.2, 138.2, 134.5, 133.2, 133.1, 130.4 (2×), 129.7 (2×), 129.1, 128.8, 128.7 (2×), 128.4 (2×), 126.5, 123.8, 121.9, 119.8 (2×), 115.6, 115.4, 114.1 (2×), 75.1, 71.4, 67.6, 55.3, 41.2, 40.8, 38.9, 37.9, 26.2, 22.0, 21.8 ppm; ESI-HRMS (positive mode) calcd. for C$_{41}$H$_{44}$FN$_3$O$_6$: 694.3292. found: m/z 694.3286 [M+H]$^+$.

Example 8

Molecular Modeling

The crystal structures of HMGR complex (PDB code: 1HW9) was adopted from Protein Data Bank. The structures of HDACs were prepared by homology modeling. The sequence alignment between human HDACs and histone deacetylase-like (HDLP) was determined by the multiple sequence alignment between human class I HDACs (HDAC1, HDAC2, HDAC3, HDAC8) and HDLP using the ClustalW module with the BLOSUM scoring matrix in Discovery Studio 2.55 (Accelrys, Inc., San Diego, Calif.). The homology model structures were generated and optimized by MODELLER in Discovery Studio 2.55 (Accelrys, Inc.) The structural template of the homology modeling of HDACs, the HDLP structure, was obtained from the Protein Datank (PDB ID: 3CSR). The structure with the lowest energy score was selected as the final model. All non-protein molecules were deleted except that zinc ion was retained in the HDAC2 complex. The receptor was prepared by using the AutoDock 4 suite (Morris, G. M. et al., *J. Comput. Chem.*, 2009, 30, 2785-2791). The grid box sizes were adjusted to cover the original ligand and its surrounding binding pocket residues with 48×40×40 grid points in HDAC and 40×40×52 grid points in HMG-CoA reductase with a grid spacing of 0.375 Å, respectively. The binding pose with lowest score in each case was selected to represent predicted binding mode. The 2D protein-ligand interaction plots were presented using Molecular Operating Environment.

Example 9

Lova-HA, Simva-HA and Atorva-HA Inhibited HDAC and HMGR Activity and Cancer Cell Growth Materials and Methods (i) Cell Culture A549 human lung carcinoma cells from American Type Culture Collection (ATCC) were cultured in Dulbecco's Modified Eagle Medium (DMEM). Mouse embryonic fibroblast (MEF) and human foreskin fibroblast HS68 cells were cultured in RPMI 1640. All mediums were supplemented with 10% fetal bovine serum (FBS), 100 U/mL penicillin G and 100 mg/mL streptomycin sulfate. Cells were maintained in a humidified incubator containing 5% $CO_2$ in air. Cells were subcultured by trypsinization in laminar flow when grew about 80% in the culture dishes.

(ii) HDAC Activity Assay

The HDAC activity was performed using the HDAC fluorescent activity assay kit (BIOMOL, Plymouth Meeting, Pa., USA) according to the manufacturer's instructions. Briefly, recombinant proteins of HDAC1 or HDAC6 were incubated with test compounds, and HDAC reaction was initiated by addition of Fluor-de-Lys substrate. Samples were incubated for 10 min at room temperature, followed by adding developer to stop the reaction. Fluorescence was measured by fluorometric reader with excitation at 360 nm and emission at 460 nm. The HDAC activity was expressed as arbitrary fluorescence units (AFU). The HDAC activity was calculated as a percentage of activity compared with the control group. The half maximal inhibitory concentration ($IC_{50}$) values for the test compounds were calculated from software SigmaPlot.

(iii) HMG-CoA Reductase Activity Assay

The HMGR activity was performed using HMG-CoA reductase assay kit from Sigma-Aldrich with the human recombinant protein or 100 µg total cell lysates from A549 cells. Lovastatin was used as a positive control, and SAHA as a negative control. HMGR activity under defined assay conditions, containing NADPH and HMG-CoA substrate in a final volume of 0.2 mL of 100 mM potassium phosphatate buffer (120 mM KCl, 1 mM EDTA, 5 mM DTT, pH 7.4), were initiated in the presence or absence (control) of test compounds dissolved in dimethylsulfoxide (DMSO). The rates of NADPH consumption were monitored every 20 seconds, for up to 10 minutes, by spectrophotometer at 37° C. and 340 nm. The HMGR activity was calculated as a percentage of activity compared with the control group at 5 min. The $IC_{50}$ values were calculated from software SigmaPlot.

(iv) Western Blot Analysis

Following treatment with test compounds, cells were lysed on ice. Total cell lysates were centrifuged at 13,000 rpm for 15 min at 4° C., and then subjected to SDS-PAGE using adequate percentage polyacrylamide gels. Immunoblotting was performed using specific antibodies to evaluate the expression of different proteins.

(v) Cell Proliferation Assay

A549 cells were seeded at 3000 cells/well in 96-well plates and maintained for 14-16 hours. Cells were treated with dimethylsulfoxide DMSO or test compounds in varied concentrations for 72 h. Cells were then washed with PBS twice, added a medium containing 3-(4,5-dimethylthiazol-2-yl)-2, 5-diphenyltetrazolium bromide (MTT) at a final concentration of 0.5 mg/mL, and incubated for 4 h at 37° C. in a humidified incubator containing 5% $CO_2$ in air. Cells having functional succinate dehydrogenase of mitochondria would convert MTT to formazan. Then, the medium was replaced with 100 µL of DMSO for 30 min at room temperature, and the 96-well plate was read by an ELISA reader at 550 nm to get the absorbance density values. The $IC_{50}$ values of death cell lines were calculated accordingly.

(vi) Animal Model of AOM/DSS-Induced Colon Cancer

Male C57BL6 mice obtained at 4-5 weeks of age were divided into four groups. Group 1 (vehicle control group) mice were only received oil, group 2 (lovastatin group) mice were orally treated with lovastatin (50 mg/kg/day), group 3 (low-dose group) mice were orally treated with Lova-HA (25 mg/kg/day), and group 4 (high-dose group) mice were orally treated with Lova-HA (50 mg/kg/day) in oil on days 1-5 for eight weeks. All mice were intraperitoneally (i.p.) injected with a single dose of 12.5 mg/kg azoxymethane (AOM) on the first week and received 3.5% dextran sulfate sodium (DSS) in drinking water for 5 days at weeks 2, 5, and 8. All mice were sacrificed after 9 weeks and colon segments were fixed in formalin. H&E stain colonic sections were examined for colonic aberrant crypts. All animal work was performed under protocols approved by the Institutional Animal Care and Use Committee of the College of Medicine, National Taiwan University.

Results (i) HDACs and HMGR Inhibition

The activities of Lova-HA (compound 1), Simva-HA (compound 2), Atorva-HA (compound 5), Rosuva-HA (compound 7), on HDAC (e.g., HDAC1, HDAC2, and HDAC6) and HMGR inhibition were evaluated by both enzyme-based and cell-based assays. HDAC fluorometric activity assay was performed using Fluor-de-Lys as the substrate (BIOMOL, Plymouth Meeting, Pa., USA), and HMGR inhibition was evaluated by the NADH-coupled assay. Table 1 shows that Lova-HA, Simva-HA, Atorva-HA, and Rosuva-HA exhibited potent HMGR inhibition with $IC_{50}$ values in nanomolar range similar to statins. However, SAHA showed no significant inhibition of HMGR. Lova-HA, Simva-HA, Atorva-HA, and Rosuva-HA also showed good inhibitory activities against HDAC1 and HDAC6 with $IC_{50}$ values in a range of 30-160 nM. In sharp contrast, statins inhibit HDACs at a concentration of more than 10 µM. Moreover, Lova-HA, Simva-HA, Atorva-HA, and Rosuva-HA showed inhibitory activities against HDAC2 with $IC_{50}$ values in the range of about 400-630 nM, comparable to the activity of SAHA in inhibiting HDAC2 ($IC_{50}$ value about 100 nM). On the contrary, lovastatin and atorvastatin showed almost no activity against HDAC2 at nanomolar concentrations ($IC_{50}$ values above 20 µM).

TABLE 1

Inhibitory activities against HMG-CoA reductase (HMGR), HDAC1, HDAC2, and HDAC6

| Compound | IC$_{50}$ (nM) | | | |
|---|---|---|---|---|
| | HMGR | HDAC1 | HDAC2 | HDAC6 |
| SAHA | >10000 | 20.9 ± 7.1 | 100.9 ± 10.0 | 19.4 ± 6.0 |
| Lovastatin[a] | 29.5 ± 3.5 | 11214 ± 1596 | 25933 ± 651 | 16283 ± 3093 |
| Atorvastatin[a] | 11.6 | 11148 | 22547 ± 1618 | 14151 |
| Lova-HA (1) | 16.8 ± 1.9 | 60.1 ± 5.3 | 468.3 ± 27.2 | 50.5 ± 4.0 |
| Simva-HA (2) | 11.4 | 60.7 ± 3.2 | 414.2 ± 15.5 | 67.1 |
| Atorva-HA (5) | 9.2 | 117.5 | 467.2 ± 19.0 | 83.7 |
| Rosuva-HA (7) | 43.7 ± 1.6 | 125.2 ± 7.1 | 600.1 ± 34.0 | 133.3 ± 5.5 |

[a]Lovastatin and atorvastatin in the carboxylic acid form were used.

Figures 1C, 1D:
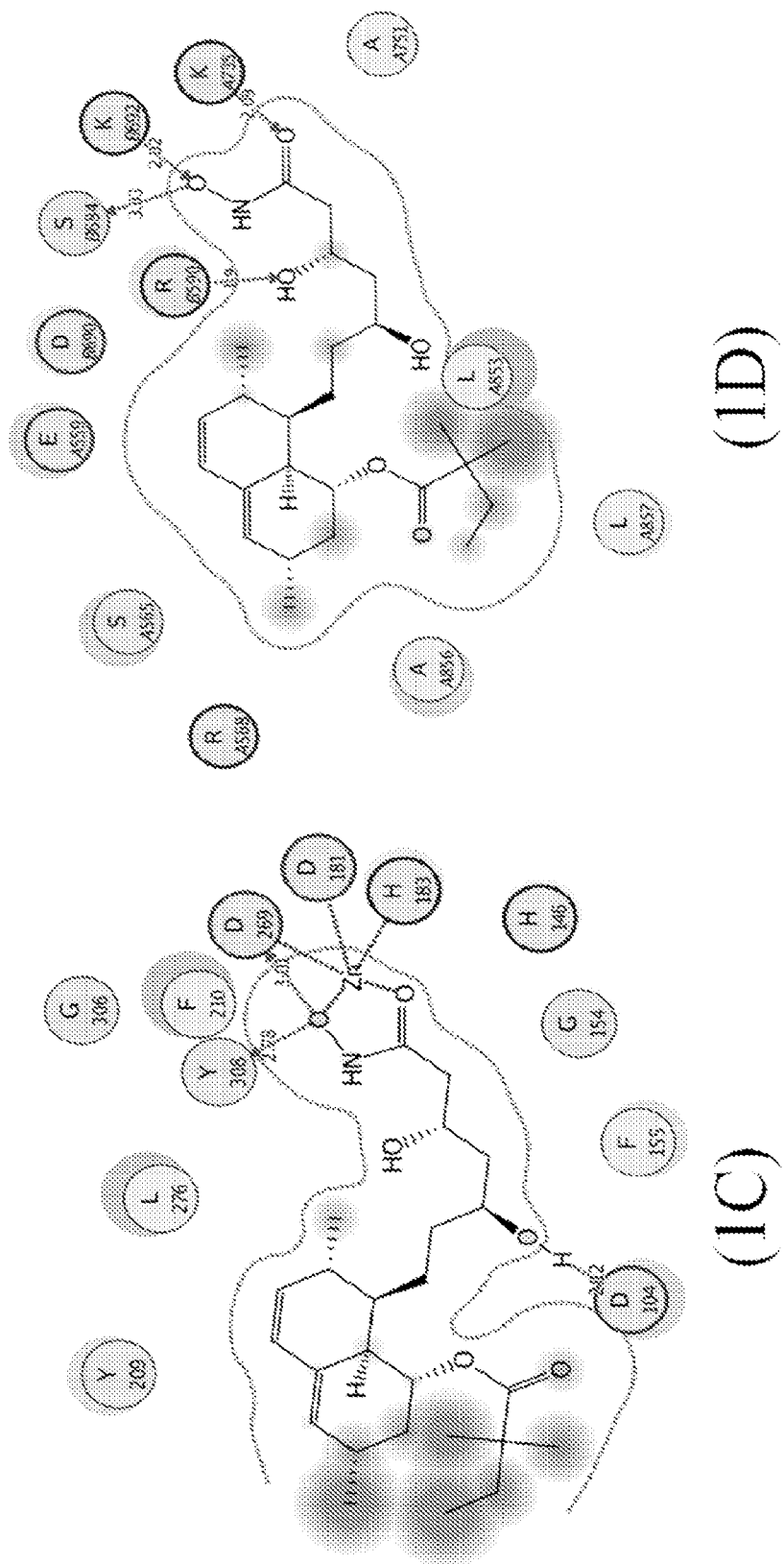
Figures 1E, 1F:
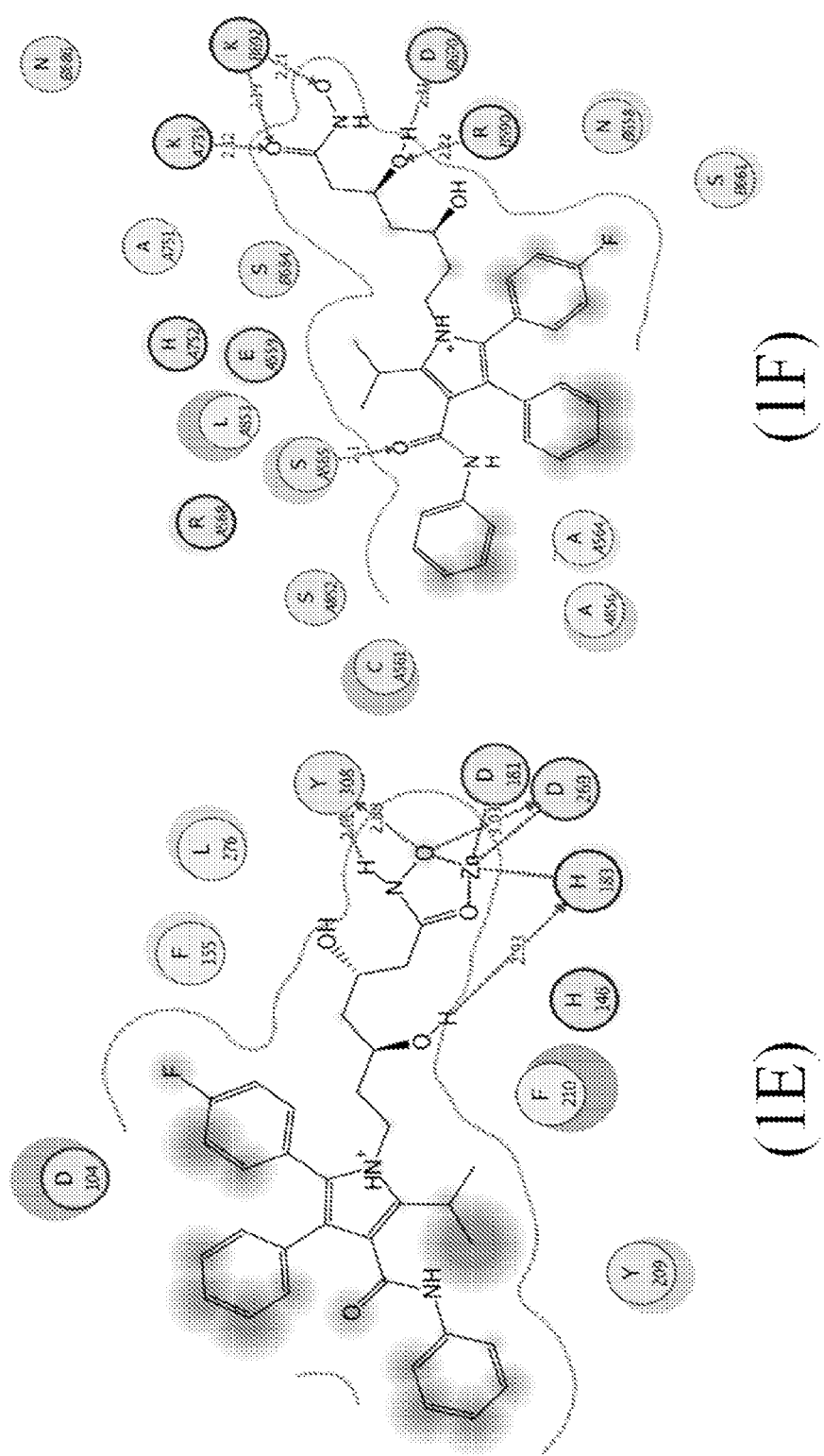

(ii) Molecular Modeling for the Binding Modes of Lova-HA, Simva-HA and Atorva-HA with HDAC The docking analysis illustrates the binding modes of Lova-HA with HDAC2 and HMG-CoA reductase, respectively. The detailed protein-inhibitor interactions of HDAC and HMGR with the designed bifunctional compounds Lova-HA, Simva-HA and Atorva-HA are shown in FIG. 1. The binding modes of these three compounds with HDAC2 consistently show that the moiety of 3,5,N-trihydroxy-heptanamide inserts into the catalytic outer-tunnel of HDAC. Hydroxamic acid is considered a bioisostere of the carboxylic acid. The hydroxamate group also chelates a zinc ion, which is important for the catalytic process. In addition, the 3,5-dihydroxyl groups also contribute to the hydrogen-bonding interactions with the residues in the catalytic tunnel. In contrast to the previously developed HDAC inhibitors that simply exert hydrophobic interactions with the catalytic tunnel of HDAC, the results of molecular modeling also reveal the importance of placing polar substituents, e.g. OH group, at proper locations to enhance the binding affinity of HDAC inhibitors. This finding leads to designing potent HDAC inhibitors that bear 3,5-dihydroxyl substituents on the alkyl chain. Molecular models indicate that the hydroxamate moiety in Lova-HA, Simva-HA and Atorva-HA provides hydrogen bondings to at least two residues of Lys A735, Ser B684, and Lys B692, similar to that in the crystal structures of statin-HMGR complexes. (Istvan, E. S. & Deisenhofer, J. Science 2001, 292, 1160.) Through this study, it is demonstrated that replacement of the carboxylic acid in statins with N-hydroxyamide indeed provide enhanced inhibition against HDACs and somewhat improved binding with HMGR.

Figure 2:
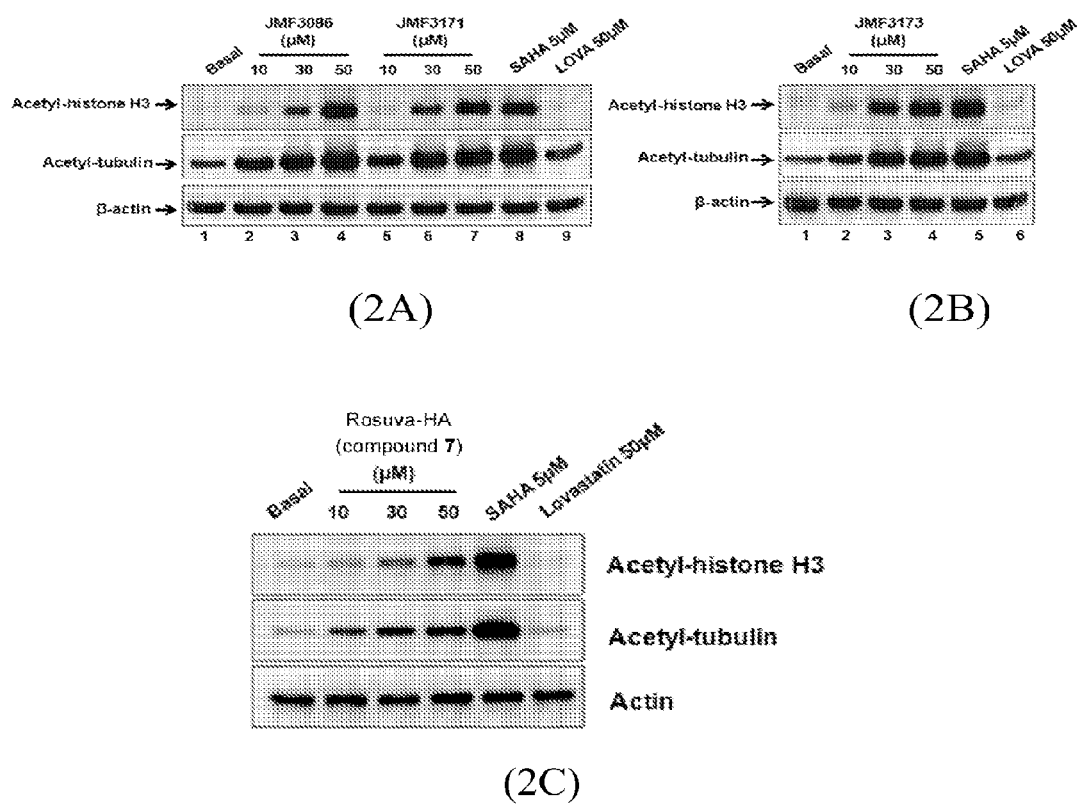
FIG. 2 is a photo showing the effect of test compounds on acetylation of histone H3 and tubulin in A549 lung cancer cell lines. JMF3086 is Lova-HA, JMF3171 is Simva-HA, and JMF3173 is Atorva-HA. A549 cells were treated with the indicated doses of test compounds. Total cell lysates were prepared and subjected to SDS-PAGE using adequate percentage of polyacrylamide gels. Immunoblotting was performed using specific antibodies to evaluate the expression of different proteins.

To further examine whether the synthetic compounds Lova-HA, Simva-HA, Atorva-HA, and Rosuva-HA could increase acetylation of histone and tubulin, the levels of acetyl-histone H3 (for inhibition of HDACs 1 and 2) and acetyl-tubulin (for inhibition of HDAC6) were analyzed by Western blot analysis (FIG. 2). A549 lung cancer cells were treated with the test compound, and the expression of acetyl-histone H3 and acetyl-tubulin were analyzed by SDS-PAGE using immunoblotting. These experiments confirmed that Lova-HA, Simva-HA, Atorva-HA, and Rosuva-HA inhibited HDACs in a dose-dependent manner and that these compounds promoted the acetylations of histone and tubulin in cancer cells in a dose-dependent manner.

(iii) Cell-Based Assay of HMGR Inhibition

Figure 3:
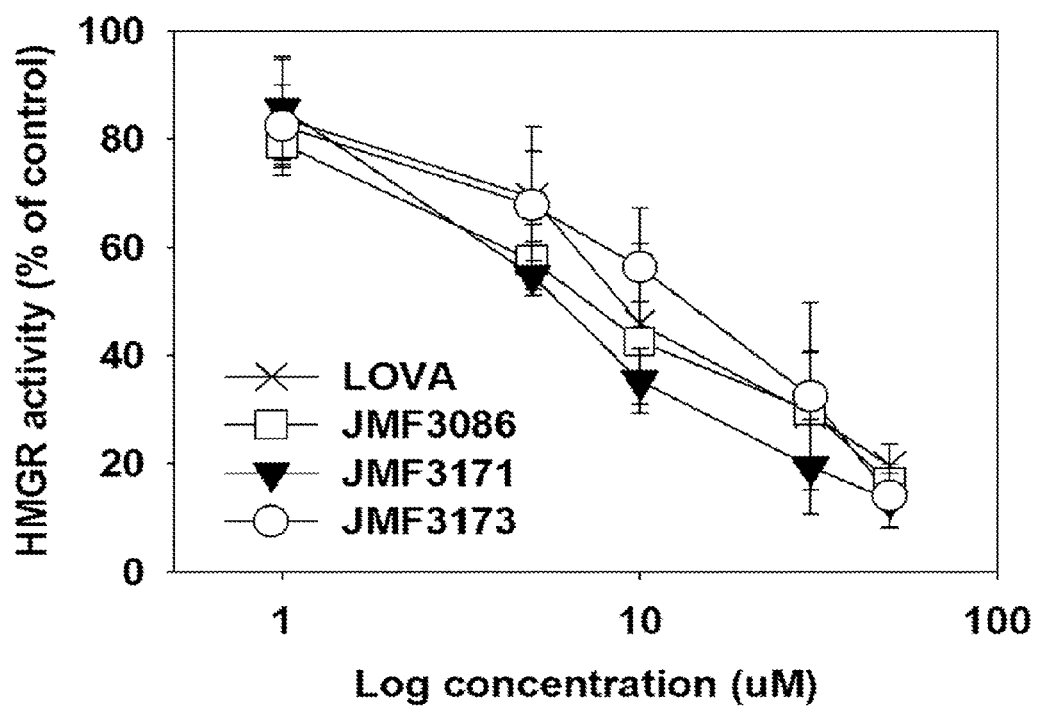
FIG. 3 is a chart showing the effect of 3,5,N-trihydroxy-alkanamides on activity of HMG-CoA reductase in A549 lung cancer cell lines. JMF3086 is Lova-HA, JMF3171 is Simva-HA, and JMF3173 is Atorva-HA. A549 cells were treated with indicated doses of test compounds for 24 hours. Total protein lysates were then subjected to HMG-CoA reductase activity assay.

For the cell-based assay of HMGR inhibition (FIG. 3), A549 lung cancer cells were incubated with varied doses of Lova-HA, Simva-HA and Atorva-HA. The cell lysates were subjected to HMG-CoA reductase activity assay. The results indicated that Lova-HA, Simva-HA and Atorva-HA showed equal or even better activity than lovastatin in HMGR inhibition. Thus, Lova-HA, Simva-HA and Atorva-HA were proved to be dual-functional inhibitors against both HMGR and HDACs.

Figure 4:
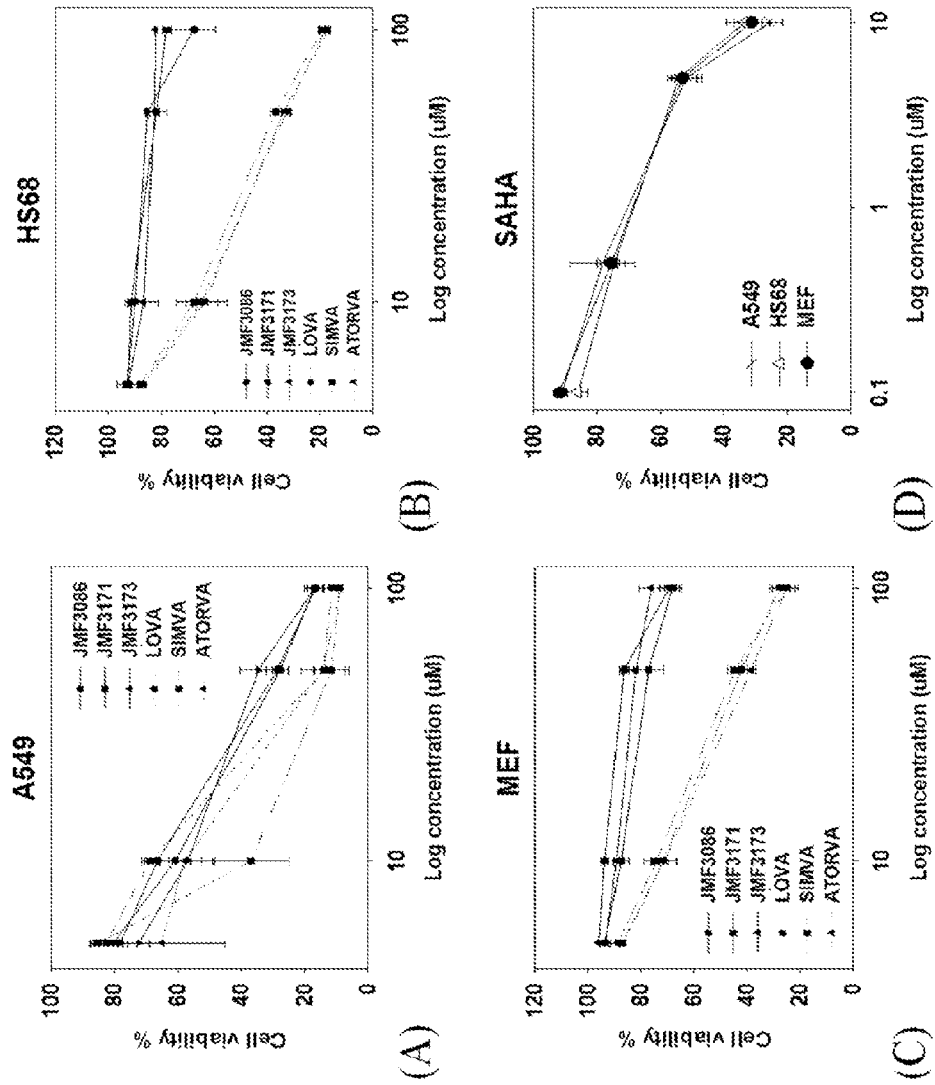
FIG. 4 is a diagram showing the effect of test compounds on cell viability. JMF3086 is Lova-HA, JMF3171 is Simva-HA, and JMF3173 is Atorva-HA. (4A) human lung cancer A549 cells, (4B) human foreskin fibroblast HS68 cells, (4C) mouse embryonic fibroblast (MEF) cells, and (4D) A549, HS68 and MEF cells were treated with SAHA for 72 h. The cell viability was measured by MTT assay.

(iv) Lova-HA, Simnva-HA and Atorva-HA Inhibit Cell Growth of A549 Lung Cancer Cells without Affecting Normal Fibroblast Cells To determine the cytotoxicity and specificity of Lova-HA, Simva-HA and Atorva-HA, A549 human lung cancer cells, MEF normal mouse fibroblast cells, and HS68 normal human fibroblast cells were treated with different doses of test compounds. As shown in FIG. 4A, cell viability of A549 was reduced by Lova-HA, Simva-HA, Atorva-HA and statins. In contrast to statins which showed obvious killing effects on HS68 (FIG. 4B) and MEF normal cells (FIG. 4C), Lova-HA, Simva-HA and Atorva-HA did not have cytotoxicity. The HDAC inhibitor SAHA killed cancer cells and was also toxic to normal cells (FIG. 4D). The cytotoxicity and specificity of the test compounds are also shown in Table 2. SAHA was toxic to both cancer and normal cells without specificity. The selectivity index of statins for cancer and normal cells was low. Lova-HA, Simva-HA, and Atorva-HA significantly induced cytotoxicity in the cancer cells (IC$_{05}$<20 μM), but were not toxic to the normal cells at 100 μM. These results indicated that Lova-HA, Simva-HA and Atorva-HA specifically inhibited the growth of cancer cells without toxic effect on normal cells.

TABLE 2

Inhibition on the growth of cancer and normal cells

| Test compound | IC$_{50}$[a] (μM) | | | SI[b] | |
|---|---|---|---|---|---|
| | A549 | MEF | HS68 | A549/ MEF | A549/ HS68 |
| lovastatin | 11.4 ± 6.3 | 35.0 ± 5.9 | 23.2 ± 3.5 | 3.1 | 2.0 |
| simvastatin | 16.3 ± 0.1 | 36.7 ± 4.4 | 26.4 ± 2.1 | 2.3 | 1.6 |
| atorvastatin | 8.7 ± 1.1 | 30.7 ± 3.2 | 22.7 ± 2.0 | 3.5 | 2.6 |
| SAHA | 4.5 ± 0.8 | 4.4 ± 1.4 | 4.6 ± 0.7 | 1.0 | 1.0 |
| Lova-HA (1) | 18.2 ± 3.4 | >100 | >100 | >5.6 | >5.6 |
| Simva-HA (2) | 20.0 ± 3.1 | >100 | >100 | >5.0 | >5.0 |
| Atorva-HA (5) | 17.5 ± 4.7 | >100 | >100 | >5.7 | >5.7 |

[a]Cells were treated with the indicated doses of test compounds for 72 h, and the cell viability was measured by MTT assay. Data are shown as the mean ± SD of three experiments. "A549" represents human lung cancer cells, "MEF" represents normal mouse fibroblast cells, and "HS68" represents normal human fibroblast cells.
[b]The selectivity index ("SI") is the ratio of the IC$_{50}$ value of a compound on a cancer cell to the IC$_{50}$ value of the compound on a normal cell.

(v) Lova-HA Prevents Colon Carcinogenesis in AOM/DSS Mice

Figures 5A, 5B:
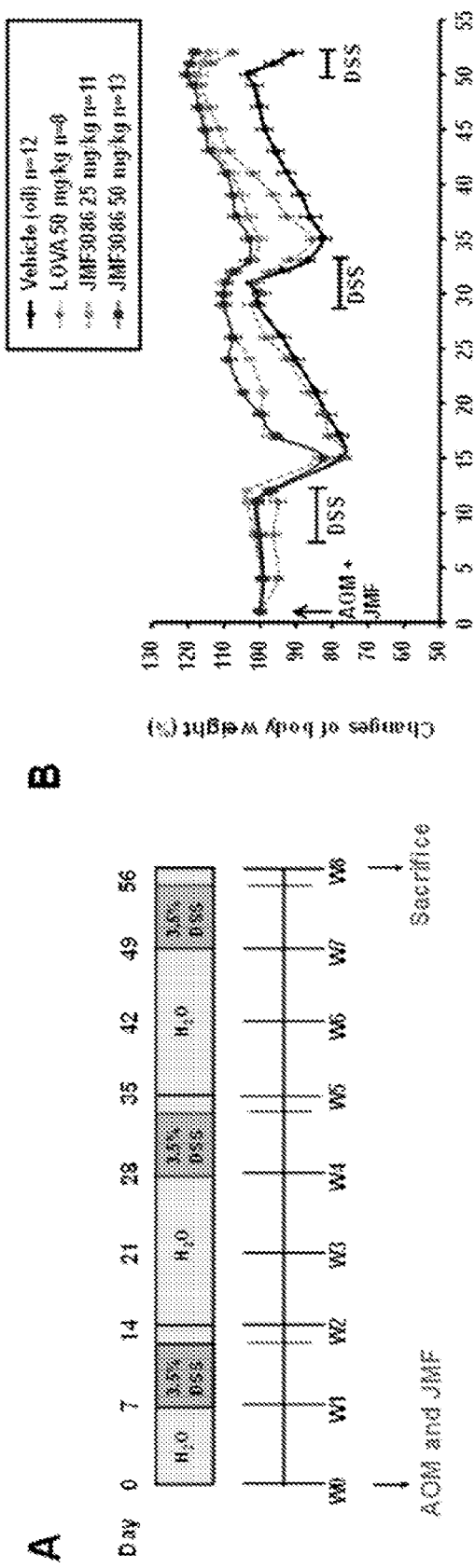
FIG. 5 is a diagram showing the chemopreventive effect of Lova-HA on a mouse model of colitis-associated colorectal cancer. Mice were intraperitoneally injected with AOM (12.5 mg/kg body weight) and maintained for 7 days, then subjected to 3 cycles of DSS treatment (1 cycle representing 5 days of 3.5% DSS followed by 14 days of $H_2O$). Lova-HA and lovastatin were dissolved in corn oil. Lova-HA (25 mg/kg and 50 mg/kg), lovastatin (50 mg/kg) or the vehicle (corn oil) was orally administered at the same time of AOM exposure 5 days a week for 8 weeks. All mice were sacrificed at 9 weeks and colon segments were fixed by formalin. (5A) Schematic overview of test compounds administration. (5B) Changes in body weights. (5C) Clinical bleeding scores. (5D) Clinical diarrhea scores. (5E) Colon length. Significant difference between control and vehicle treatment is indicated as ##$P<0.01$, and that between vehicle and drug treatment is indicated as *$P<0.05$ and **$P<0.01$. (5F) Representative whole colons. (5G) Representative whole colons. (5H) Representative terminal colons and number of tumors per mouse and total tumor size (represented as sum of diameters of all tumors). (5I) Representative H&E stain of terminal colons.
Figures 5C, 5D:
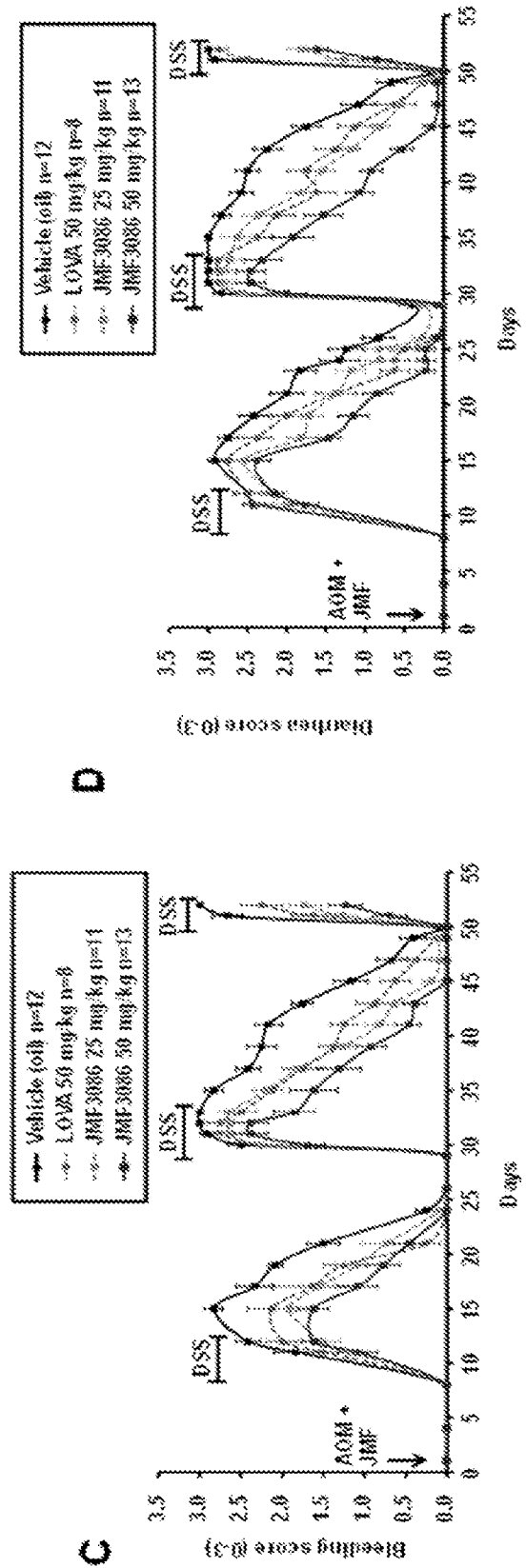
Figures 5E, 5F:
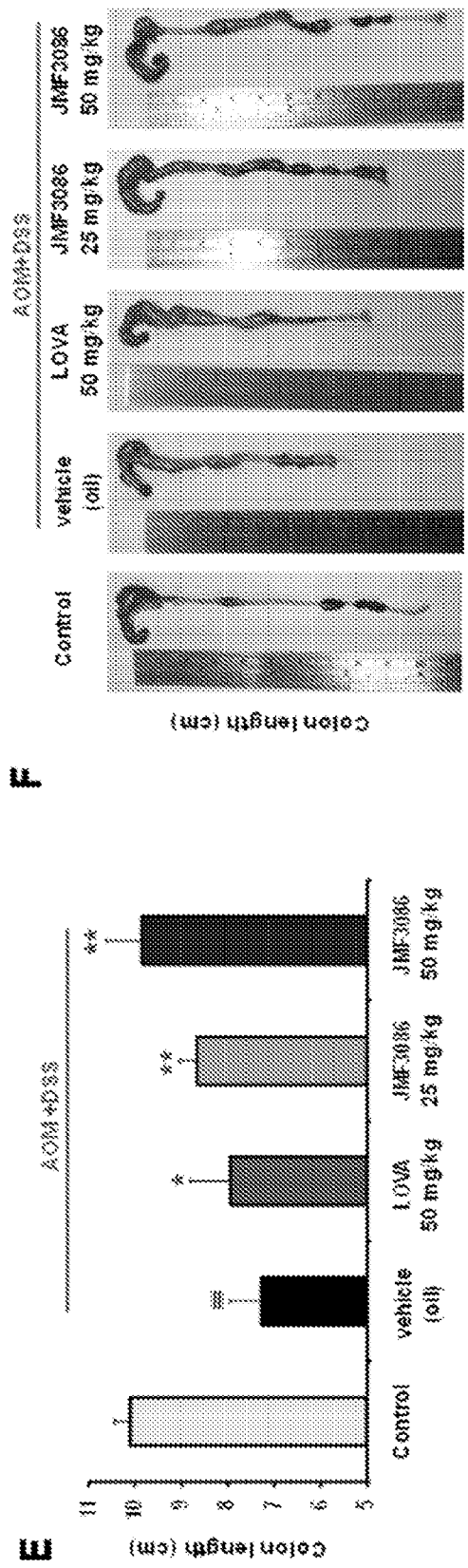
Figures 5G, 5H, 5I:
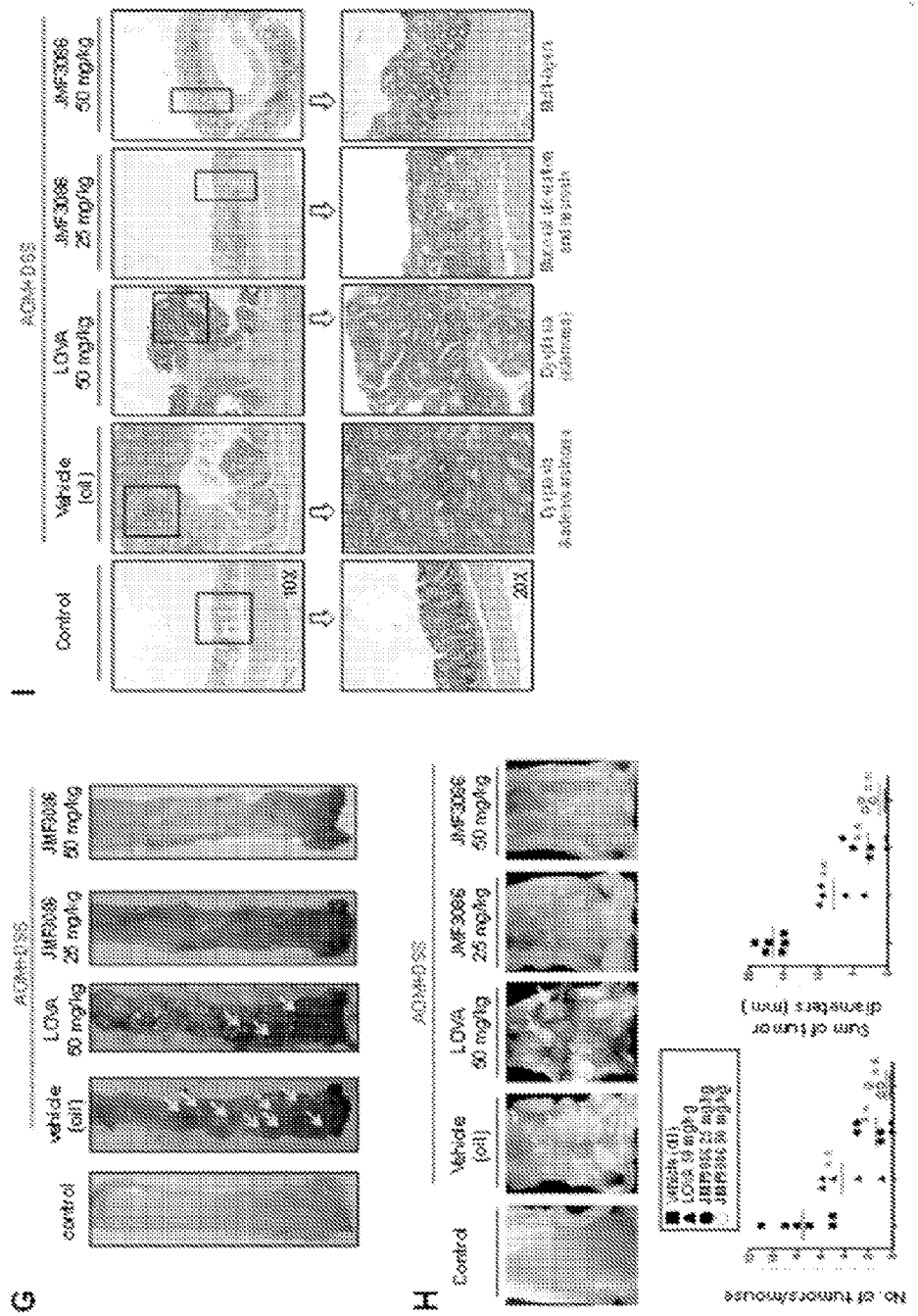

It has been reported that statins have chemopreventive effects on different animal models such as chemical-induced colon tumorigenesis and radiation-induced mammary tumorigenesis in rodent models. (Inano, H. et al. Carcinogenesis 1997, 18, 1723. Narisawa, T. et al. Tohoku J. Exp. Med. 1996, 180, 131. Narisawa, T. et al. Jpn. J. Cancer Res. Gann 1996, 87, 798.) In addition, randomized controlled trials for preventing cardiovascular disease indicated that statins had provocative and unexpected benefits for reducing colorectal cancer and melanoma. (Dellavalle, R. P. et al. Am. J. Ther. 2003, 10, 203. Poynter, J. N. et al. New Engl. J. Med. 2005, 352, 2184.) To investigate whether Lova-HA can prevent cancer, a C57/BL6 mouse model of colitis-associated colorectal cancer (CRC) induced by AOM/DSS was performed. Lova-HA (25 or 50 mg/kg) was orally administered when AOM (12.5 mg/kg body weight, i.p.) was injected five days a week until termination of the experiment (FIG. 5A). Lovastatin administration (50 mg/kg) was compared. The body weight of AOM/DSS mice was dramatically decreased after DSS treatment. Lova-HA but not lovastatin could protect the weight loss (FIG. 5B). The bleeding and diarrhea which are common symptoms of AOM/DSS colitis-associated CRC, were also attenuated by Lova-HA. However, clinical symptoms induced by AOM/DSS were not reversed by lovastatin treatment (FIGS. 5C and 5D). Colon length was reduced in colitis-associated CRC mice (7.6±0.8 cm compared to 10.0±0.3 cm of control), and this effect was reversed by Lova-HA (8.6±0.4 cm for 25 mg/kg, and 10.1±0.9 cm for 50 mg/kg) (FIGS. 5E and 5F). Again, lovastatin could not reverse the decrease in colon length (8.0±0.9 cm). The formation of polyps and colonic tumors were macroscopically observed and counted. Lova-HA at 50 mg/kg completely reduced the number and size of tumors (FIGS. 5G and 5H). Histological examination showed adenocarcinomas with dysplasia in vehicle or lovastatin-treated group. In contrast, the colon mucosa only showed ulceration and necrosis in mice treated with 25 mg/kg of Lova-HA, and normal mucosa was seen in mice treated with 50 mg/kg of Lova-HA (FIG. 5I). These results demonstrated that Lova-HA could prevent the AOM/DSS-induced colon cancer in mice.

(vi) Lova-HA and Atorva-HA Inhibit Colon Carcinogenesis in AOM/DSS Mice

Figures 6A, 6B, 6C, 6D:
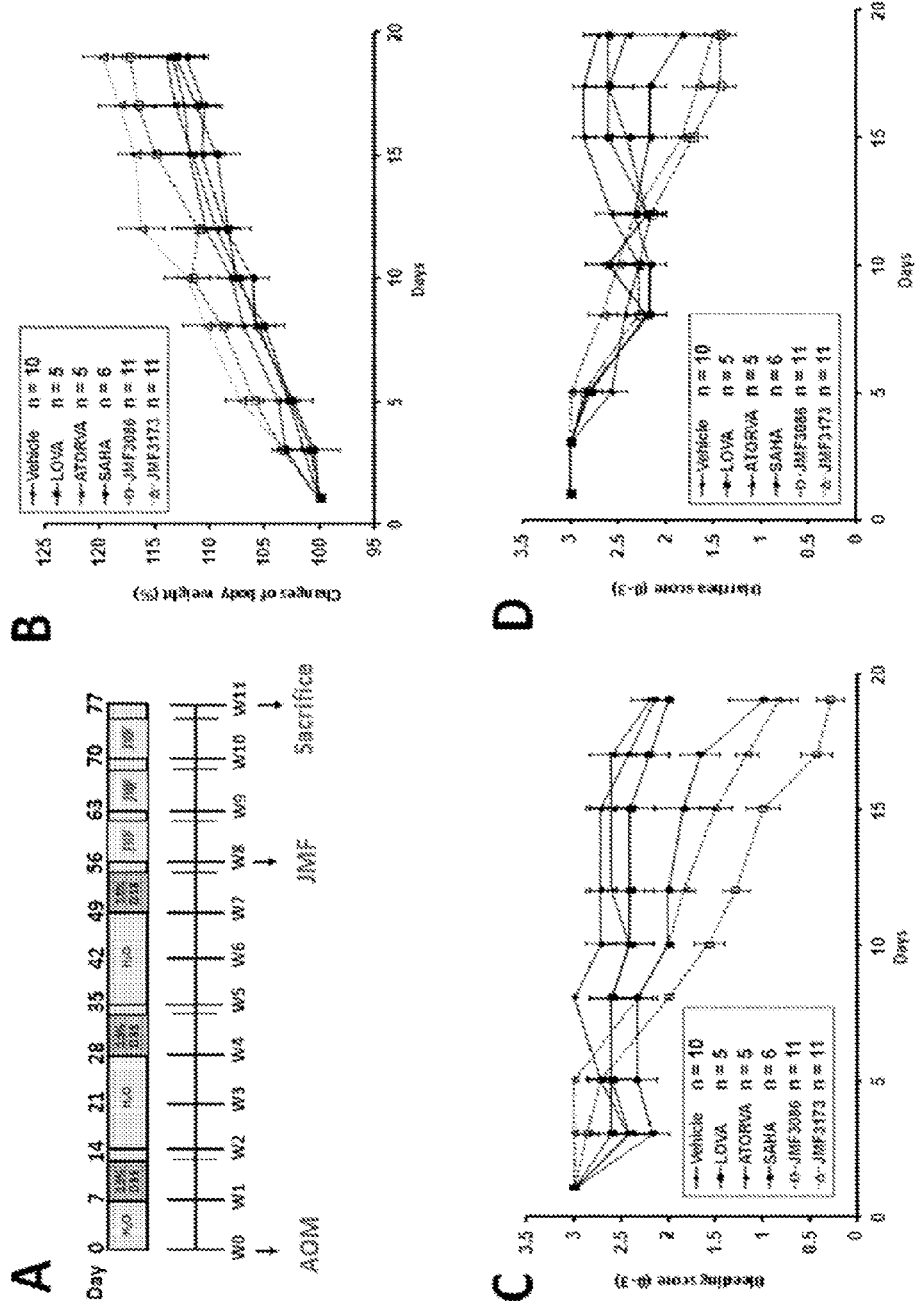
FIG. 6 is a diagram showing the antitumor effect of Lova-HA and Atorva-HA on a mouse model of colitis-associated colorectal cancer. Mice were intraperitoneally injected with AOM (12.5 mg/kg body weight) and maintained for 7 days, then subjected to 3 cycles of DSS treatment (1 cycle representing 5 days of 3.5% DSS followed by 14 days of H2O). Lova-HA and Atorva-HA were dissolved in corn oil. Lova-HA (100 mg/kg), Atorva-HA (100 mg/kg) or the vehicle (corn oil) was orally administered after AOM/DSS treatment 5 days a week for 3 weeks. All mice were sacrificed after 12 weeks and colon segments were fixed in formalin. (6A) Schematic overview of test compounds administration. (6B) Changes in body weights during treatment with Lova-HA, Atorva-HA and statins. (6C) Clinical bleeding scores during stain hydroxamic acids treatment. (6D) Clinical bleeding scores during treatment with with Lova-HA, Atorva-HA and statins. (6E) Colon length. Significant difference between control and AOM/DSS treatment is indicated as ##$P<0.01$. (6F) Macroscopic features of colon. (6G) Representative whole colons. (6H) Representative terminal colons and number of tumors per mouse and total tumor size (represented as sum of diameters of all tumors). (6I) Representative H&E stain of terminal colons.
Figures 6E, 6F:
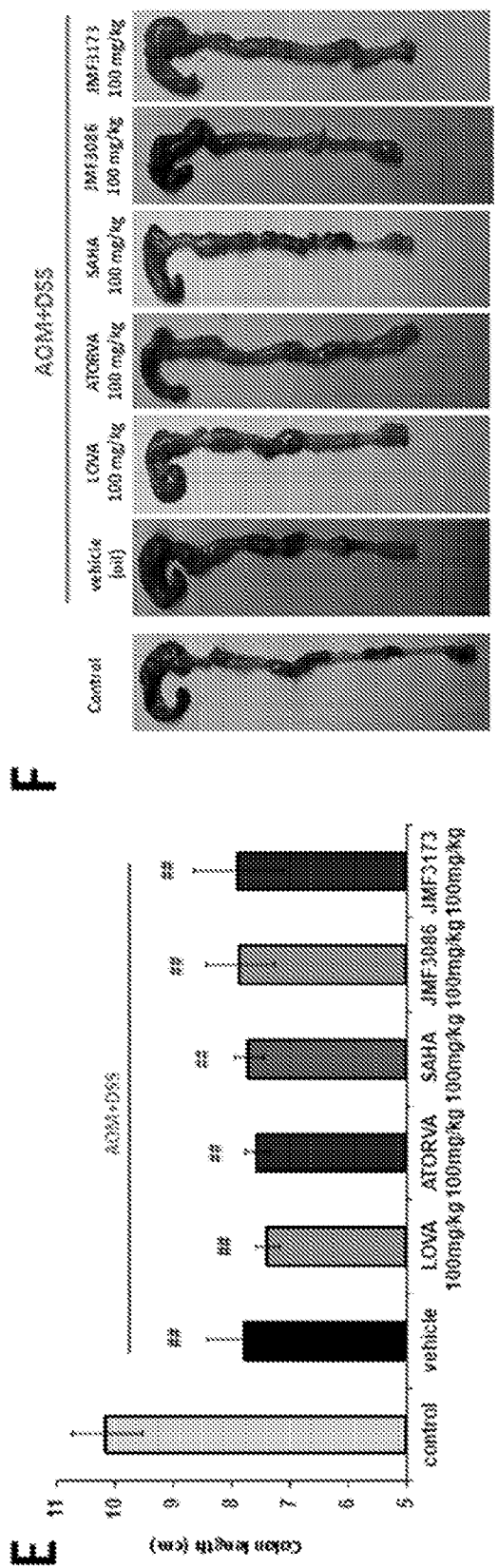
Figure 6G:
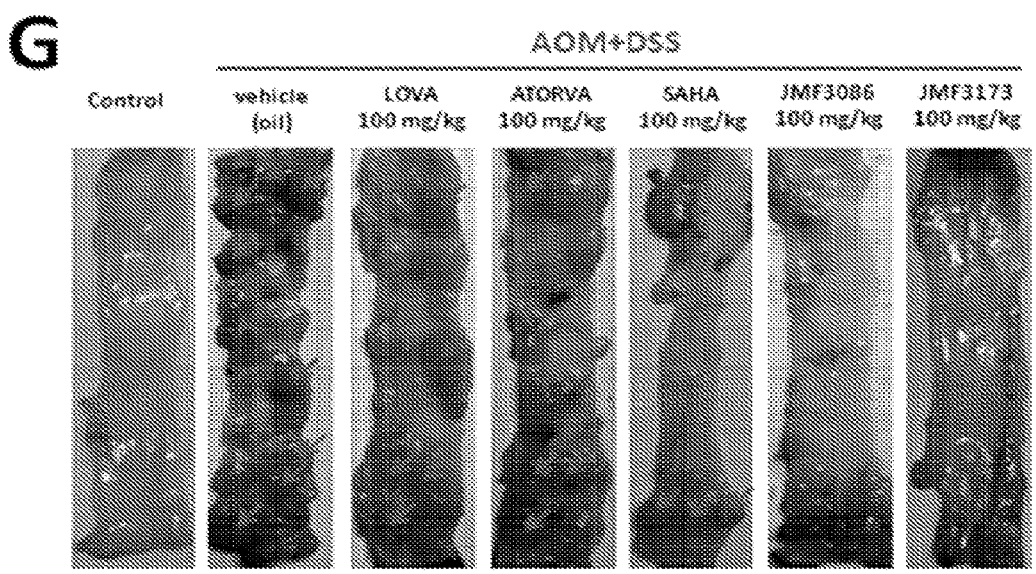
Figure 6H:
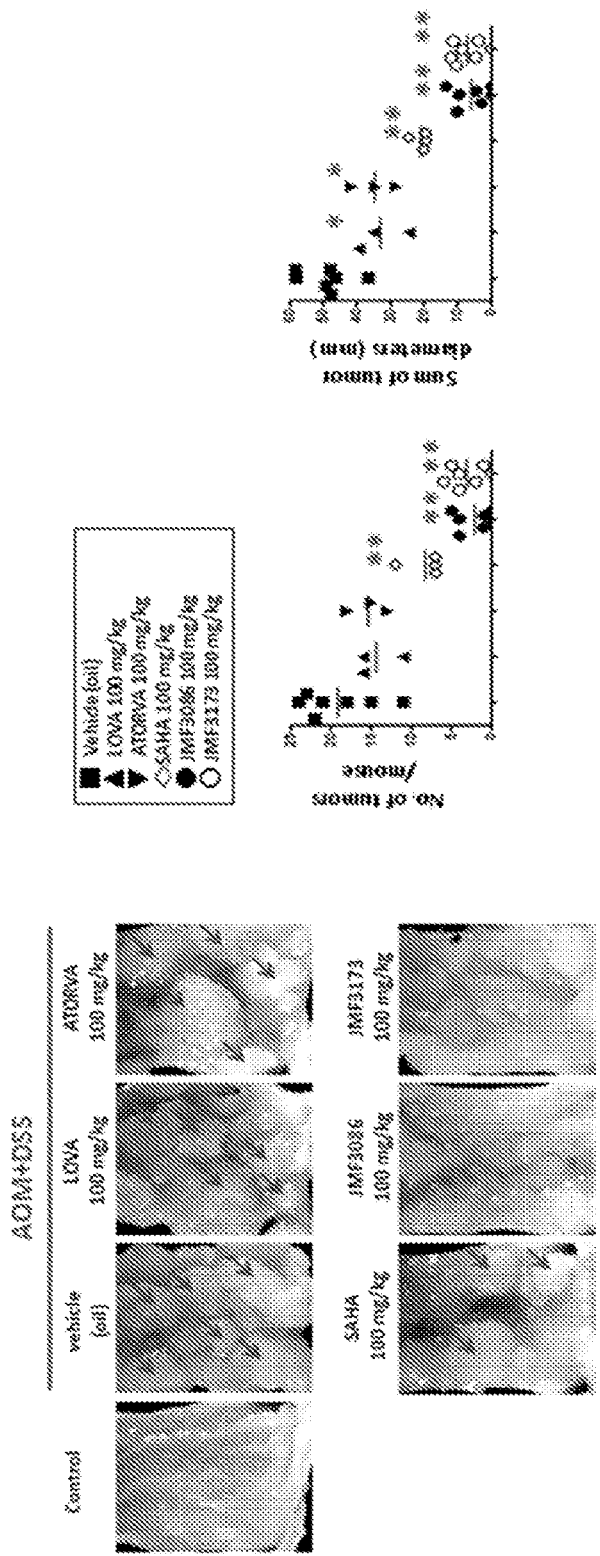
Figure 6I:
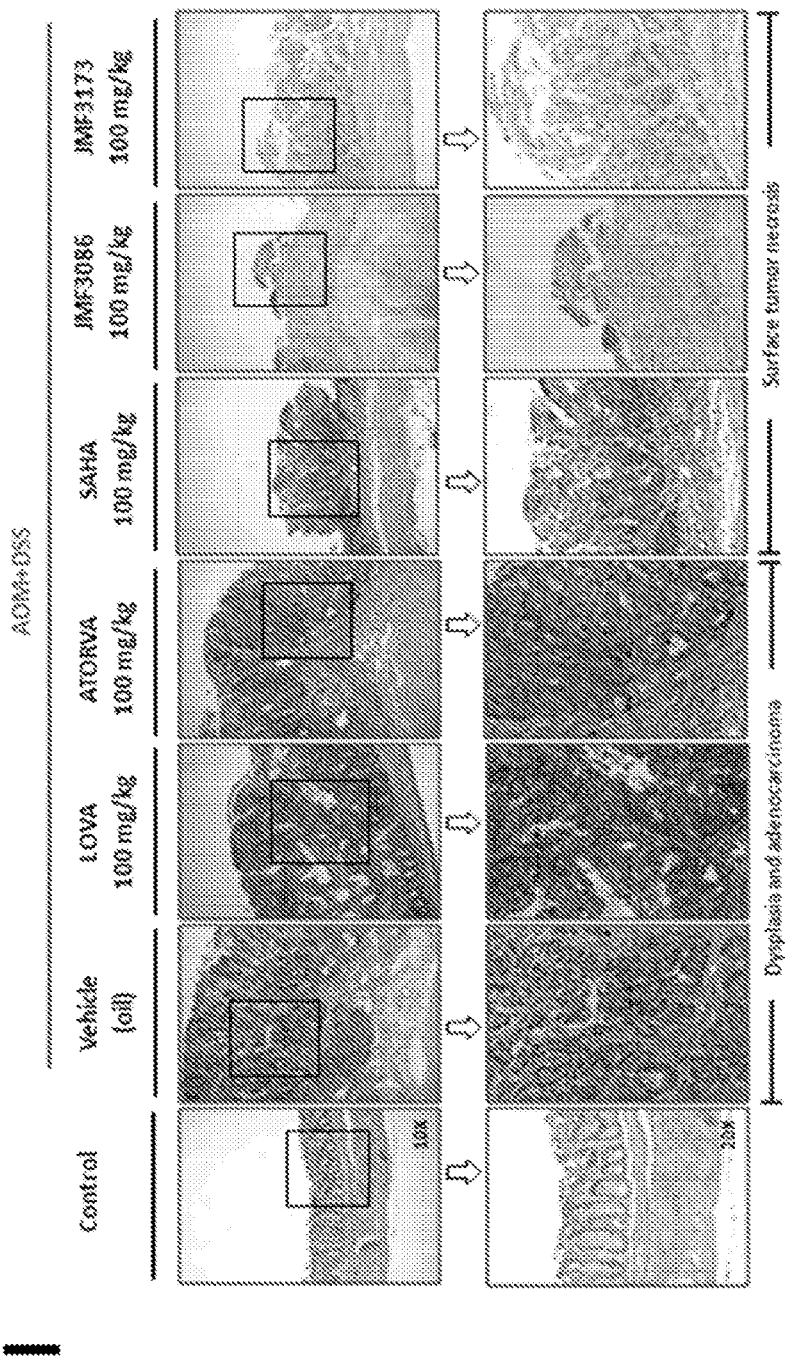

To further investigate whether Lova-HA and Atorva-HA can treat cancer, a C57/BL6 mouse model of colitis-associated CRC was performed after the AOM and 3 cycles of DSS treatment. Lova-HA (100 mg/kg), Atorva-HA (100 mg/kg) or SAHA (100 mg/kg) was orally administered when AOM/DSS was treated five days a week for three weeks (FIG. 6A). Lova-HA and Atorva-HA could protect the weight loss. On the contrary, lovastatin, atorvastatin or SAHA could not protect the AOM/DSS-induced weight loss (FIG. 6B). Clinical symptoms were also attenuated by Lova-HA, Atorva-HA and SAHA. However, those induced by AOM/DSS were not reversed by lovastatin or atorvastatin (FIGS. 6C and 6D). Colon length reduced in colitis-associated CRC model (7.8±0.6 cm compared to 10.1±0.6 cm of control) was not reversed by any treatment (FIGS. 6E and 6F). The formation of polyps and colonic tumors were macroscopically observed and counted. Lova-HA and Atorva-HA at 100 mg/kg markedly reduced the number and size of tumors (FIGS. 6G and 6H). Histological examination showed adenocarcinomas with dysplasia in vehicle, lovastatin- or atorvastatin-treated groups. The colon mucosa showed surface tumor necrosis in SAHA, Lova-HA, and Atorva-HA-treated mice (FIG. 6I). These results demonstrated that Lova-HA and Atorva-HA could inhibit the AOM/DSS-induced CRC in mice.

Example 10

Lova-HA Inhibits the Growth of Colorectal Cancer Cells with Drug Resistance

Figure 7:
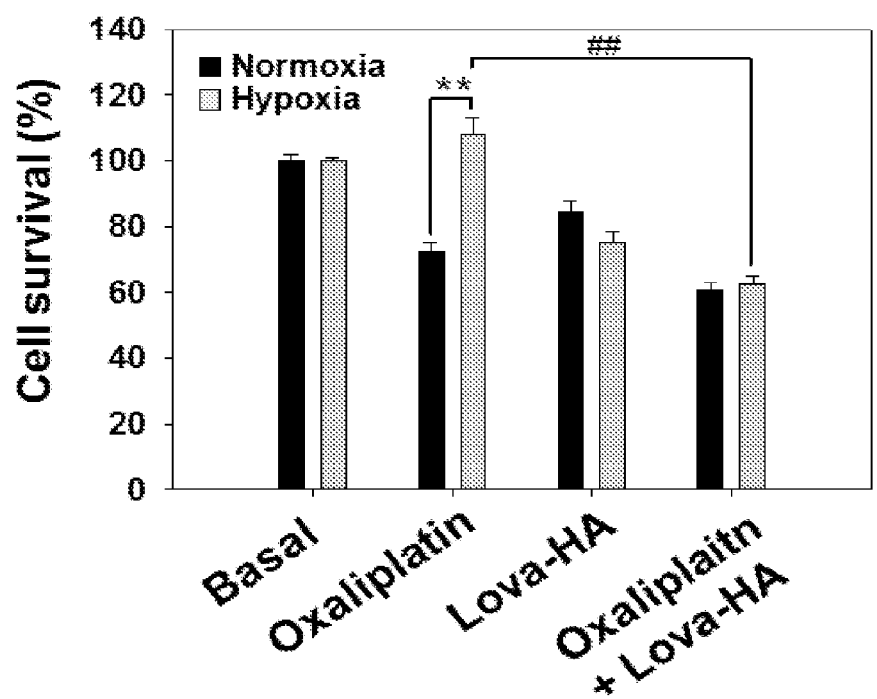
FIG. 7 is a diagram showing the effect of Lova-HA on cell viability in HCT116 colorectal cancer cells under hypoxia. HCT116 cells were treated with oxaliplatin (5 μM), Lova-HA (1 μM), or a combination thereof for 72 hours under normoxia or hypoxia for the first 24 hours. **P<0.01 indicates significant difference between oxaliplatin treatment under normoxia and hypoxia. ##P<0.01 indicates significant difference between oxaliplatin and oxaliplatin plus Lova-HA under hypoxia. Cell viability was assessed by MTT assay.

It has been reported that hypoxia enhanced chemoresistance of solid tumors (Wilson W R and Hay M P. Nat Rev Cancer. 2011 June; 11(6):393-410). To evaluate whether hypoxia induce chemoresistance in colorectal cancer, HCT116 colorectal cancer cells were treated with oxaliplatin under hypoxia condition. Treatment with 5 M oxaliplatin induced cytotoxicity under normoxia. Oxaliplatin resistance was seen under hypoxia (FIG. 7). Lova-HA could overcome hypoxia-induced oxaliplatin resistance (FIG. 7).

REFERENCES

Bolden, J. E.; Peart, M. J.; Johnstone, R. W. Nature Reviews Drug Discovery 2006, 5, 769-784. Anticancer activities of histone deacetylase inhibitors.

Chan, K. K.; Oza, A. M.; Siu, L. L. Clin. Cancer Res. 2003, 9, 10-19. The statins as anticancer agents.

Frantz, S. Nature Reviews Drug Discovery 2006, 881-882. The trouble with making combination drugs.

Gan, Y.; Wang, J.; Coselli, J.; Wang, X. L. Biochem. Biophys. Res. Commun. 2008, 365, 386-392. Synergistic induction of apoptosis by HMG-CoA reductase inhibitor and histone deacetylases inhibitor in HeLa cells.

Gauthaman, K.; Fong, C. Y.; Bongso, A. J. Cellular Biochem. 2009, 106, 975-983. Statins, stem cells, and cancer.

Girgert, R.; Vogt, Y.; Becke, D.; Bruchelt, G.; Schweizer, P. Cancer Lett. 1999, 137, 167-172. Growth inhibition of neuroblastoma cells by lovastatin and L-ascorbic acid is based on different mechanisms.

Hawk, E.; Viner, J. L. New Engl. J. Med. 2005, 352, 2238-2239. Statins and cancer—beyond the "one drug, one disease" model.

Istvan, E. S.; Deisenhofer, J. Science 2001, 292, 1160-1164. Structural mechanism for statin inhibition of HMG-CoA reductase.

Jenuwein, T.; Allis, C. D. Science 2001, 293, 1074-1080. Translating the histone code.

Jones, K. D.; Couldwell, W. T.; Hinton, D. R.; Su, Y.; He, S.; Anker, L.; Law, R. E. Biochem. Biophys. Res. Commun. 1994, 205, 1681-1687. Lovastatin induces growth inhibition and apoptosis in human malignant glioma cells.

Kapur, N. K. Expert Rev. Cardiovascular Ther. 2007, 5, 161-175. Rosuvastatin: a highly potent statin for the prevention and management of coronary artery disease.

Keith, C. T.; Borisy, A. A.; Stockwell, B. R. Nature Reviews Drug Discovery 2005, 4, 71-78. Multicomponent therapeutics for networked systems.

Khanzada, U. K.; Pardo, O. E.; Meier, C.; Downward, J.; Seckl, M. J.; Arcaro, A. Oncogene 2006, 25, 877-887. Potent inhibition of small-cell lung cancer cell growth by simvastatin reveals selective functions of Ras isoforms in growth factor signalling.

Klawitter, J.; Shokati, T.; Moll, V.; Christians, U. Breast Cancer Res. 2010, 12, R16. Effects of lovastatin on breast cancer cells: a proteo-metabonomic study.

Kizer, J. R.; Madias, C.; Wilner, B.; Vaughan, C. J.; Mushlin, A. I.; Trushin, P.; Gotto, A. M., Jr.; Pasternak, R. C. Am. J. Cardiology 2010, 105, 1289-1296. Relation of different measures of low-density lipoprotein cholesterol to risk of coronary artery disease and death in a meta-regression analysis of large-scale trials of statin therapy.

Kostner, G. M. Wien Med. Wochenschr. 1999, 149, 120-124. Pharmacology of HMG CoA reductase inhibitors (statins).

Kwak, E. L.; Clark, J. W.; Chabner, B. Clin. Cancer Res. 2007, 13, 5232-5237. Targeted agents: the rules of combination.

Lane, A. A.; Chabner, B. A. J. Clin. Oncology 2009, 27, 5459-5468. Histone deacetylase inhibitors in cancer therapy.

Lin, Y. C.; Lin, J. H.; Chou, C. W.; Chang, Y. F.; Yeh, S. H.; Chen, C. C. Cancer Res. 2008, 68, 2375-2383. Statins increase p21 through inhibition of histone deacetylase activity and release of promoter-associated HDAC1/2.

Lipinski, C. A.; Lombardo, F.; Dominy, B. W.; Feeney, P. J. Adv. Drug Deliv. Rev. 2001, 46, 3-26. Experimental and computational approaches to estimate solubility and permeability in drug discovery and development settings.

Minden, M. D.; Dimitroulakos, J.; Nohynek, D.; Penn, L. Z. Leukemia lymphoma 2001, 40, 659-662. Lovastatin induced control of blast cell growth in an elderly patient with acute myeloblastic leukemia.

Morphy, R.; Rankovic, Z. J. Med. Chem. 2005, 48, 6523-6543. Designed multiple ligands. An emerging drug discovery paradigm.

Moyad, M. A.; Klotz, L. H. The Urologic Clinics of North America 2011, 38, 325-331. Statin clinical trial (reality) for prostate cancer: an over 15-year wait is finally over thanks to a dietary supplement.

Newman, A.; Clutterbuck, R. D.; Powles, R. L.; Millar, J. L. Leukemia 1994, 8, 274-280. Selective inhibition of primary acute myeloid leukaemia cell growth by lovastatin.

O'Boyle, N. M.; Meegan, M. J. Current Med. Chem. 2011, 18, 4722-4737. Designed multiple ligands for cancer therapy.

Petrelli, A.; Giordano, S. Current Med. Chem. 2008, 15, 422-432. From single- to multi-target drugs in cancer therapy: When aspecificity becomes an advantage.

Pirali, T.; Pagliai, F.; Mercurio, C.; Boggio, R.; Canonico, P. L.; Sorba, G.; Tron, G. C.; Genazzani, A. A. J. Comb. Chem. 2008, 10, 624-627. Triazole-modified histone deacetylase inhibitors as a rapid route to drug discovery.

Poynter, J. N.; Gruber, S. B.; Higgins, P. D.; Almog, R.; Bonner, J. D.; Rennert, H. S.; Low, M.; Greenson, J. K.; Rennert, G. New Engl. J. Med. 2005, 352, 2184-2192. Statins and the risk of colorectal cancer.

Sawyers, C. L. Nature 2007, 449, 993-996. Cancer: mixing cocktails.

Simone, C.; Peserico, A. J. Biomed. Biotechnol. 2011, 2011, 371832. Physical and functional HAT/HDAC interplay regulates protein acetylation balance.

Simone, C.; Peserico, A. J. Biomed. Biotechnol. 2011, 2011, 371832. Physical and functional HAT/HDAC interplay regulates protein acetylation balance.

Shimoyama, S. Cancer Chemother. Pharmacol. 2011, 67, 729-739. Statins are logical candidates for overcoming limitations of targeting therapies on malignancy: their potential application to gastrointestinal cancers.

Slawinska, A.; Kandefer-Szerszen, M. Postepy Hig. Med. Dosw. 2008, 62, 393-404. The anticancer properties of statins.

Sumi, S.; Beauchamp, R. D.; Townsend, C. M., Jr.; Pour, P. M.; Ishizuka, J.;

Thompson, J. C. Pancreas 1994, 9, 657-661. Lovastatin inhibits pancreatic cancer growth regardless of RAS mutation.

Ward, M. M. F1000 Medicine Reports 2009, 1, 35. The JUPITER study: statins for the primary prevention of cardiovascular events in patients with inflammatory rheumatic diseases?

Willard, A. K.; Smith, R. L. J. Labelled Compounds and Radiopharmaceuticals 1982, 19, 337-344. Incorporation of 2(S)-methylbutanoic acid-1-14C into the structure of mevinolin.

Witt, O.; Deubzer, H. E.; Milde, T.; Oehme, I. Cancer Lett. 2009, 277, 8-21. HDAC family: What are the cancer relevant targets?

Zimmermann, G. R.; Lehar, J.; Keith, C. T. Drug Discovery Today 2007, 12, 34-42. Multi-target therapeutics: when the whole is greater than the sum of the parts.

All publications and patent applications cited in this specification are herein incorporated by reference as if each individual publication or patent application were specifically and individually indicated to be incorporated by reference for the purposes or subject matter referenced herein.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

EQUIVALENTS AND SCOPE

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (I):

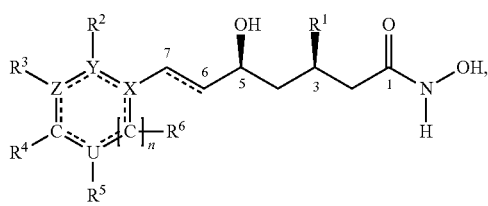

or a pharmaceutically acceptable salt thereof;
wherein:
n is 0 or 1;
==== represents a single or double bond;
X is carbon;
Y, Z, and U are independently carbon or nitrogen; provided that, when Y is carbon and both Z and U are nitrogen, the bond between C6 and C7 is a double bond;

$R^1, R^2, R^3, R^4, R^5$, and $R^6$ are independently selected from the group consisting of null, H, $C_{1-6}$ alkyl, alkenyl, alkynyl, fluoroalkyl, chloroalkyl, bromoalkyl, iodoalkyl, perfluoroalkyl, aryl, heteroaryl, cycloalkyl, cycloalkenyl, aralkyl, aralkenyl, aralkynyl, heteroaralkyl, heteroaralkenyl, heteroaralkynyl, heterocyclyl, acyl, aminocarbonyl, amino, hydroxyl, alkoxy, acyloxy, silyloxy, amido, carbamoyl, and sulfonamido; and $R^3$ is optionally connected with $R^2$ or $R^4$ to form carbocycle or heterocycle.

2. The compound of claim 1, wherein the compound is a 5,N-dihydroxyalkanamide derivative of Formula (III):

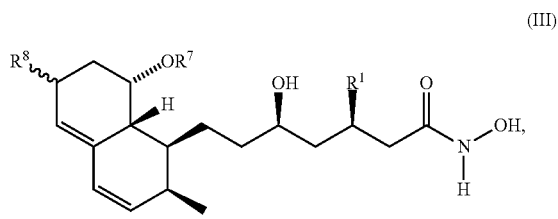

or a pharmaceutically acceptable salt thereof;
wherein:
$R^1$ is selected from the group consisting of $C_{1-6}$ alkyl, alkenyl, alkynyl, fluoroalkyl, chloroalkyl, bromoalkyl, iodoalkyl, perfluoroalkyl, aryl, heteroaryl, cycloalkyl, cycloalkenyl, aralkyl, aralkenyl, aralkynyl, heteroaralkyl, heteroaralkenyl, heteroaralkynyl, heterocyclyl, acyl, aminocarbonyl, amino, hydroxyl, alkoxy, acyloxy, silyloxy, amido, carbamoyl, and sulfonamido;

$R^7$ is selected from the group consisting of H, acyl, $C_{1-6}$ alkyl, alkenyl, alkynyl, and aralkyl; and $R^8$ is selected from the group consisting of H, methyl, and hydroxyl.

3. The compound of claim 2, wherein the compound is selected from the group consisting of:

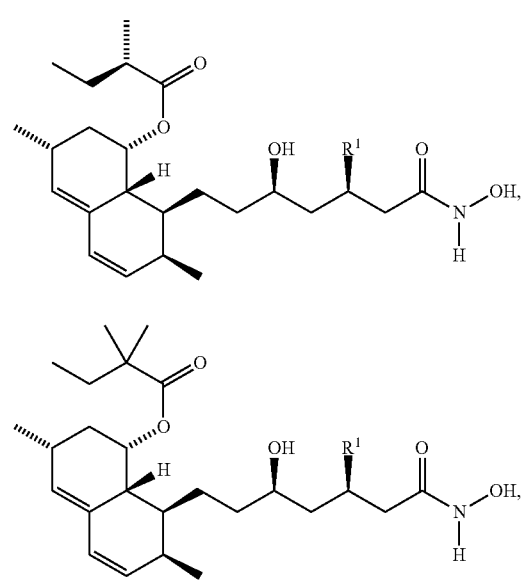

-continued

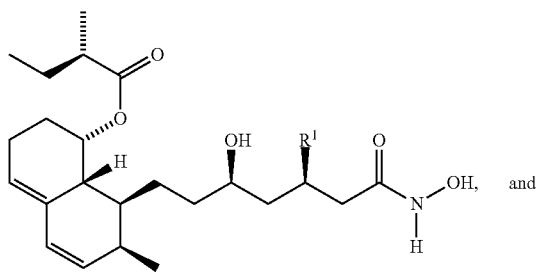

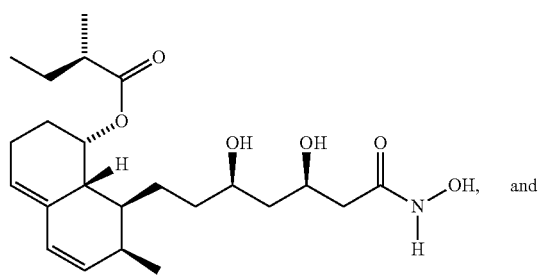

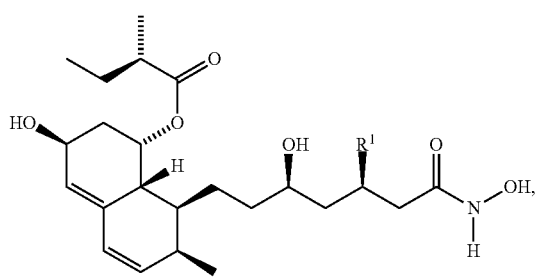

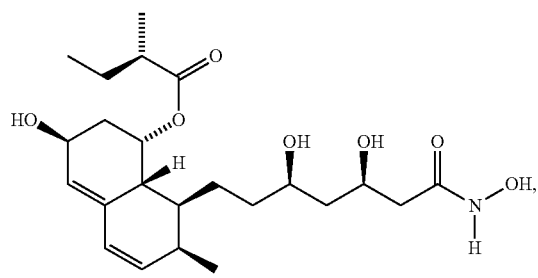

or a pharmaceutically acceptable salt thereof;
wherein:

R$^1$ is selected from the group consisting of C$_{1-6}$ alkyl, alkenyl, alkynyl, fluoroalkyl, chloroalkyl, bromoalkyl, iodoalkyl, perfluoroalkyl, aryl, heteroaryl, cycloalkyl, cycloalkenyl, aralkyl, aralkenyl, aralkynyl, heteroaralkyl, heteroaralkenyl, heteroaralkynyl, heterocyclyl, acyl, aminocarbonyl, amino, hydroxyl, alkoxy, acyloxy, silyloxy, amido, carbamoyl, and sulfonamido.

4. The compound of claim 3, wherein the compound is a 3,5,N-trihydroxy-alkanamide derivative selected from the group consisting of:

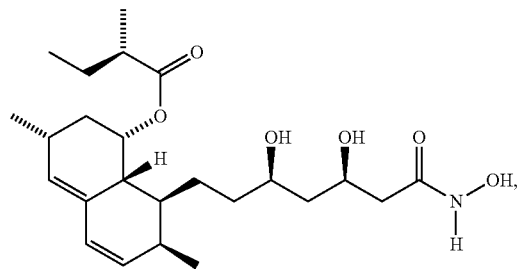

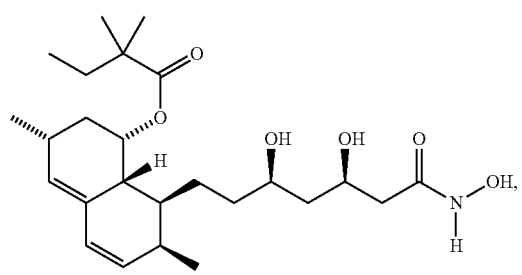

or a pharmaceutically acceptable salt thereof.

5. The compound of claim 3, wherein the compound is a 3-O-(p-methoxybenzyl) derivative selected from the group consisting of:

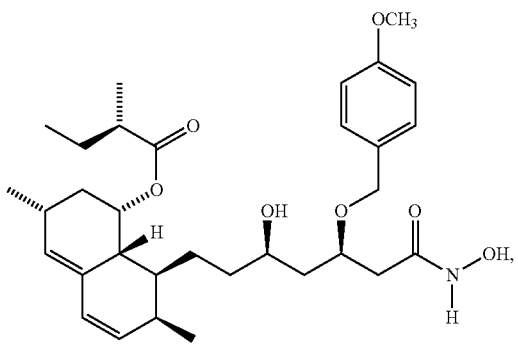

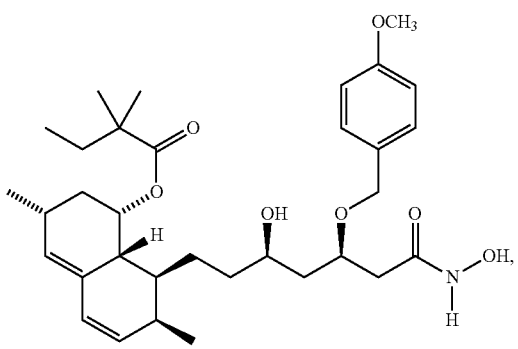

-continued

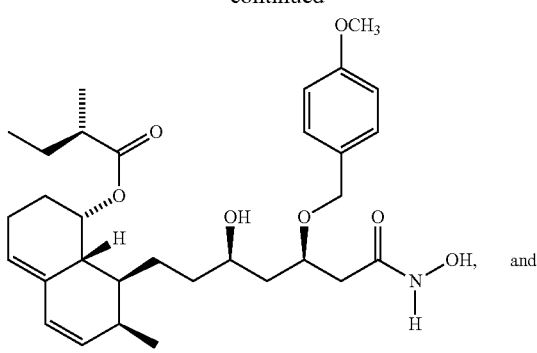

and

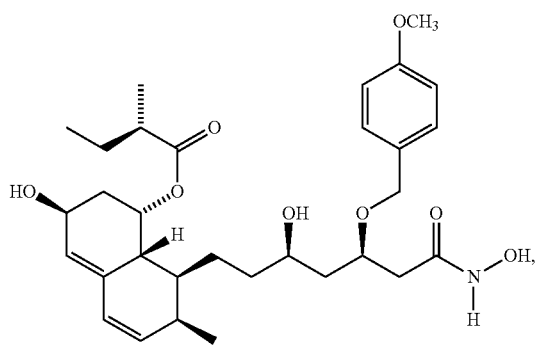

or a pharmaceutically acceptable salt thereof.

6. The compound of claim 1, wherein the compound is of any one of formulas (V), (VII), and (VIII):

(V)

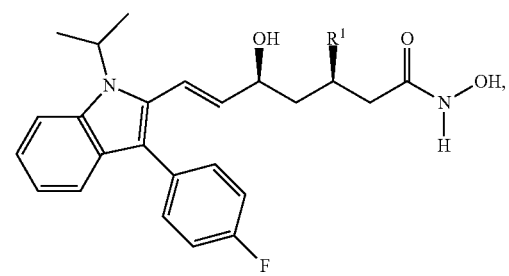

(VII)

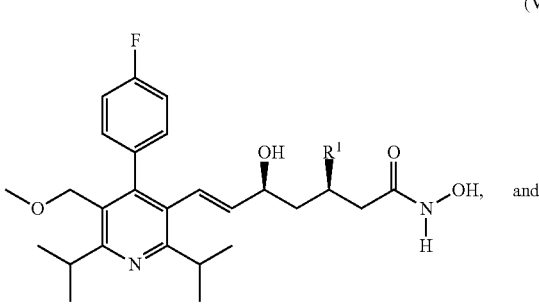

and

-continued (VIII)

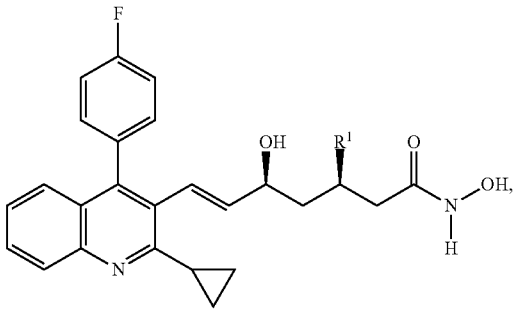

or a pharmaceutically acceptable salt thereof;
wherein:
$R^1$ is selected from the group consisting of $C_{1-6}$ alkyl, alkenyl, alkynyl, fluoroalkyl, chloroalkyl, bromoalkyl, iodoalkyl, perfluoroalkyl, aryl, heteroaryl, cycloalkyl, cycloalkenyl, aralkyl, aralkenyl, aralkynyl, heteroaralkyl, heteroaralkenyl, heteroaralkynyl, heterocyclyl, acyl, aminocarbonyl, amino, hydroxyl, alkoxy, acyloxy, silyloxy, amido, carbamoyl, and sulfonamido.

7. The compound of claim 6, wherein the compound is a 3,5,N-trihydroxy-6-alkenamide derivative selected from the group consisting of:

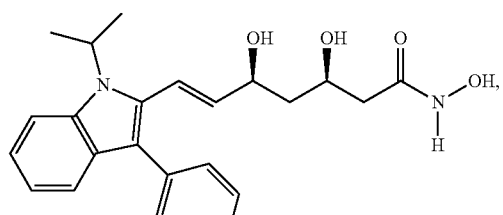

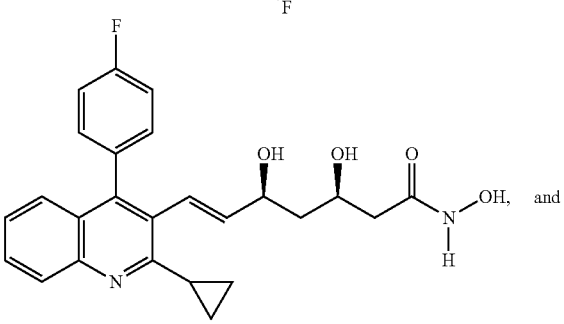

and

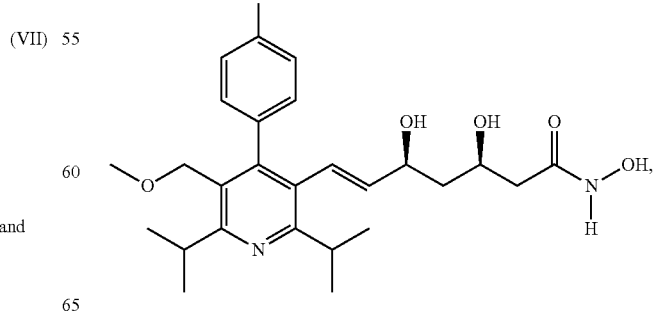

or a pharmaceutically acceptable salt thereof.

8. The compound of claim 6, wherein the compound is a p-methoxybenzyl derivative selected from the group consisting of:

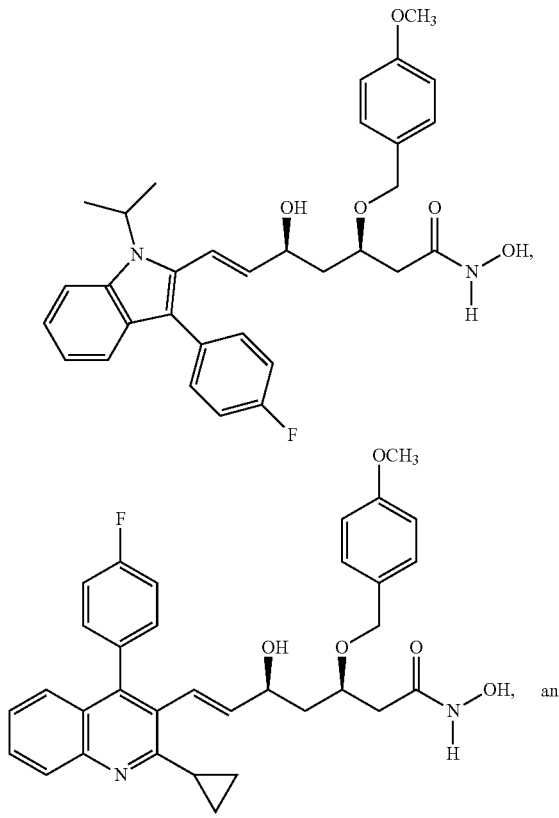

or a pharmaceutically acceptable salt thereof.

9. A compound of Formula (IV):

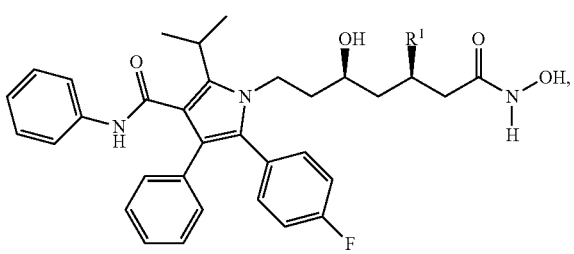

or a pharmaceutically acceptable salt thereof;

wherein:
R$^1$ is selected from the group consisting of C$_{1-6}$ alkyl, alkenyl, alkynyl, fluoroalkyl, chloroalkyl, bromoalkyl, iodoalkyl, perfluoroalkyl, aryl, heteroaryl, cycloalkyl, cycloalkenyl, aralkyl, aralkenyl, aralkynyl, heteroaralkyl, heteroaralkenyl, heteroaralkynyl, heterocyclyl, acyl, aminocarbonyl, amino, alkoxy, acyloxy, silyloxy, amido, carbamoyl, and sulfonamido.

10. The compound of claim 9, wherein the compound is a 3-O-(p-methoxybenzyl) derivative of the formula:

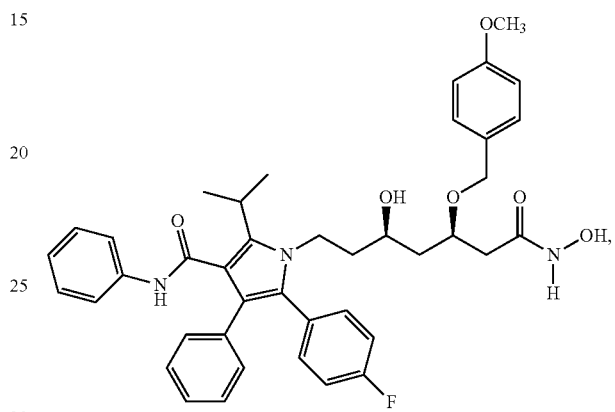

or a pharmaceutically acceptable salt thereof.

11. A compound of Formula (VI):

(VI)

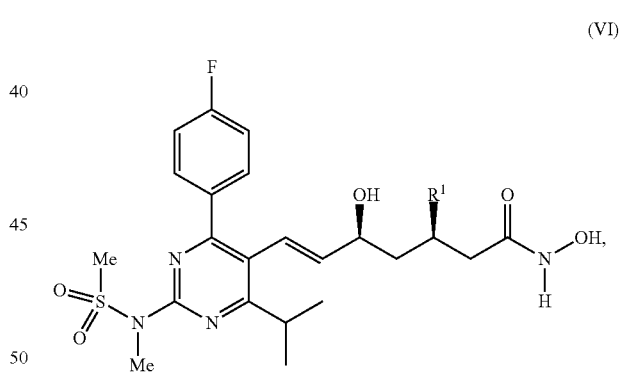

or a pharmaceutically acceptable salt thereof;

wherein:
R$^1$ is selected from the group consisting of C$_{1-6}$ alkyl, alkenyl, alkynyl, fluoroalkyl, chloroalkyl, bromoalkyl, iodoalkyl, perfluoroalkyl, aryl, heteroaryl, cycloalkyl, cycloalkenyl, aralkyl, aralkenyl, aralkynyl, heteroaralkyl, heteroaralkenyl, heteroaralkynyl, heterocyclyl, acyl, aminocarbonyl, amino, hydroxyl, alkoxy, acyloxy, silyloxy, amido, carbamoyl, and sulfonamido.

12. The compound of claim 11, wherein the compound is a 3,5,N-trihydroxy-6-alkenamide derivative of the formula:

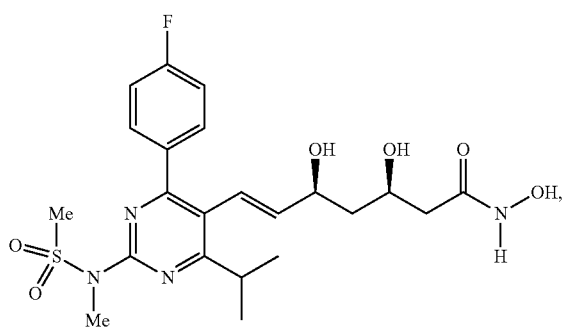 [SMILES: CC(C)c1nc(N(C)S(C)(=O)=O)nc(-c2ccc(F)cc2)c1/C=C/[C@@H](O)C[C@@H](O)CC(=O)NO]

or a pharmaceutically acceptable salt thereof.

13. The compound of claim 11, wherein the compound is a p-methoxybenzyl derivative of the formula:

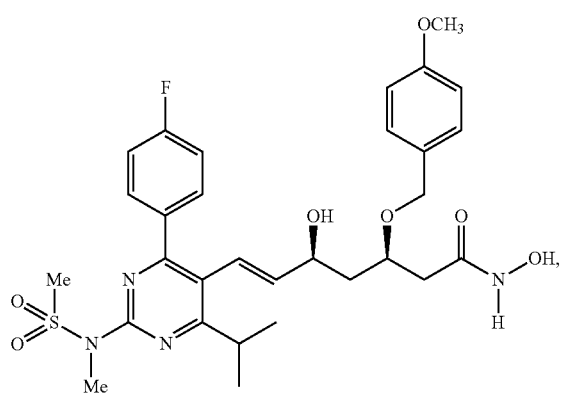 [SMILES: COc1ccc(CO[C@@H](CC(=O)NO)C[C@H](O)/C=C/c2c(-c3ccc(F)cc3)nc(N(C)S(C)(=O)=O)nc2C(C)C)cc1]

or a pharmaceutically acceptable salt thereof.

14. A pharmaceutical composition comprising a compound of claim 1, or a pharmaceutically acceptable salt thereof, and a pharmaceutically acceptable excipient.

15. A method for treating cancer, hypercholesterolemia, an acute or chronic inflammatory disease, an autoimmune disease, an allergic disease, or a neurodegenerative disease, comprising administering to a human subject in need thereof a therapeutically effective amount of a pharmaceutical composition of claim 14,
wherein the acute or chronic inflammatory disease is selected from the group consisting of inflammatory bowel disease, necrotizing enterocolitis, and rheumatoid arthritis,
wherein the autoimmune disease is selected from the group consisting of systemic lupus erythematosis, rheumatoid, arthritis, psoriasis, Crohn's disease, and multiple sclerosis,
wherein the allergic disease is selected from the group consisting of allergic bronchitis and asthma,
wherein the neurodegenerative disease is selected from the group consisting of Alzheimer's disease, amyotrophic lateral sclerosis, Huntington's disease, and Parkinson's disease, and
wherein, the cancer is selected from the group consisting of leukemia, Hodgkin's disease, lymphoma, Ewing's sarcoma, multiple myeloma, Wilms' tumor, bone tumor, neuroblastoma, retinoblastoma, testicular cancer, thyroid cancer, prostate cancer, larynx cancer, cervical cancer, nasopharynx cancer, breast cancer, colon cancer, pancreatic cancer, head and neck cancer, esophageal cancer, rectal cancer, small-cell lung cancer, non-small-cell lung cancer, brain cancer, melanoma and other skin cancers, and CNS neoplasm.

16. The method of claim 15, wherein the human subject is having, suspected of having, or at risk for the cancer.

17. A method for inhibiting the drug resistance of a cancer cell, comprising:
contacting the cancer cell with an effective amount of a pharmaceutical composition of claim 14, wherein, the cancer is selected from the group consisting of leukemia, Hodgkin's disease, lymphoma, Ewing's sarcoma, multiple myeloma, Wilms' tumor, bone tumor, neuroblastoma, retinoblastoma, testicular cancer, thyroid cancer, prostate cancer, larynx cancer, cervical cancer, nasopharynx cancer, breast cancer, colon cancer, pancreatic cancer, head and neck cancer, esophageal cancer, rectal cancer, small-cell lung cancer, non-small-cell lung caner, brain cancer, melanoma and other skin cancers, and CNS neoplasm.

18. The method of claim 17, wherein the cancer cell is further treated with an anti-cancer drug.

19. The method of claim 17, wherein said cell is an in vivo cell.

20. A method for manufacturing a compound of Formula (I), the method comprising:
contacting a compound of Formula (II), or a salt thereof, with hydroxylamine, or a salt thereof:

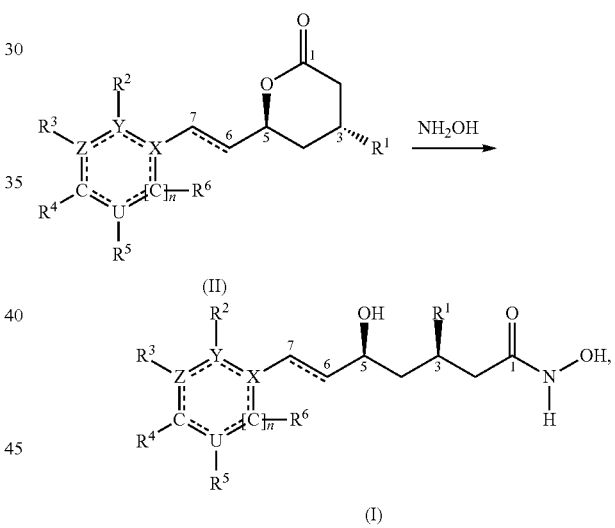

wherein:
n is 0 or 1;
U, X, Y, and Z are independently selected from the group consisting of carbon and nitrogen;
==== represents a single or double bond;
$R^1$, $R^2$, $R^3$, $R^4$, $R^5$ and $R^6$ are independently selected from the group consisting of $C_{1-6}$ alkyl, alkenyl, alkynyl, fluoroalkyl, chloroalkyl, bromoalkyl, iodoalkyl, perfluoroalkyl, aryl, heteroaryl, cycloalkyl, cycloalkenyl, aralkyl, aralkenyl, aralkynyl, heteroaralkyl, heteroaralkenyl, heteroaralkynyl, heterocyclyl, acyl, aminocarbonyl, amino, hydroxyl, alkoxy, acyloxy, silyloxy, amido, carbamoyl, and sulfonamido; and
$R^3$ is optionally connected with $R^2$ or $R^4$ to form carbocycle or heterocycle.

21. The method of claim 20, wherein hydroxylamine is in solution or is generated in situ by contacting a salt of hydroxylamine with a base.

22. The method of claim 21, wherein the salt is selected from the group consisting of hydrochloride, nitrate, phosphate, and sulfate salts.

23. The method of claim 21, wherein the base is selected from the group consisting of hydroxide, carbonate, bicarbonate, methoxide, ethoxide, isopropoxide, and tert-butoxide with the counter cation selected from the group consisting of lithium, sodium, potassium, cesium, calcium, and barium.

24. The method of claim 20, wherein a Lewis acid is used as a reaction promotor, and wherein the Lewis acid is selected from the group consisting of lithium, magnesium, calcium, zinc, aluminum; boron, indium, scandium, ytterbium, cerium, silicon, tin, titanium, zirconium, vanadium, iron, and cobalt salts with the counter anion selected from the group consisting of fluoride, chloride, bromide, iodide, hydroxide, methoxide, ethoxide, isoproproxide, tert-butoxide, acetate, oxalate, acetylacetonate, nitrate, phosphate, sulfate, bisulfate, and sulfonate.

25. The method of claim 20, wherein the step of contacting is conducted in a hydrocarbon, ethereal, chlorinated, or alcoholic solvent, or a mixture thereof.

26. The method of claim 25, wherein the hydrocarbon solvent is an acyclic, cyclic, or aromatic solvent selected from the group consisting of n-hexane, cyclohexane, benzene, toluene, and xylene.

27. The method of claim 25, wherein the ethereal solvent is an acyclic or cyclic solvent selected from the group consisting of diethyl ether, methyl tert-butyl ether, dimethoxyethane, tetrahydrofuran, and 1,4-dioxane.

28. The method of claim 20, wherein:

X is carbon; and

Y, Z, and U are independently selected from the group consisting of carbon and nitrogen; with the proviso that the bond between C6 and C7 is a double bond when Y is carbon and both Z and U are nitrogen.

* * * * *